(12) United States Patent
Saus et al.

(10) Patent No.: US 10,633,455 B2
(45) Date of Patent: Apr. 28, 2020

(54) METHOD FOR TREATING AND DIAGNOSING DISEASE USING INHIBITORS OF GOODPASTURE ANTIGEN BINDING PROTEIN

(71) Applicant: Fibrostatin S.L., Valencia (ES)

(72) Inventors: Juan Saus, Valencia (ES); Fernando Revert, Valencia (ES); Ramón Merino Pérez, Cantabria (ES); Jesús Merino Pérez, Cantabria (ES); Francisco Revert-Ros, Valencia (ES)

(73) Assignee: University of Valencia, Valencia (ES)

( * ) Notice: Subject to any disclaimer, the term of this patent is extended or adjusted under 35 U.S.C. 154(b) by 0 days.

(21) Appl. No.: 15/485,827

(22) Filed: Apr. 12, 2017

(65) Prior Publication Data

US 2017/0218088 A1 Aug. 3, 2017

Related U.S. Application Data

(62) Division of application No. 13/400,831, filed on Feb. 21, 2012, now abandoned.

(60) Provisional application No. 61/473,411, filed on Apr. 8, 2011, provisional application No. 61/469,945, filed on Mar. 31, 2011, provisional application No. 61/444,872, filed on Feb. 21, 2011.

(51) Int. Cl.
| | | |
|---|---|---|
| *A61K 31/352* | (2006.01) | |
| *A61K 31/353* | (2006.01) | |
| *A61K 31/4409* | (2006.01) | |
| *A61K 38/16* | (2006.01) | |
| *A61K 39/00* | (2006.01) | |
| *G01N 33/573* | (2006.01) | |
| *G01N 33/68* | (2006.01) | |
| *C07K 16/40* | (2006.01) | |

(52) U.S. Cl.
CPC ............ *C07K 16/40* (2013.01); *A61K 31/352* (2013.01); *A61K 31/353* (2013.01); *A61K 31/4409* (2013.01); *A61K 38/16* (2013.01); *C12Y 207/11009* (2013.01); *G01N 33/573* (2013.01); *G01N 33/6893* (2013.01); *A61K 2039/505* (2013.01); *C07K 2317/76* (2013.01); *G01N 2333/4737* (2013.01); *G01N 2333/912* (2013.01); *G01N 2800/12* (2013.01)

(58) Field of Classification Search
CPC combination set(s) only.
See application file for complete search history.

(56) References Cited

U.S. PATENT DOCUMENTS

| | | | |
|---|---|---|---|
| 5,625,048 A | 4/1997 | Tsien et al. | |
| 6,124,128 A | 9/2000 | Tsien et al. | |
| 6,579,969 B1 | 6/2003 | Saus et al. | |
| 6,881,547 B1 | 4/2005 | Saus | |
| 7,326,768 B2 | 2/2008 | Saus et al. | |
| 7,629,132 B2 * | 12/2009 | Saus | ...................... C07K 16/40 435/7.1 |
| 7,935,492 B2 | 5/2011 | Saus et al. | |
| 8,586,776 B2 * | 11/2013 | Saus | ...................... C07C 45/68 560/53 |
| 2010/0021935 A1 | 1/2010 | Saus et al. | |

FOREIGN PATENT DOCUMENTS

| | | | |
|---|---|---|---|
| WO | 1996/023810 | 4/1996 | |
| WO | 2000/050607 | 8/2000 | |
| WO | 2002/061430 | 8/2002 | |
| WO | 2004/070025 | 8/2004 | |
| WO | 2007/087689 | 8/2007 | |
| WO | 2009/009019 | 1/2009 | |
| WO | 2009/017833 | 2/2009 | |
| WO | WO-2009108720 A2 * | 9/2009 | ........... C07D 233/06 |
| WO | 2010/009856 | 1/2010 | |
| WO | 2011/054530 | 5/2011 | |

OTHER PUBLICATIONS

Yin et al. "Terphenyl-Based Bak BH3 alpha-Helical Proteomimetics as Low-Molecular-Weight Antagonists of Bcl-xL J. Am. Chem. Soc. 2005, 127, 10191-10196." (Year: 2005).*
Kang et al. "Transforming Growth Factor (TGF)-beta-1 Stimulates Pulmonary Fibrosis and Inflammation via a Bax-dependent, Bid-activated Pathway That Involves Matrix Metalloproteinase-12" J. Biol. Chem. 2007, 282, 7723-7732. (Year: 2007).*
Wieslander, et al., (1985) J Biol Chem, 260:8564-70.
Prasher, et al., Gene, 111:229233 (1992).
Heim, et al., Proc. Nat. Acad. Sci., USA, 91:12501 (1994).
Levine, et al., Comp Biochem Physiol., 72B:77-85 (1982).
Cubitt, et al., Trends Biochem Sci. 20:448-455 (1995).
Heim & Tsien, Current Biol. 6: 178-182 (1996).
Tsien, et al., Trends Cell Biol. 3:242-245 (1993).
Evans et al., J. Immunoi. Meth. 184: 123-38 (1995).
González, et al. J Immunol 2007; 178: 2778-2786.
Raya, et al. J Biol Chem 1999; 274: 12642-12649.
Raya, et al. J Biol Chem 2000; 275: 40392-40399.
Revert, et al. Am J Pathol 2007; 171: 1419-1430.
Revert, et al. J Biol Chem 2008; 283: 30246-30255.
Netzer, et al. J Biol Chem 1999; 274: 11267-11274.
Benjamin, et al. J R Statist Soc B 1995; 57: 289-300.
Medina, et al. Nucleic Acids Res 2010; 38 (Web Server issue): W210-W213.
McCormick, et al. J Immunol. 1999; 163:5693-5699.
Cortijo, et al. Br J Pharmacol 2009; 156: 534-44.
Noth, et al. Chest 2007; 132: 637-650.
Sleijfer, et al. Chest 2001; 120: 617-624.
Injac, et al. Technol Cancer Res Treat 2008; 7: 497-516.
Meadors, et al. Semin Oncol 2006; 33: 98-105.
Öz, et al. Mol Cell Biochem 2006; 286: 11-15.

(Continued)

*Primary Examiner* — Amanda L Aguirre
(74) *Attorney, Agent, or Firm* — McDonnell Boehnen Hulbert & Berghoff LLP

(57) ABSTRACT

The present invention provides methods for the diagnosis and/or treatment of chronic kidney disease, immune complex-mediated GN, rheumatoid arthritis, and pulmonary fibrosis, and methods for identifying compounds for such therapeutic use.

8 Claims, 10 Drawing Sheets

Specification includes a Sequence Listing.

(56) References Cited

OTHER PUBLICATIONS

Granero, et al. FEBS J 2005; 272: 5291-5305.
Miralem, et al. J Biol Chem 2010; 285:12551-12558.
Martinon, et al. Mol Cell 2002; 10: 417-26.
Cassel, et al. Semin Immunol 2009; 21: 194-198.
Mariathasan, et al. Nature 2004; 430: 213-218.
Kumagai, et al. (2007) J. Biol. Chem. 282,17758-17766.
Lemmon and Ferguson. (2000) Biochem J. 350, 1-18.
Dowler, et al. (2000) Biochem. J. 351,19-31.
Loewen, et al. (2003) EMBO J. 22,2025-2035.
Kanekura, et al. (2006) J. Biol. Chem. 281,30223-30233.
Wyles, et al. (2002) J. Biol. Chem. 277, 29908-29918.
Soccio, et al. (2003) J. Biol. Chem. 278,22183-22186.
Alpy, et al. (2005) J. Cell Sci. 118,2791-2801.
Bendtsen, et al (2004)Protein Eng Des Sel 17, 349-356.
Yang and Li (2005) Mol. Cells 20, 173-182.
Ni and Lee (2007) FEBS Lett 581,3641-3651.
Perry and Ridgway (2006) Mol Biol Cell 17,2604-2616.
Kawano, et al. (2006) J. Biol Chem 281, 30279-30288.
Peabody, D S (1989) J. Biol Chem 264,5031-5035.
Touriol, et al. (2003) Biol Cell 95, 169-178.
Calvete, et al (2006) Proteomics 6, S237-S244.
Swanton, et al. (2007) Cancer Cell 11, 498-512.
Granero-Molto, et al. (2008) J. Biol Chem, Apr. 18 [Epub ahead of print].
Rual, et al. (2005) Nature 437,1173-1178.
Haas M. "IgA Nephropathy and Henoch-Schonlein Purpura Nephritis". Heptinstall's Pathology of the Kidney. Edited by Jennette JC, Olson JL, Schwartz MM, Silva FG. Philadelphia, Lippincott Williams & Wilkins Publishers 2007, pp. 423-486.
Balow, et al. "Systemic Lupus Erythematosus and the kidney". Systemic Lupus Erythematosus. Edited by Lahita RG. San Diego, Academic Press, 1999, pp. 657-685.
Borza,et al. (2005) J. Biol. Chem. 280, 27147-27154.
Yoshida, et al. (2001) Cell 107,881-891.
Fink, et al. Infect Immun 2005; 73: 1907-1916.
Hanada, et al. Nature 2003; 426: 803-809.
Fugmann, et al. J Cell Biol 2007; 178: 15-22.
Hudson, et al. N Engl J Med 2003; 348: 2543-2556.
Chung, et al. Circulation 2003; 107: 3133-3140.
Sauter, et al. Cancer Biol Ther 2011; 11: 1008-1016.
Schroder, et al. Science 2010; 327: 296-300.
Perregaux, et al. J Biol Chem 1994; 269: 15195-15203.
Batuca, et al. Autoimmunity 2009; 42: 282-285.
Sanz, et al. Nat Rev Drug Discov 2011; 10: 335-336.
Church, et al. Nat Clin Pract Rheumatol 2008; 4: 34-42.
Timoshanko, et al. J Am Soc Nephrol 2004; 15: 910-918.
Goldbach-Mansky, et al. J Allergy Clin Immunol 2009; 124: 1141-9; quiz 1150-1.
Aringer, et al. Lupus 2005; 14: 13-18.
Bauemfeind, et al. J Immunol 2009; 183: 787-791.
Penadés, et al. Eur J Biochem 1995; 229: 754-760.
Lamour, et al. J Lipid Res. 2007; 48:1293-304.
Ward et al., (1989) Nature 341:544-546.
Kohler and Milstein, Nature 256,495-497 (1975).
Jones et al., Nature 321:522-525 (1986).
Morrison et al., Proc. Natl. Acad. Sci., U.S.A., 81:6851-6855 (1984).
Morrison and Oi, Adv. Immunol., 44:65-92 (1988).
Verhoeyer et al, Science 239:1534-1536 (1988).
Padlan, Molec. Immun. 28:489-498 (1991).
Padlan, Molec. Immunol. 31(3):169-217 (1994).
Kettleborough, et al., Protein Eng. 4(7):773-83 (1991).
Vandanmagsar, et al. Nat Med 2011; 17: 179-88.
Holmdahl, et al. Ageing Res Rev 2002; 1, 135-147.
Jansson, et al. Clin Exp Immunol 1992; 89: 446-451.
Donadio and Grande (2002) N Engl J Med 347, 738-748.
ISR for PCT/EP2012/052923, mailed Apr. 12, 2012.
DeMattos et al. "Peripheral anti-A13 antibody alters CNS and plasma Aβ clearance and decreases brain Aβ burden in mouse model of Alzheimer's disease" Proc Natl Acad Sci (2001) vol. 98(15), pp. 8850-8855.
Bard et al. "Peripherally administered antibodies against amyloid beta-peptide enter the central nervous system and reduce pathology in a mouse model of Alzheimer disease" Nature Medicine (2000) vol. 6(8), pp. 916-919.

* cited by examiner

SEQUENCE LISTING

<160> NUMBER OF SEQ ID NOS: 30

<210> SEQ ID NO 1
<211> LENGTH: 624
<212> TYPE: PRT
<213> ORGANISM: Homo sapiens

<400> SEQUENCE: 1

```
Met Ser Asp Asn Gln Ser Trp Asn Ser Ser Gly Ser Glu Glu Asp Pro
1               5                   10                  15

Glu Thr Glu Ser Gly Pro Pro Val Glu Arg Cys Gly Val Leu Ser Lys
            20                  25                  30

Trp Thr Asn Tyr Ile His Gly Trp Gln Asp Arg Trp Val Val Leu Lys
        35                  40                  45

Asn Asn Ala Leu Ser Tyr Tyr Lys Ser Glu Asp Glu Thr Glu Tyr Gly
    50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
```

-continued

```
            115                 120                 125
Arg His Gly Ser Met Val Ser Leu Val Ser Gly Ala Ser Gly Tyr Ser
130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                    165                 170                 175

Thr Leu Gln Lys Tyr Phe Asp Ala Cys Ala Asp Ala Val Ser Lys Asp
                180                 185                 190

Glu Leu Gln Arg Asp Lys Val Val Glu Asp Asp Glu Asp Phe Pro
            195                 200                 205

Thr Thr Arg Ser Asp Gly Asp Phe Leu His Ser Thr Asn Gly Asn Lys
210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                    245                 250                 255

Ala Thr Leu Ser His Cys Ile Glu Leu Met Val Lys Arg Glu Asp Ser
                260                 265                 270

Trp Gln Lys Arg Leu Asp Lys Glu Thr Glu Lys Lys Arg Arg Thr Glu
            275                 280                 285

Glu Ala Tyr Lys Asn Ala Met Thr Glu Leu Lys Lys Lys Ser His Phe
290                 295                 300

Gly Gly Pro Asp Tyr Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                    325                 330                 335

Glu Glu Gln Ser Gln Ser Glu Lys Val Arg Leu His Trp Pro Thr Ser
                340                 345                 350

Leu Pro Ser Gly Asp Ala Phe Ser Ser Val Gly Thr His Arg Phe Val
            355                 360                 365

Gln Lys Pro Tyr Ser Arg Ser Ser Met Ser Ser Ile Asp Leu Val
370                 375                 380

Ser Ala Ser Asp Asp Val His Arg Phe Ser Ser Gln Val Glu Glu Met
385                 390                 395                 400

Val Gln Asn His Met Thr Tyr Ser Leu Gln Asp Val Gly Gly Asp Ala
                    405                 410                 415

Asn Trp Gln Leu Val Val Glu Glu Gly Glu Met Lys Val Tyr Arg Arg
                420                 425                 430

Glu Val Glu Glu Asn Gly Ile Val Leu Asp Pro Leu Lys Ala Thr His
            435                 440                 445

Ala Val Lys Gly Val Thr Gly His Glu Val Cys Asn Tyr Phe Trp Asn
450                 455                 460

Val Asp Val Arg Asn Asp Trp Glu Thr Thr Ile Glu Asn Phe His Val
465                 470                 475                 480

Val Glu Thr Leu Ala Asp Asn Ala Ile Ile Ile Tyr Gln Thr His Lys
                    485                 490                 495

Arg Val Trp Pro Ala Ser Gln Arg Asp Val Leu Tyr Leu Ser Val Ile
                500                 505                 510

Arg Lys Ile Pro Ala Leu Thr Glu Asn Asp Pro Glu Thr Trp Ile Val
            515                 520                 525

Cys Asn Phe Ser Val Asp His Asp Ser Ala Pro Leu Asn Asn Arg Cys
530                 535                 540
```

```
Val Arg Ala Lys Ile Asn Val Ala Met Ile Cys Gln Thr Leu Val Ser
545                 550                 555                 560

Pro Pro Glu Gly Asn Gln Glu Ile Ser Arg Asp Asn Ile Leu Cys Lys
                565                 570                 575

Ile Thr Tyr Val Ala Asn Val Asn Pro Gly Gly Trp Ala Pro Ala Ser
            580                 585                 590

Val Leu Arg Ala Val Ala Lys Arg Glu Tyr Pro Lys Phe Leu Lys Arg
        595                 600                 605

Phe Thr Ser Tyr Val Gln Glu Lys Thr Ala Gly Lys Pro Ile Leu Phe
    610                 615                 620
```

<210> SEQ ID NO 2
<211> LENGTH: 25
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(10)
<223> OTHER INFORMATION: Optionally absent
<220> FEATURE:
<221> NAME/KEY: MISC_FEATURE
<222> LOCATION: (15)..(15)
<223> OTHER INFORMATION: X is E or Q
<220> FEATURE:
<221> NAME/KEY: MISC_FEATURE
<222> LOCATION: (16)..(25)
<223> OTHER INFORMATION: Optionally Absent

<400> SEQUENCE: 2

```
Ala Thr Thr Ala Gly Ile Leu Ala Thr Leu Ser His Cys Ile Xaa Leu
1               5                   10                  15

Met Val Lys Arg Glu Asp Ser Trp Gln
            20                  25
```

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

```
Ala Thr Thr Ala Gly Ile Leu Ala Thr Leu
1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

```
Leu Met Val Lys Arg Glu Asp Ser Trp Gln
1               5                   10
```

<210> SEQ ID NO 5
<211> LENGTH: 5
<212> TYPE: PRT
<213> ORGANISM: Artificial Sequence
<220> FEATURE:
<223> OTHER INFORMATION: Synthetic

<400> SEQUENCE: 5

```
Ser His Cys Ile Glu
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic

<400> SEQUENCE: 6

Ser His Cys Ile Gln
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Ile Leu Ala Thr Leu Ser His Cys Ile Glu Leu Met Val Lys Arg
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Ile Leu Ala Thr Leu Ser His Cys Ile Gln Leu Met Val Lys Arg
1               5                   10                  15

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Glu Lys Thr Ala Gly Lys Pro Ile Leu Phe
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Glu Lys Thr Ala Gly Lys Pro Ile Leu Phe
1               5                   10

<210> SEQ ID NO 11
<211> LENGTH: 19
<212> TYPE: DNA
<213> ORGANISM: Artificial Sequence
<220> FEATURE:
<223> OTHER INFORMATION: Synthetic

<400> SEQUENCE: 11
```
gccctatagt cgctcttcc                                            19

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tcctgctggt gagaaaggat                                           20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ctggagtccc ataacgacct                                           20

<210> SEQ ID NO 14
<211> LENGTH: 22
<212> TYPE: DNA
<213> ORGANISM: Artificial Sequence
<220> FEATURE:
<223> OTHER INFORMATION: Synthetic

<400> SEQUENCE: 14
gctgttgaag ctgctcttga ca                                        22

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
aagtgtctaa gtcgagggtc c                                         21

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gtaacccgtt gaacccatt                                            20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gcgatgatgg ctaacctacc                                           20

<210> SEQ ID NO 18
<211> LENGTH: 265
<212> TYPE: PRT
<213> ORGANISM: Homo sapiens

<400> SEQUENCE: 18

```
Arg Asp Glu Val Ile Gly Ile Leu Lys Ala Glu Lys Met Asp Leu Ala
1               5                   10                  15

Leu Leu Glu Ala Gln Tyr Gly Phe Val Thr Pro Lys Lys Val Leu Glu
            20                  25                  30

Ala Leu Gln Arg Asp Ala Phe Gln Ala Lys Ser Thr Pro Trp Gln Glu
        35                  40                  45

Asp Ile Tyr Glu Lys Pro Met Asn Glu Leu Asp Lys Val Val Glu Lys
    50                  55                  60

His Lys Glu Ser Tyr Arg Arg Ile Leu Gly Gln Leu Leu Val Ala Glu
65                  70                  75                  80

Lys Ser Arg Arg Gln Thr Ile Leu Glu Leu Glu Glu Glu Lys Arg Lys
                85                  90                  95

His Lys Glu Tyr Met Glu Lys Ser Asp Glu Phe Ile Cys Leu Leu Glu
            100                 105                 110

Gln Glu Cys Glu Arg Leu Lys Lys Leu Ile Asp Gln Glu Ile Lys Ser
        115                 120                 125

Gln Glu Glu Lys Glu Gln Glu Lys Glu Lys Arg Val Thr Thr Leu Lys
    130                 135                 140

Glu Glu Leu Thr Lys Leu Lys Ser Phe Ala Leu Met Val Val Asp Glu
145                 150                 155                 160

Gln Gln Arg Leu Thr Ala Gln Leu Thr Leu Gln Arg Gln Lys Ile Gln
                165                 170                 175

Glu Leu Thr Thr Asn Ala Lys Glu Thr His Thr Lys Leu Ala Leu Ala
            180                 185                 190

Glu Ala Arg Val Gln Glu Glu Gln Lys Ala Thr Arg Leu Glu Lys
        195                 200                 205

Glu Leu Gln Thr Gln Thr Thr Lys Phe His Gln Asp Gln Asp Thr Ile
    210                 215                 220

Met Ala Lys Leu Thr Asn Glu Asp Ser Gln Asn Arg Gln Leu Gln Gln
225                 230                 235                 240

Lys Leu Ala Ala Leu Ser Arg Gln Ile Asp Glu Leu Glu Glu Thr Asn
                245                 250                 255

Arg Ser Leu Arg Lys Ala Glu Glu Glu
            260                 265
```

<210> SEQ ID NO 19
<211> LENGTH: 764
<212> TYPE: PRT
<213> ORGANISM: Homo sapiens

<400> SEQUENCE: 19

```
Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95
```

```
Lys Met Asp Leu Ala Leu Leu Glu Ala Gln Tyr Gly Phe Val Thr Pro
            100                 105                 110
Lys Lys Val Leu Glu Ala Leu Gln Arg Asp Ala Phe Gln Ala Lys Ser
            115                 120                 125
Thr Pro Trp Gln Glu Asp Ile Tyr Glu Lys Pro Met Asn Glu Leu Asp
        130                 135                 140
Lys Val Val Glu Lys His Lys Glu Ser Tyr Arg Arg Ile Leu Gly Gln
145                 150                 155                 160
Leu Leu Val Ala Glu Lys Ser Arg Arg Gln Thr Ile Leu Glu Leu Glu
                165                 170                 175
Glu Glu Lys Arg Lys His Lys Glu Tyr Met Glu Lys Ser Asp Glu Phe
            180                 185                 190
Ile Cys Leu Leu Glu Gln Glu Cys Glu Arg Leu Lys Lys Leu Ile Asp
        195                 200                 205
Gln Glu Ile Lys Ser Gln Glu Glu Lys Glu Gln Glu Lys Glu Lys Arg
    210                 215                 220
Val Thr Thr Leu Lys Glu Glu Leu Thr Lys Leu Lys Ser Phe Ala Leu
225                 230                 235                 240
Met Val Val Asp Glu Gln Gln Arg Leu Thr Ala Gln Leu Thr Leu Gln
                245                 250                 255
Arg Gln Lys Ile Gln Glu Leu Thr Thr Asn Ala Lys Glu Thr His Thr
            260                 265                 270
Lys Leu Ala Leu Ala Glu Ala Arg Val Gln Glu Glu Glu Gln Lys Ala
        275                 280                 285
Thr Arg Leu Glu Lys Glu Leu Gln Thr Gln Thr Lys Phe His Gln
    290                 295                 300
Asp Gln Asp Thr Ile Met Ala Lys Leu Thr Asn Glu Asp Ser Gln Asn
305                 310                 315                 320
Arg Gln Leu Gln Gln Lys Leu Ala Ala Leu Ser Arg Gln Ile Asp Glu
                325                 330                 335
Leu Glu Glu Thr Asn Arg Ser Leu Arg Lys Ala Glu Glu Glu Leu Gln
            340                 345                 350
Asp Ile Lys Glu Lys Ile Ser Lys Gly Glu Tyr Gly Asn Ala Gly Ile
        355                 360                 365
Met Ala Glu Val Glu Glu Leu Arg Lys Arg Val Leu Asp Met Glu Gly
    370                 375                 380
Lys Asp Glu Glu Leu Ile Lys Met Glu Glu Gln Cys Arg Asp Leu Asn
385                 390                 395                 400
Lys Arg Leu Glu Arg Glu Thr Leu Gln Ser Lys Asp Phe Lys Leu Glu
                405                 410                 415
Val Glu Lys Leu Ser Lys Arg Ile Met Ala Leu Glu Lys Leu Glu Asp
            420                 425                 430
Ala Phe Asn Lys Ser Lys Gln Glu Cys Tyr Ser Leu Lys Cys Asn Leu
        435                 440                 445
Glu Lys Glu Arg Met Thr Thr Lys Gln Leu Ser Gln Glu Leu Glu Ser
    450                 455                 460
Leu Lys Val Arg Ile Lys Glu Leu Glu Ala Ile Glu Ser Arg Leu Glu
465                 470                 475                 480
Lys Thr Glu Phe Thr Leu Lys Glu Asp Leu Thr Lys Leu Lys Thr Leu
                485                 490                 495
Thr Val Met Phe Val Asp Glu Arg Lys Thr Met Ser Glu Lys Leu Lys
            500                 505                 510
```

```
Lys Thr Glu Asp Lys Leu Gln Ala Ser Ser Gln Leu Gln Val Glu
            515                 520                 525

Gln Asn Lys Val Thr Thr Val Thr Glu Lys Leu Ile Glu Glu Thr Lys
530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
                580                 585                 590

Gln Ser Leu Glu Ala Ile Glu Lys Asp Phe Leu Lys Asn Lys Leu Asn
        595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Leu Met Lys Thr Glu Asp Glu Tyr
                645                 650                 655

Glu Thr Leu Glu Arg Arg Tyr Ala Asn Glu Arg Asp Lys Ala Gln Phe
                660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Thr Lys Ser
                740                 745                 750

Thr Arg Lys Gln Glu Gln Arg Phe Arg Lys Arg Asp
        755                 760

<210> SEQ ID NO 20
<211> LENGTH: 1135
<212> TYPE: PRT
<213> ORGANISM: Homo sapiens

<400> SEQUENCE: 20

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125
```

```
Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Gln Lys Ala
        275                 280                 285

Thr Arg Leu Glu Lys Glu Leu Gln Thr Gln Thr Thr Lys Phe His Gln
290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335

Leu Glu Glu Thr Asn Arg Ser Leu Arg Lys Ala Glu Glu Glu Leu Gln
            340                 345                 350

Asp Ile Lys Glu Lys Ile Ser Lys Gly Glu Tyr Gly Asn Ala Gly Ile
        355                 360                 365

Met Ala Glu Val Glu Glu Leu Arg Lys Arg Val Leu Asp Met Glu Gly
370                 375                 380

Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
                405                 410                 415

Val Glu Lys Leu Ser Lys Arg Ile Met Ala Leu Glu Lys Leu Glu Asp
            420                 425                 430

Ala Phe Asn Lys Ser Lys Gln Glu Cys Tyr Ser Leu Lys Cys Asn Leu
        435                 440                 445

Glu Lys Glu Arg Met Thr Thr Lys Gln Leu Ser Gln Glu Leu Glu Ser
450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
530                 535                 540
```

-continued

```
Arg Ala Leu Lys Ser Lys Thr Asp Val Glu Lys Met Tyr Ser Val
545                 550                 555                 560

Thr Lys Glu Arg Asp Asp Leu Lys Asn Lys Leu Lys Ala Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
    595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Leu Met Lys Thr Glu Asp Glu Tyr
                645                 650                 655

Glu Thr Leu Glu Arg Arg Tyr Ala Asn Glu Arg Asp Lys Ala Gln Phe
                660                 665                 670

Leu Ser Lys Glu Leu Glu His Val Lys Met Glu Leu Ala Lys Tyr Lys
    675                 680                 685

Leu Ala Glu Lys Thr Glu Thr Ser His Glu Gln Trp Leu Phe Lys Arg
    690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
                740                 745                 750

Gln Glu Asn Arg Asn Arg Asp Leu Gly Arg Glu Ile Glu Asn Leu Thr
    755                 760                 765

Lys Glu Leu Glu Arg Tyr Arg His Phe Ser Lys Ser Leu Arg Pro Ser
    770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Pro Asp Tyr Lys Ser Leu Ile
                805                 810                 815

Pro Leu Glu Arg Ala Val Ile Asn Gly Gln Leu Tyr Glu Glu Ser Glu
                820                 825                 830

Asn Gln Asp Glu Asp Pro Asn Asp Glu Gly Ser Val Leu Ser Phe Lys
    835                 840                 845

Cys Ser Gln Ser Thr Pro Cys Pro Val Asn Arg Lys Leu Trp Ile Pro
850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
                900                 905                 910

Asn Thr Ala Thr Leu Glu Ile Thr Ser Pro Thr Thr Glu Ser Pro His
    915                 920                 925

Ser Tyr Thr Ser Thr Ala Val Ile Pro Asn Cys Gly Thr Pro Lys Gln
    930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
```

965                 970                 975
Thr Met Ala Thr Phe Arg Ala Gln Thr Pro Glu Ser Cys Gly Ser
            980                 985                 990
Leu Thr Pro Glu Arg Thr Met Ser Pro Ile Gln Val Leu Ala Val Thr
            995                 1000                1005
Gly Ser Ala Ser Pro Glu Gln Gly Arg Ser Pro Glu Pro Thr
            1010                1015                1020
Glu Ile Ser Ala Lys His Ala Ile Phe Arg Val Ser Pro Asp Arg
            1025                1030                1035
Gln Ser Ser Trp Gln Phe Gln Arg Ser Asn Ser Asn Ser Ser Ser
            1040                1045                1050
Val Ile Thr Thr Glu Asp Asn Lys Ile His Ile His Leu Gly Ser
            1055                1060                1065
Pro Tyr Met Gln Ala Val Ala Ser Pro Val Arg Pro Ala Ser Pro
            1070                1075                1080
Ser Ala Pro Leu Gln Asp Asn Arg Thr Gln Gly Leu Ile Asn Gly
            1085                1090                1095
Ala Leu Asn Lys Thr Thr Asn Lys Val Thr Ser Ser Ile Thr Ile
            1100                1105                1110
Thr Pro Thr Ala Thr Pro Leu Pro Arg Gln Ser Gln Ile Thr Val
            1115                1120                1125
Glu Pro Leu Leu Leu Pro His
            1130                1135

<210> SEQ ID NO 21
<211> LENGTH: 1133
<212> TYPE: PRT
<213> ORGANISM: Homo sapiens

<400> SEQUENCE: 21

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
                20                  25                  30

His Arg Gln Gln Asp Lys Asp Ser Pro Ser Glu Ser Asp Val Ile Leu
            35                  40                  45

Pro Cys Pro Lys Ala Glu Lys Pro His Ser Gly Asn Gly His Gln Ala
        50                  55                  60

Glu Asp Leu Ser Arg Asp Asp Leu Phe Leu Leu Ser Ile Leu Glu
65                  70                  75              80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155             160

Leu Leu Val Ala Glu Lys Ser His Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

```
Ile Cys Leu Leu Glu Gln Glu Cys Glu Arg Leu Lys Lys Leu Ile Asp
        195                 200                 205
Gln Glu Ile Lys Ser Gln Glu Lys Glu Gln Glu Lys Glu Lys Arg
    210                 215                 220
Val Thr Thr Leu Lys Glu Glu Leu Thr Lys Leu Lys Ser Phe Ala Leu
225                 230                 235                 240
Met Val Val Asp Glu Gln Gln Arg Leu Thr Ala Gln Leu Thr Leu Gln
                245                 250                 255
Arg Gln Lys Ile Gln Glu Leu Thr Thr Asn Ala Lys Glu Thr His Thr
            260                 265                 270
Lys Leu Ala Leu Ala Glu Ala Arg Val Gln Glu Glu Gln Lys Ala
        275                 280                 285
Thr Arg Leu Glu Lys Glu Leu Gln Thr Gln Thr Thr Lys Phe His Gln
    290                 295                 300
Asp Gln Asp Thr Ile Met Ala Lys Leu Thr Asn Glu Asp Ser Gln Asn
305                 310                 315                 320
Arg Gln Leu Gln Gln Lys Leu Ala Ala Leu Ser Arg Gln Ile Asp Glu
                325                 330                 335
Leu Glu Glu Thr Asn Arg Ser Leu Arg Lys Ala Glu Glu Glu Leu Gln
            340                 345                 350
Asp Ile Lys Glu Lys Ile Ser Lys Gly Glu Tyr Gly Asn Ala Gly Ile
        355                 360                 365
Met Ala Glu Val Glu Glu Leu Arg Lys Arg Val Leu Asp Met Glu Gly
    370                 375                 380
Lys Asp Glu Glu Leu Ile Lys Met Glu Glu Gln Cys Arg Asp Leu Asn
385                 390                 395                 400
Lys Arg Leu Glu Arg Glu Thr Leu Gln Ser Lys Asp Phe Lys Leu Glu
                405                 410                 415
Val Glu Lys Leu Ser Lys Arg Ile Met Ala Leu Glu Lys Leu Glu Asp
            420                 425                 430
Ala Phe Asn Lys Ser Lys Gln Glu Cys Tyr Ser Leu Lys Cys Asn Leu
        435                 440                 445
Glu Lys Glu Arg Met Thr Thr Lys Gln Leu Ser Gln Glu Leu Glu Ser
    450                 455                 460
Leu Lys Val Arg Ile Lys Glu Leu Glu Ala Ile Glu Ser Arg Leu Glu
465                 470                 475                 480
Lys Thr Glu Phe Thr Leu Lys Glu Asp Leu Thr Lys Leu Lys Thr Leu
                485                 490                 495
Thr Val Met Phe Val Asp Glu Arg Lys Thr Met Ser Glu Lys Leu Lys
            500                 505                 510
Lys Thr Glu Asp Lys Leu Gln Ala Ala Ser Ser Gln Leu Gln Val Glu
        515                 520                 525
Gln Asn Lys Val Thr Thr Val Thr Glu Lys Leu Ile Glu Glu Thr Lys
    530                 535                 540
Arg Ala Leu Lys Ser Lys Thr Asp Val Glu Glu Lys Met Tyr Ser Val
545                 550                 555                 560
Thr Lys Glu Arg Asp Asp Leu Lys Asn Lys Leu Lys Ala Glu Glu
                565                 570                 575
Lys Gly Asn Asp Leu Leu Ser Arg Val Asn Met Leu Lys Asn Arg Leu
            580                 585                 590
Gln Ser Leu Glu Ala Ile Glu Lys Asp Phe Leu Lys Asn Lys Leu Asn
        595                 600                 605
Gln Asp Ser Gly Lys Ser Thr Thr Ala Leu His Gln Glu Asn Asn Lys
```

```
                610             615             620
Ile Lys Glu Leu Ser Gln Glu Val Glu Arg Leu Lys Leu Lys Leu Lys
625             630             635             640

Asp Met Lys Ala Ile Glu Asp Leu Met Lys Thr Glu Asp Glu Tyr
            645             650             655

Glu Thr Leu Glu Arg Arg Tyr Ala Asn Glu Arg Asp Lys Ala Gln Phe
            660             665             670

Leu Ser Lys Glu Leu His Val Lys Met Glu Leu Ala Lys Tyr Lys
            675             680             685

Leu Ala Glu Lys Thr Glu Thr Ser His Glu Gln Trp Leu Phe Lys Arg
690             695             700

Leu Gln Glu Glu Glu Ala Lys Ser Gly His Leu Ser Arg Glu Val Asp
705             710             715             720

Ala Leu Lys Glu Lys Ile His Glu Tyr Met Ala Thr Glu Asp Leu Ile
            725             730             735

Cys His Leu Gln Gly Asp His Ser Val Leu Gln Lys Lys Leu Asn Gln
            740             745             750

Gln Glu Asn Arg Asn Arg Asp Leu Gly Arg Glu Ile Glu Asn Leu Thr
            755             760             765

Lys Glu Leu Glu Arg Tyr Arg His Phe Ser Lys Ser Leu Arg Pro Ser
770             775             780

Leu Asn Gly Arg Arg Ile Ser Asp Pro Gln Val Phe Ser Lys Glu Val
785             790             795             800

Gln Thr Glu Ala Val Asp Asn Glu Pro Pro Asp Tyr Lys Ser Leu Ile
            805             810             815

Pro Leu Glu Arg Ala Val Ile Asn Gly Gln Leu Tyr Glu Glu Ser Glu
            820             825             830

Asn Gln Asp Glu Asp Pro Asn Asp Glu Gly Ser Val Leu Ser Phe Lys
            835             840             845

Cys Ser Gln Ser Thr Pro Cys Pro Val Asn Arg Lys Leu Trp Ile Pro
            850             855             860

Trp Met Lys Ser Lys Glu Gly His Leu Gln Asn Gly Lys Met Gln Thr
865             870             875             880

Lys Pro Asn Ala Asn Phe Val Gln Pro Gly Asp Leu Val Leu Ser His
            885             890             895

Thr Pro Gly Gln Pro Leu His Ile Lys Val Thr Pro Asp His Val Gln
            900             905             910

Asn Thr Ala Thr Leu Glu Ile Thr Ser Pro Thr Thr Glu Ser Pro His
            915             920             925

Ser Tyr Thr Ser Thr Ala Val Ile Pro Asn Cys Gly Thr Pro Lys Gln
            930             935             940

Arg Ile Thr Ile Leu Gln Asn Ala Ser Ile Thr Pro Val Lys Ser Lys
945             950             955             960

Thr Ser Thr Glu Asp Leu Met Asn Leu Glu Gln Gly Met Ser Pro Ile
            965             970             975

Thr Met Ala Thr Phe Ala Arg Ala Gln Thr Pro Glu Ser Cys Gly Ser
            980             985             990

Leu Thr Pro Glu Arg Thr Met Ser  Pro Ile Gln Val Leu  Ala Val Thr
            995             1000              1005

Gly Ser  Ala Ser Ser Pro Glu  Gln Gly Arg Ser Pro  Glu Pro Thr
            1010              1015              1020

Glu Ile  Ser Ala Lys His Ala  Ile Phe Arg Val Ser  Pro Asp Arg
            1025              1030              1035
```

```
Gln Ser Ser Trp Gln Phe Gln Arg Ser Asn Ser Asn Ser Ser Ser
    1040                1045                1050

Val Ile Thr Thr Glu Asp Asn Lys Ile His Ile His Leu Gly Ser
    1055                1060                1065

Pro Tyr Met Gln Ala Val Ala Ser Pro Val Arg Pro Ala Ser Pro
    1070                1075                1080

Ser Ala Pro Leu Gln Asp Asn Arg Thr Gln Gly Leu Ile Asn Gly
    1085                1090                1095

Ala Leu Asn Lys Thr Thr Asn Lys Val Thr Ser Ser Ile Thr Ile
    1100                1105                1110

Thr Pro Thr Ala Thr Pro Leu Pro Arg Gln Ser Gln Ile Thr Val
    1115                1120                1125

Ser Asn Ile Tyr Asn
    1130

<210> SEQ ID NO 22
<211> LENGTH: 1133
<212> TYPE: PRT
<213> ORGANISM: Homo sapiens

<400> SEQUENCE: 22

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
                20                  25                  30

His Arg Gln Gln Asp Lys Asp Ser Pro Ser Glu Ser Asp Val Ile Leu
            35                  40                  45

Pro Cys Pro Lys Ala Glu Lys Pro His Ser Gly Asn Gly His Gln Ala
        50                  55                  60

Glu Asp Leu Ser Arg Asp Asp Leu Leu Phe Leu Leu Ser Ile Leu Glu
65              70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
                100                 105                 110

Lys Lys Val Leu Glu Ala Leu Gln Arg Asp Ala Phe Gln Ala Lys Ser
            115                 120                 125

Thr Pro Trp Gln Glu Asp Ile Tyr Glu Lys Pro Met Asn Glu Leu Asp
        130                 135                 140

Lys Val Val Glu Lys His Lys Glu Ser Tyr Arg Arg Ile Leu Gly Gln
145             150                 155                 160

Leu Leu Val Ala Glu Lys Ser Arg Arg Gln Thr Ile Leu Glu Leu Glu
                165                 170                 175

Glu Glu Lys Arg Lys His Lys Glu Tyr Met Glu Lys Ser Asp Glu Phe
                180                 185                 190

Ile Cys Leu Leu Glu Gln Glu Cys Glu Arg Leu Lys Lys Leu Ile Asp
            195                 200                 205

Gln Glu Ile Lys Ser Gln Glu Glu Lys Glu Gln Glu Lys Glu Lys Arg
        210                 215                 220

Val Thr Thr Leu Lys Glu Glu Leu Thr Lys Leu Lys Ser Phe Ala Leu
225             230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
```

```
                260             265             270
Lys Leu Ala Leu Ala Glu Ala Arg Val Gln Glu Glu Gln Lys Ala
            275             280             285
Thr Arg Leu Glu Lys Glu Leu Gln Thr Gln Thr Thr Lys Phe His Gln
        290             295             300
Asp Gln Asp Thr Ile Met Ala Lys Leu Thr Asn Glu Asp Ser Gln Asn
305             310             315             320
Arg Gln Leu Gln Gln Lys Leu Ala Ala Leu Ser Arg Gln Ile Asp Glu
                325             330             335
Leu Glu Glu Thr Asn Arg Ser Leu Arg Lys Ala Glu Glu Leu Gln
            340             345             350
Asp Ile Lys Glu Lys Ile Ser Lys Gly Glu Tyr Gly Asn Ala Gly Ile
        355             360             365
Met Ala Glu Val Glu Glu Leu Arg Lys Arg Val Leu Asp Met Glu Gly
    370             375             380
Lys Asp Glu Glu Leu Ile Lys Met Glu Glu Gln Cys Arg Asp Leu Asn
385             390             395             400
Lys Arg Leu Glu Arg Glu Thr Leu Gln Ser Lys Asp Phe Lys Leu Glu
                405             410             415
Val Glu Lys Leu Ser Lys Arg Ile Met Ala Leu Glu Lys Leu Glu Asp
            420             425             430
Ala Phe Asn Lys Ser Lys Gln Glu Cys Tyr Ser Leu Lys Cys Asn Leu
        435             440             445
Glu Lys Glu Arg Met Thr Thr Lys Gln Leu Ser Gln Glu Leu Glu Ser
    450             455             460
Leu Lys Val Arg Ile Lys Glu Leu Glu Ala Ile Glu Ser Arg Leu Glu
465             470             475             480
Lys Thr Glu Phe Thr Leu Lys Glu Asp Leu Thr Lys Leu Lys Thr Leu
                485             490             495
Thr Val Met Phe Val Asp Glu Arg Lys Thr Met Ser Glu Lys Leu Lys
            500             505             510
Lys Thr Glu Asp Lys Leu Gln Ala Ala Ser Ser Gln Leu Gln Val Glu
        515             520             525
Gln Asn Lys Val Thr Thr Val Thr Glu Lys Leu Ile Glu Glu Thr Lys
    530             535             540
Arg Ala Leu Lys Ser Lys Thr Asp Val Glu Glu Lys Met Tyr Ser Val
545             550             555             560
Thr Lys Glu Arg Asp Asp Leu Lys Asn Lys Leu Lys Ala Glu Glu Glu
                565             570             575
Lys Gly Asn Asp Leu Leu Ser Arg Val Asn Met Leu Lys Asn Arg Leu
            580             585             590
Gln Ser Leu Glu Ala Ile Glu Lys Asp Phe Leu Lys Asn Lys Leu Asn
        595             600             605
Gln Asp Ser Gly Lys Ser Thr Thr Ala Leu His Gln Glu Asn Asn Lys
    610             615             620
Ile Lys Glu Leu Ser Gln Glu Val Glu Arg Leu Lys Leu Lys Leu Lys
625             630             635             640
Asp Met Lys Ala Ile Glu Asp Asp Leu Met Lys Thr Glu Asp Glu Tyr
                645             650             655
Glu Thr Leu Glu Arg Arg Tyr Ala Asn Glu Arg Asp Lys Ala Gln Phe
            660             665             670
Leu Ser Lys Glu Leu Glu His Val Lys Met Glu Leu Ala Lys Tyr Lys
        675             680             685
```

```
Leu Ala Glu Lys Thr Glu Thr Ser His Glu Gln Trp Leu Phe Lys Arg
690                 695                 700
Leu Gln Glu Glu Glu Ala Lys Ser Gly His Leu Ser Arg Glu Val Asp
705                 710                 715                 720
Ala Leu Lys Glu Lys Ile His Glu Tyr Met Ala Thr Glu Asp Leu Ile
                725                 730                 735
Cys His Leu Gln Gly Asp His Ser Val Leu Gln Lys Lys Leu Asn Gln
                740                 745                 750
Gln Glu Asn Arg Asn Arg Asp Leu Gly Arg Glu Ile Glu Asn Leu Thr
                755                 760                 765
Lys Glu Leu Glu Arg Tyr Arg His Phe Ser Lys Ser Leu Arg Pro Ser
770                 775                 780
Leu Asn Gly Arg Arg Ile Ser Asp Pro Gln Val Phe Ser Lys Glu Val
785                 790                 795                 800
Gln Thr Glu Ala Val Asp Asn Glu Pro Asp Tyr Lys Ser Leu Ile
                805                 810                 815
Pro Leu Glu Arg Ala Val Ile Asn Gly Gln Leu Tyr Glu Glu Ser Glu
                820                 825                 830
Asn Gln Asp Glu Asp Pro Asn Asp Glu Gly Ser Val Leu Ser Phe Lys
                835                 840                 845
Cys Ser Gln Ser Thr Pro Cys Pro Val Asn Arg Lys Leu Trp Ile Pro
                850                 855                 860
Trp Met Lys Ser Lys Glu Gly His Leu Gln Asn Gly Lys Met Gln Thr
865                 870                 875                 880
Lys Pro Asn Ala Asn Phe Val Gln Pro Gly Asp Leu Val Leu Ser His
                885                 890                 895
Thr Pro Gly Gln Pro Leu His Ile Lys Val Thr Pro Asp His Val Gln
                900                 905                 910
Asn Thr Ala Thr Leu Glu Ile Thr Ser Pro Thr Thr Glu Ser Pro His
                915                 920                 925
Ser Tyr Thr Ser Thr Ala Val Ile Pro Asn Cys Gly Thr Pro Lys Gln
                930                 935                 940
Arg Ile Thr Ile Leu Gln Asn Ala Ser Ile Thr Pro Val Lys Ser Lys
945                 950                 955                 960
Thr Ser Thr Glu Asp Leu Met Asn Leu Glu Gln Gly Met Ser Pro Ile
                965                 970                 975
Thr Met Ala Thr Phe Ala Arg Ala Gln Thr Pro Glu Ser Cys Gly Ser
                980                 985                 990
Leu Thr Pro Glu Arg Thr Met Ser Pro Ile Gln Val Leu Ala Val Thr
                995                 1000                1005
Gly Ser Ala Ser Ser Pro Glu Gln Gly Arg Ser Pro Glu Pro Thr
1010                1015                1020
Glu Ile Ser Ala Lys His Ala Ile Phe Arg Val Ser Pro Asp Arg
1025                1030                1035
Gln Ser Ser Trp Gln Phe Gln Arg Ser Asn Ser Asn Ser Ser Ser
1040                1045                1050
Val Ile Thr Thr Glu Asp Asn Lys Ile His Ile His Leu Gly Ser
1055                1060                1065
Pro Tyr Met Gln Ala Val Ala Ser Pro Val Arg Pro Ala Ser Pro
1070                1075                1080
Ser Ala Pro Leu Gln Asp Asn Arg Thr Gln Gly Leu Ile Asn Gly
1085                1090                1095
```

```
Ala Leu Asn Lys Thr Thr Asn Lys Val Thr Ser Ser Ile Thr Ile
    1100                1105                1110

Thr Pro Thr Ala Thr Pro Leu Pro Arg Gln Ser Gln Ile Thr Val
    1115                1120                1125

Ser Asn Ile Tyr Asn
    1130

<210> SEQ ID NO 23
<211> LENGTH: 1135
<212> TYPE: PRT
<213> ORGANISM: Homo sapiens

<400> SEQUENCE: 23

Met Arg Ser Arg Gly Ser Asp Thr Glu Gly Ser Ala Gln Lys Lys Phe
1               5                   10                  15

Pro Arg His Thr Lys Gly His Ser Phe Gln Gly Pro Lys Asn Met Lys
            20                  25                  30

His Arg Gln Gln Asp Lys Asp Ser Pro Ser Glu Ser Asp Val Ile Leu
        35                  40                  45

Pro Cys Pro Lys Ala Glu Lys Pro His Ser Gly Asn Gly His Gln Ala
    50                  55                  60

Glu Asp Leu Ser Arg Asp Asp Leu Leu Phe Leu Leu Ser Ile Leu Glu
65                  70                  75                  80

Gly Glu Leu Gln Ala Arg Asp Glu Val Ile Gly Ile Leu Lys Ala Glu
                85                  90                  95

Lys Met Asp Leu Ala Leu Leu Glu Ala Gln Tyr Gly Phe Val Thr Pro
            100                 105                 110

Lys Lys Val Leu Glu Ala Leu Gln Arg Asp Ala Phe Gln Ala Lys Ser
        115                 120                 125

Thr Pro Trp Gln Glu Asp Ile Tyr Glu Lys Pro Met Asn Glu Leu Asp
    130                 135                 140

Lys Val Val Glu Lys His Lys Glu Ser Tyr Arg Arg Ile Leu Gly Gln
145                 150                 155                 160

Leu Leu Val Ala Glu Lys Ser His Arg Gln Thr Ile Leu Glu Leu Glu
                165                 170                 175

Glu Glu Lys Arg Lys His Lys Glu Tyr Met Glu Lys Ser Asp Glu Phe
            180                 185                 190

Ile Cys Leu Leu Glu Gln Glu Cys Glu Arg Leu Lys Lys Leu Ile Asp
        195                 200                 205

Gln Glu Ile Lys Ser Gln Glu Glu Lys Glu Gln Glu Lys Glu Lys Arg
    210                 215                 220

Val Thr Thr Leu Lys Glu Glu Leu Thr Lys Leu Lys Ser Phe Ala Leu
225                 230                 235                 240

Met Val Val Asp Glu Gln Gln Arg Leu Thr Ala Gln Leu Thr Leu Gln
                245                 250                 255

Arg Gln Lys Ile Gln Glu Leu Thr Thr Asn Ala Lys Glu Thr His Thr
            260                 265                 270

Lys Leu Ala Leu Ala Glu Ala Arg Val Gln Glu Glu Gln Lys Ala
        275                 280                 285

Thr Arg Leu Glu Lys Glu Leu Gln Thr Gln Thr Thr Lys Phe His Gln
    290                 295                 300

Asp Gln Asp Thr Ile Met Ala Lys Leu Thr Asn Glu Asp Ser Gln Asn
305                 310                 315                 320

Arg Gln Leu Gln Gln Lys Leu Ala Ala Leu Ser Arg Gln Ile Asp Glu
                325                 330                 335
```

```
Leu Glu Glu Thr Asn Arg Ser Leu Arg Lys Ala Glu Glu Leu Gln
            340                 345                 350

Asp Ile Lys Glu Lys Ile Ser Lys Gly Glu Tyr Gly Asn Ala Gly Ile
        355                 360                 365

Met Ala Glu Val Glu Glu Leu Arg Lys Arg Val Leu Asp Met Glu Gly
    370                 375                 380

Lys Asp Glu Glu Leu Ile Lys Met Glu Glu Gln Cys Arg Asp Leu Asn
385                 390                 395                 400

Lys Arg Leu Glu Arg Glu Thr Leu Gln Ser Lys Asp Phe Lys Leu Glu
                405                 410                 415

Val Glu Lys Leu Ser Lys Arg Ile Met Ala Leu Glu Lys Leu Glu Asp
            420                 425                 430

Ala Phe Asn Lys Ser Lys Gln Glu Cys Tyr Ser Leu Lys Cys Asn Leu
        435                 440                 445

Glu Lys Glu Arg Met Thr Thr Lys Gln Leu Ser Gln Glu Leu Glu Ser
        450                 455                 460

Leu Lys Val Arg Ile Lys Glu Leu Glu Ala Ile Glu Ser Arg Leu Glu
465                 470                 475                 480

Lys Thr Glu Phe Thr Leu Lys Glu Asp Leu Thr Lys Leu Lys Thr Leu
                485                 490                 495

Thr Val Met Phe Val Asp Glu Arg Lys Thr Met Ser Glu Lys Leu Lys
            500                 505                 510

Lys Thr Glu Asp Lys Leu Gln Ala Ala Ser Ser Gln Leu Gln Val Glu
        515                 520                 525

Gln Asn Lys Val Thr Thr Val Thr Glu Lys Leu Ile Glu Glu Thr Lys
    530                 535                 540

Arg Ala Leu Lys Ser Lys Thr Asp Val Glu Glu Lys Met Tyr Ser Val
545                 550                 555                 560

Thr Lys Glu Arg Asp Asp Leu Lys Asn Lys Leu Lys Ala Glu Glu Glu
                565                 570                 575

Lys Gly Asn Asp Leu Leu Ser Arg Val Asn Met Leu Lys Asn Arg Leu
            580                 585                 590

Gln Ser Leu Glu Ala Ile Glu Lys Asp Phe Leu Lys Asn Lys Leu Asn
        595                 600                 605

Gln Asp Ser Gly Lys Ser Thr Thr Ala Leu His Gln Glu Asn Asn Lys
    610                 615                 620

Ile Lys Glu Leu Ser Gln Glu Val Glu Arg Leu Lys Leu Lys Leu Lys
625                 630                 635                 640

Asp Met Lys Ala Ile Glu Asp Asp Leu Met Lys Thr Glu Asp Glu Tyr
                645                 650                 655

Glu Thr Leu Glu Arg Arg Tyr Ala Asn Glu Arg Asp Lys Ala Gln Phe
            660                 665                 670

Leu Ser Lys Glu Leu Glu His Val Lys Met Glu Leu Ala Lys Tyr Lys
        675                 680                 685

Leu Ala Glu Lys Thr Glu Thr Ser His Glu Gln Trp Leu Phe Lys Arg
        690                 695                 700

Leu Gln Glu Glu Glu Ala Lys Ser Gly His Leu Ser Arg Glu Val Asp
705                 710                 715                 720

Ala Leu Lys Glu Lys Ile His Glu Tyr Met Ala Thr Glu Asp Leu Ile
                725                 730                 735

Cys His Leu Gln Gly Asp His Ser Val Leu Gln Lys Lys Leu Asn Gln
            740                 745                 750
```

Gln Glu Asn Arg Asn Arg Asp Leu Gly Arg Glu Ile Glu Asn Leu Thr
            755                 760                 765

Lys Glu Leu Glu Arg Tyr Arg His Phe Ser Lys Ser Leu Arg Pro Ser
770                 775                 780

Leu Asn Gly Arg Arg Ile Ser Asp Pro Gln Val Phe Ser Lys Glu Val
785                 790                 795                 800

Gln Thr Glu Ala Val Asp Asn Glu Pro Pro Asp Tyr Lys Ser Leu Ile
                805                 810                 815

Pro Leu Glu Arg Ala Val Ile Asn Gly Gln Leu Tyr Glu Glu Ser Glu
                820                 825                 830

Asn Gln Asp Glu Asp Pro Asn Asp Glu Gly Ser Val Leu Ser Phe Lys
                835                 840                 845

Cys Ser Gln Ser Thr Pro Cys Pro Val Asn Arg Lys Leu Trp Ile Pro
850                 855                 860

Trp Met Lys Ser Lys Glu Gly His Leu Gln Asn Gly Lys Met Gln Thr
865                 870                 875                 880

Lys Pro Asn Ala Asn Phe Val Gln Pro Gly Asp Leu Val Leu Ser His
                885                 890                 895

Thr Pro Gly Gln Pro Leu His Ile Lys Val Thr Pro Asp His Val Gln
                900                 905                 910

Asn Thr Ala Thr Leu Glu Ile Thr Ser Pro Thr Thr Glu Ser Pro His
                915                 920                 925

Ser Tyr Thr Ser Thr Ala Val Ile Pro Asn Cys Gly Thr Pro Lys Gln
                930                 935                 940

Arg Ile Thr Ile Leu Gln Asn Ala Ser Ile Thr Pro Val Lys Ser Lys
945                 950                 955                 960

Thr Ser Thr Glu Asp Leu Met Asn Leu Glu Gln Gly Met Ser Pro Ile
                965                 970                 975

Thr Met Ala Thr Phe Ala Arg Ala Gln Thr Pro Glu Ser Cys Gly Ser
                980                 985                 990

Leu Thr Pro Glu Arg Thr Met Ser Pro Ile Gln Val Leu Ala Val Thr
                995                 1000                1005

Gly Ser Ala Ser Ser Pro Glu Gln Gly Arg Ser Pro Glu Pro Thr
        1010                1015                1020

Glu Ile Ser Ala Lys His Ala Ile Phe Arg Val Ser Pro Asp Arg
        1025                1030                1035

Gln Ser Ser Trp Gln Phe Gln Arg Ser Asn Ser Asn Ser Ser Ser
        1040                1045                1050

Val Ile Thr Thr Glu Asp Asn Lys Ile His Ile His Leu Gly Ser
        1055                1060                1065

Pro Tyr Met Gln Ala Val Ala Ser Pro Val Arg Pro Ala Ser Pro
        1070                1075                1080

Ser Ala Pro Leu Gln Asp Asn Arg Thr Gln Gly Leu Ile Asn Gly
        1085                1090                1095

Ala Leu Asn Lys Thr Thr Asn Lys Val Thr Ser Ser Ile Thr Ile
        1100                1105                1110

Thr Pro Thr Ala Thr Pro Leu Pro Arg Gln Ser Gln Ile Thr Val
        1115                1120                1125

Glu Pro Leu Leu Leu Pro His
        1130                1135

<210> SEQ ID NO 24
<211> LENGTH: 197
<212> TYPE: PRT

<213> ORGANISM: Homo sapiens

<400> SEQUENCE: 24

```
Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
            20                  25                  30
His Arg Asp Thr Gly Ile Leu Asp Ser Ile Gly Arg Phe Phe Gly Gly
        35                  40                  45
Asp Arg Gly Ala Pro Lys Arg Gly Ser Gly Lys Val Pro Trp Leu Lys
    50                  55                  60
Pro Gly Arg Ser Pro Leu Pro Ser His Ala Arg Ser Gln Pro Gly Leu
65                  70                  75                  80
Cys Asn Met Tyr Lys Asp Ser His His Pro Ala Arg Thr Ala His Tyr
                85                  90                  95
Gly Ser Leu Pro Gln Lys Ser His Gly Arg Thr Gln Asp Glu Asn Pro
            100                 105                 110
Val Val His Phe Phe Lys Asn Ile Val Thr Pro Arg Thr Pro Pro Pro
        115                 120                 125
Ser Gln Gly Lys Gly Arg Gly Leu Ser Leu Ser Arg Phe Ser Trp Gly
    130                 135                 140
Ala Glu Gly Gln Arg Pro Gly Phe Gly Tyr Gly Gly Arg Ala Ser Asp
145                 150                 155                 160
Tyr Lys Ser Ala His Lys Gly Phe Lys Gly Val Asp Ala Gln Gly Thr
                165                 170                 175
Leu Ser Lys Ile Phe Lys Leu Gly Gly Arg Asp Ser Arg Ser Gly Ser
            180                 185                 190
Pro Met Ala Arg Arg
            195
```

<210> SEQ ID NO 25
<211> LENGTH: 186
<212> TYPE: PRT
<213> ORGANISM: Homo sapiens

<400> SEQUENCE: 25

```
Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
            20                  25                  30
His Arg Asp Thr Gly Ile Leu Asp Ser Ile Gly Arg Phe Phe Gly Gly
        35                  40                  45
Asp Arg Gly Ala Pro Lys Arg Gly Ser Gly Lys Val Pro Trp Leu Lys
    50                  55                  60
Pro Gly Arg Ser Pro Leu Pro Ser His Ala Arg Ser Gln Pro Gly Leu
65                  70                  75                  80
Cys Asn Met Tyr Lys Asp Ser His His Pro Ala Arg Thr Ala His Tyr
                85                  90                  95
Gly Ser Leu Pro Gln Lys Ser His Gly Arg Thr Gln Asp Glu Asn Pro
            100                 105                 110
Val Val His Phe Phe Lys Asn Ile Val Thr Pro Arg Thr Pro Pro Pro
        115                 120                 125
Ser Gln Gly Lys Gly Ala Glu Gly Gln Arg Pro Gly Phe Gly Tyr Gly
    130                 135                 140
Gly Arg Ala Ser Asp Tyr Lys Ser Ala His Lys Gly Phe Lys Gly Val
```

```
                145                 150                 155                 160
Asp Ala Gln Gly Thr Leu Ser Lys Ile Phe Lys Leu Gly Gly Arg Asp
                    165                 170                 175
Ser Arg Ser Gly Ser Pro Met Ala Arg Arg
                    180                 185

<210> SEQ ID NO 26
<211> LENGTH: 171
<212> TYPE: PRT
<213> ORGANISM: Homo sapiens

<400> SEQUENCE: 26

Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
                20                  25                  30
His Arg Asp Thr Gly Ile Leu Asp Ser Ile Gly Arg Phe Phe Gly Gly
            35                  40                  45
Asp Arg Gly Ala Pro Lys Arg Gly Ser Gly Lys Asp Ser His His Pro
        50                  55                  60
Ala Arg Thr Ala His Tyr Gly Ser Leu Pro Gln Lys Ser His Gly Arg
65                  70                  75                  80
Thr Gln Asp Glu Asn Pro Val Val His Phe Phe Lys Asn Ile Val Thr
                85                  90                  95
Pro Arg Thr Pro Pro Pro Ser Gln Gly Lys Gly Arg Gly Leu Ser Leu
                100                 105                 110
Ser Arg Phe Ser Trp Gly Ala Glu Gly Gln Arg Pro Gly Phe Gly Tyr
            115                 120                 125
Gly Gly Arg Ala Ser Asp Tyr Lys Ser Ala His Lys Gly Phe Lys Gly
        130                 135                 140
Val Asp Ala Gln Gly Thr Leu Ser Lys Ile Phe Lys Leu Gly Gly Arg
145                 150                 155                 160
Asp Ser Arg Ser Gly Ser Pro Met Ala Arg Arg
                    165                 170

<210> SEQ ID NO 27
<211> LENGTH: 160
<212> TYPE: PRT
<213> ORGANISM: Homo sapiens

<400> SEQUENCE: 27

Met Ala Ser Gln Lys Arg Pro Ser Gln Arg His Gly Ser Lys Tyr Leu
1               5                   10                  15
Ala Thr Ala Ser Thr Met Asp His Ala Arg His Gly Phe Leu Pro Arg
                20                  25                  30
His Arg Asp Thr Gly Ile Leu Asp Ser Ile Gly Arg Phe Phe Gly Gly
            35                  40                  45
Asp Arg Gly Ala Pro Lys Arg Gly Ser Gly Lys Asp Ser His His Pro
        50                  55                  60
Ala Arg Thr Ala His Tyr Gly Ser Leu Pro Gln Lys Ser His Gly Arg
65                  70                  75                  80
Thr Gln Asp Glu Asn Pro Val Val His Phe Phe Lys Asn Ile Val Thr
                85                  90                  95
Pro Arg Thr Pro Pro Pro Ser Gln Gly Lys Gly Ala Glu Gly Gln Arg
                100                 105                 110
Pro Gly Phe Gly Tyr Gly Gly Arg Ala Ser Asp Tyr Lys Ser Ala His
```

```
            115                 120                 125
Lys Gly Phe Lys Gly Val Asp Ala Gln Gly Thr Leu Ser Lys Ile Phe
    130                 135                 140

Lys Leu Gly Gly Arg Asp Ser Arg Ser Gly Ser Pro Met Ala Arg Arg
145                 150                 155                 160

<210> SEQ ID NO 28
<211> LENGTH: 253
<212> TYPE: PRT
<213> ORGANISM: Homo sapiens

<400> SEQUENCE: 28

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
                20                  25                  30

Thr Gly Gly Ser Arg Tyr Pro Gly Gln Gly Ser Pro Gly Gly Asn Arg
            35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
                100                 105                 110

Ala Gly Ala Ala Ala Ala Gly Ala Val Val Gly Gly Leu Gly Gly Tyr
            115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
    195                 200                 205

Val Val Glu Gln Met Cys Ile Thr Gln Tyr Glu Arg Glu Ser Gln Ala
210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 29
<211> LENGTH: 244
<212> TYPE: PRT
<213> ORGANISM: Homo sapiens

<400> SEQUENCE: 29

Gly Leu Lys Gly Lys Arg Gly Asp Ser Gly Ser Pro Ala Thr Trp Thr
1               5                   10                  15

Thr Arg Gly Phe Val Phe Thr Arg His Ser Gln Thr Thr Ala Ile Pro
                20                  25                  30

Ser Cys Pro Glu Gly Thr Val Pro Leu Tyr Ser Gly Phe Ser Phe Leu
```

```
                          35                  40                  45
Phe Val Gln Gly Asn Gln Arg Ala His Gly Gln Asp Leu Gly Thr Leu
    50                  55                  60
Gly Ser Cys Leu Gln Arg Phe Thr Thr Met Pro Phe Leu Phe Cys Asn
65                  70                  75                      80
Val Asn Asp Val Cys Asn Phe Ala Ser Arg Asn Asp Tyr Ser Tyr Trp
                85                  90                  95
Leu Ser Thr Pro Ala Leu Met Pro Met Asn Met Ala Pro Ile Thr Gly
                100                 105                 110
Arg Ala Leu Glu Pro Tyr Ile Ser Arg Cys Thr Val Cys Glu Gly Pro
            115                 120                 125
Ala Ile Ala Ile Ala Val His Ser Gln Thr Thr Asp Ile Pro Pro Cys
    130                 135                 140
Pro His Gly Trp Ile Ser Leu Trp Lys Gly Phe Ser Phe Ile Met Phe
145                 150                 155                     160
Thr Ser Ala Gly Ser Glu Gly Thr Gly Gln Ala Leu Ala Ser Pro Gly
                165                 170                 175
Ser Cys Leu Glu Glu Phe Arg Ala Ser Pro Phe Leu Glu Cys His Gly
                180                 185                 190
Arg Gly Thr Cys Asn Tyr Tyr Ser Asn Ser Tyr Ser Phe Trp Leu Ala
            195                 200                 205
Ser Leu Asn Pro Glu Arg Met Phe Arg Lys Pro Ile Pro Ser Thr Val
    210                 215                 220
Lys Ala Gly Glu Leu Glu Lys Ile Ile Ser Arg Cys Gln Val Cys Met
225                 230                 235                     240

Lys Lys Arg His

<210> SEQ ID NO 30
<211> LENGTH: 42
<212> TYPE: PRT
<213> ORGANISM: Homo sapiens

<400> SEQUENCE: 30

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
                35                  40
```

METHOD FOR TREATING AND DIAGNOSING DISEASE USING INHIBITORS OF GOODPASTURE ANTIGEN BINDING PROTEIN

CROSS REFERENCE

This application is a divisional of U.S. patent application Ser. No. 13/400,831 filed Feb. 21, 2012, which claims priority to U.S. provisional patent applications 61/444,872 filed Feb. 21, 2011, 61/469,945 filed Mar. 31, 2011, and 61/473,411 filed Apr. 8, 2011, each incorporated by reference herein in its entirety.

BACKGROUND OF THE INVENTION

The conformation of the non-collagenous (NC1) domain of the α3 chain of the basement membrane collagen IV [α3(IV)NC1] depends in part on phosphorylation. Goodpasture Antigen Binding Protein (GPBP, 77 kD GPBP or GPBP-1) (WO 00/50607; WO 02/061430) is a non-conventional protein kinase that catalyzes the conformational isomerization of the α3(IV)NC1 domain during its supramolecular assembly, resulting in the production and stabilization of multiple α3(IV)NC1 conformers in basement membranes. Elevated levels of GPBP have been associated with the production of non-tolerized α3(IV)NC1 conformers, which conduct the autoimmune response mediating Goodpasture ("GP") disease. In GP patients, autoantibodies against the non-collagenous C-terminal domain (NC1) of the type IV collagen α3 chain ("Goodpasture antigen" or "GP antigen") cause a rapidly progressive glomerulonephritis (GN) and often lung hemorrhage, the two cardinal clinical manifestations of the GP syndrome.

SUMMARY OF THE INVENTION

In a first aspect, the present invention provides methods for treating chronic kidney disease (CKD), comprising administering to a subject in need thereof an amount effective of an inhibitor of 77 kD GPBP to treat the CKD.

In a second aspect, the present invention provides methods for treating immune complex-mediated glomerulonephritis (GN), comprising administering to a subject in need thereof an amount effective of an inhibitor of 77 kD GPBP to treat the immune complex-mediated GN. In one embodiment, the immune complex-mediated GN is associated with an autoimmune disorder selected from the group consisting of IgA nephropathy, systemic lupus erythematosus (SLE) and Goodpasture disease.

In a third aspect, the present invention provides methods for treating pulmonary fibrosis (PF), comprising administering to a subject in need thereof an amount effective of an inhibitor of 77 kD GPBP to treat the PF. In one embodiment, the PF is non-idiopathic PF.

In each of the first through third aspects of the invention, the subject is preferably a human. In each aspect, any suitable 77 kD GPBP inhibitor may be used; in one embodiment, the inhibitor is an antibody that binds to 77 kD GPBP, such as an antibody selective for the 77 kD isoform of GPBP.

In another embodiment, the GPBP inhibitor comprises a polypeptide comprising an amino acid sequence according to the general formula X1-SHCIX2-X3 (SEQ ID NO: 2), wherein:

X1 is 0-10 amino acids of the sequence ATTAGILATL (SEQ ID NO: 3);
X2 is E or Q; and
X3 is 0-10 amino acids of the sequence LMVKREDSWQ (SEQ ID NO: 4).

In another embodiment, the inhibitor comprises a compound of formula (I):

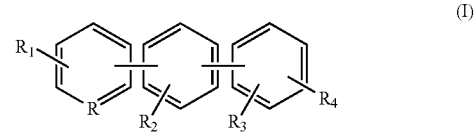

(I)

or a pharmaceutically acceptable salt thereof, wherein:
R is selected from N and $CR_5$;
$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino ($C_1$-$C_6$ alkyl), sulfanyl($C_1$-$C_6$ alkyl), ($C_1$-$C_6$ alkyl)sulfanyl ($C_1$-$C_6$ alkyl), —$(CH_2)_{1-5}$—C(O)($C_1$-$C_6$ alkoxy), —$(CH_2)_{1-5}$—C(O)$NH_2$, (aryl)$C_2$-$C_6$ alkyl, and (heteroaryl) $C_1$-$C_6$ alkyl;

$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);

$R_2$ is $C_1$-$C_6$ alkyl, halo($C_1$-$C_6$ alkyl), $C_1$-$C_6$ alkoxy, halo ($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl ($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)$NH_2$, (aryl)$C_1$-$C_6$ alkyl, or (heteroaryl) $C_1$-$C_6$ alkyl;

$R_3$ is $C_1$-$C_6$ alkyl, halo($C_1$-$C_6$ alkyl), $C_1$-$C_6$ alkoxy, halo ($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl ($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N($C_1$-$C_6$ alkyl)$_2$, —CH=CH—C (O)OH, —CH=CH—C(O)($C_1$-$C_6$ alkoxy), (aryl)$C_1$-$C_6$ alkyl, or (heteroaryl)$C_1$-$C_6$ alkyl; and $R_4$ is hydroxy, halogen, $C_1$-$C_6$ alkyl, $C_1$-$C_6$ alkoxy, halo ($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N ($C_1$-$C_6$ alkyl)$_2$, —CH=CH—C(O)OH, —CH=CH—C(O) ($C_1$-$C_6$ alkoxy), —O$(CH_2)_{1-5}$—C(O)OH, —O$(CH_2)_{1-5}$—C (O)($C_1$-$C_6$ alkoxy), (aryl)$C_1$-$C_6$ alkyl, or (heteroaryl)$C_1$-$C_6$ alkyl.

In a fourth aspect, the present invention provides methods for diagnosing rheumatoid arthritis (RA) or pulmonary fibrosis (PF) comprising (a) contacting a plasma sample from a subject at risk of RA or PF with a GPBP-binding molecule that binds to 77 kD GPBP under conditions to promote selective binding of the GPBP-binding molecule to the GPBP;

(b) detecting complex formation between the GPBP-binding molecule and the 77 kD GPBP in the plasma sample;

(c) comparing an amount of complex formed between the GPBP-binding molecule and the GPBP in the plasma sample to control; and (d) diagnosing the subject as having RA or PF based on the comparison, or providing the comparison to an entity for diagnosis of RA or PF.

In one embodiment, the 77 kD GPBP-binding molecule comprises an antibody that binds to native 77 kD GPBP, such as an antibody is selective for the 77 kD isoform of GPBP.

In another embodiment, the detecting comprises use of a technique selected from the group consisting of ELISA, immunofluorescence, and chromatography.

In some embodiments where the subject is at risk of RA, the subject may be suffering from one or more symptoms selected from the group consisting of: one or more swollen joints, one or more stiff joints, one or more warm joints, joint stiffness early in the morning that typically lasts for more than an hour, excess synovial fluid, development of fibrous tissue in the synovium, and impaired range of joint movement.

In some embodiments where the subject is at risk of PF, the subject may be suffering from one or more symptoms selected from the group consisting of: chronic dry coughing, fatigue, weakness, chest discomfort, loss of appetite, rapid weight loss, and dyspnea with exertion.

In any embodiments of this fourth aspect, the methods may further comprise determining the subject's plasma level of C reactive protein (CRP), comparing the amount of CRP in the subject's plasma to control, and using the CRP comparison in aiding the diagnosis of RA or PF.

In another embodiment, the invention provides methods for diagnosing CKD or immune complex-mediated GN, comprising (a) contacting a plasma sample from a subject at risk of CKD or immune complex-mediated GN with a GPBP-binding molecule that binds to 77 kD GPBP under conditions to promote selective binding of the GPBP-binding molecule to the GPBP;

(b) detecting
 (i) complex formation between the GPBP-binding molecule and the 77 kD GPBP in the plasma sample; and
 (ii) determining the subject's plasma level of C reactive protein (CRP)

(c) comparing
 (i) an amount of complex formed between the GPBP-binding molecule and the 77 kD GPBP in the plasma sample to control; and
 (ii) an amount of CRP in the subject's plasma to control; and (d) diagnosing the subject as having CKD or immune complex-mediated GN based on the comparisons, or providing the comparisons to an entity for diagnosis of CKD or immune complex-mediated GN.

In a fifth aspect, the present invention provides methods for identifying compounds to treat CKD, immune complex-mediated GN, and/or PF, comprising contacting a 77 kD GPBP-77 kD GPBP-substrate binding complex with one or more test compounds under binding conditions, wherein those test compounds that displace 77 kD GPBP binding from the binding complex are candidate compounds for treating CKD, immune complex-mediated GN, and/or PF.

In a sixth aspect, the present invention provides methods for identifying compounds to treat CKD, immune complex-mediated GN, and/or PF, comprising contacting a 77 kD GPBP-substrate under binding conditions with
(a) one or more test compounds; and
(b) 77 kD GPBP;
wherein those test compounds that outcompete 77 kD GPBP for binding to the 77 kD GPBP-binding substrate are candidate compounds for treating CKD, immune complex-mediated GN, and/or PF.

(levels from individual serum of 113 patients having significant levels of anti-cyclic citrullinated peptide (anti-CCP) (RA) and 100 healthy donors (Control). Bars indicate the mean value within a series. On the right is indicated the result of the Mann-Whittney analysis. In B, each circle represents the respective values of circulating CRP and GPBP-1 found in individual sera from RA patients having significant levels of anti-CCP.

Figure 7:
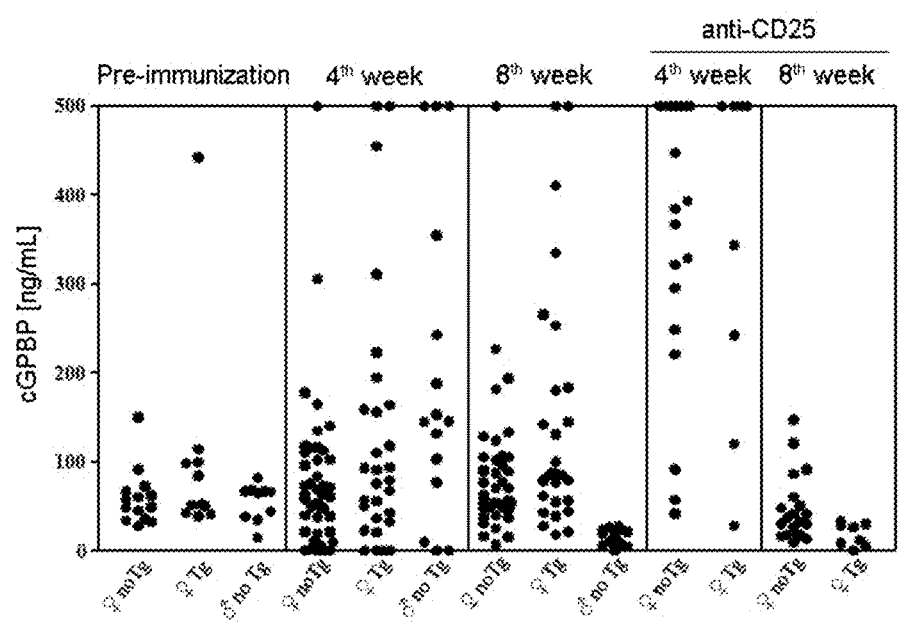

FIG. 7. Circulating GPBP-1 levels in mice developing collagen-induced arthritis (CIA). Dots represent cGPBP-1 levels in individual serum of the indicated mice before immunization with bovine type II collagen (pre-immunization) or at the indicated times after immunization.

Figure 8:
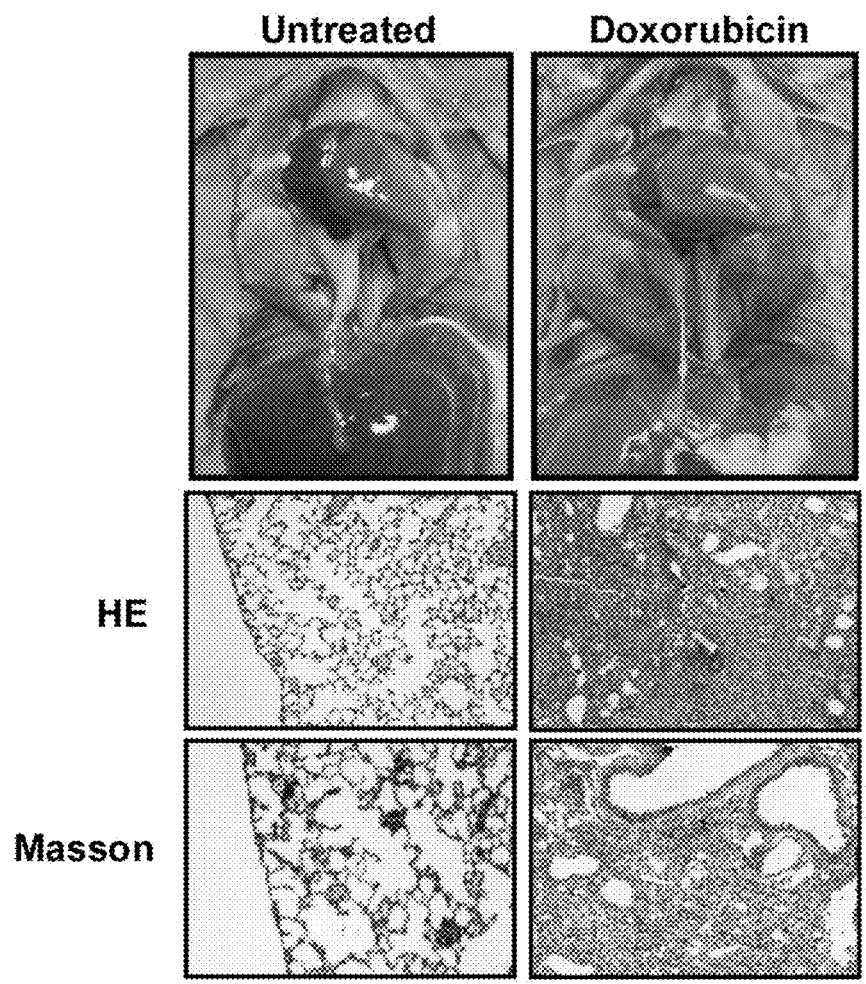

FIG. 8. Induction of pulmonary fibrosis (PF) by doxorubicin. Macroscopic aspect (upper panels) and representative histological appearance of the lungs (×10) stained with heamatoxylin/eosin (middle panels) or Masson's trichrome (lower panels) in control and doxorubicin treated mice 12 days after the i.t. instillation of the drug.

Figure 9:
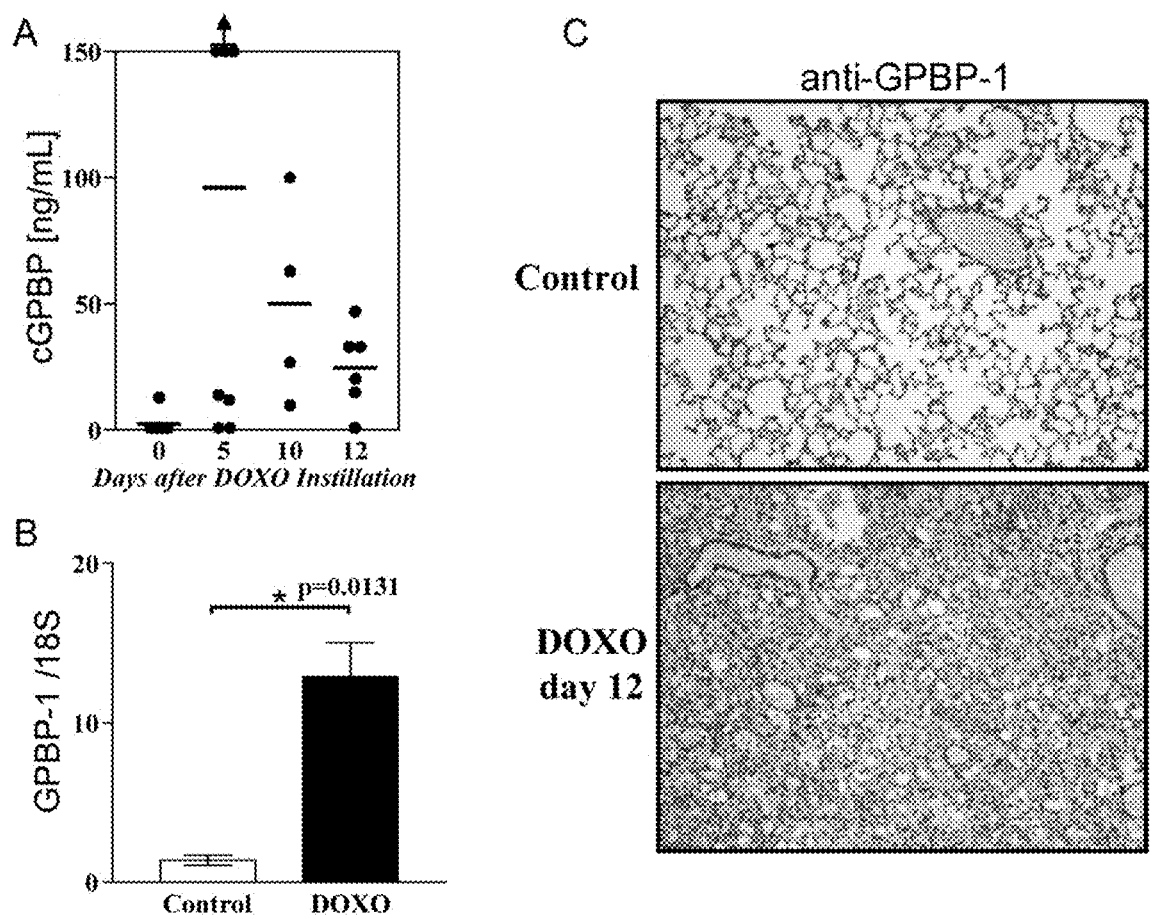

FIG. 9. Expression of GPBP-1 during the development of doxorubicin-induced PF. In A shown are the levels of cGPBP-1 at the indicated time points after the i.t. instillation of doxorubicin. Results are expressed as the values of individual mice. Bars represent the mean value of each examination. In B shown are the levels of expression of GPBP-1 mRNA in the lung of control and doxorubicin treated mice 12 days after drug instillation. Results are expressed as mean±SD fold change of GPBP-1 expression relative to the ribosomal 18S subunit expression measured in parallel in each sample. In C, Immunohistochemical examination of GPBP-1 expression using a polyclonal anti-GPBP-1 antibody in lung sections of control and doxorubicin treated mice 12 days after drug instillation (×10).

Figure 10:
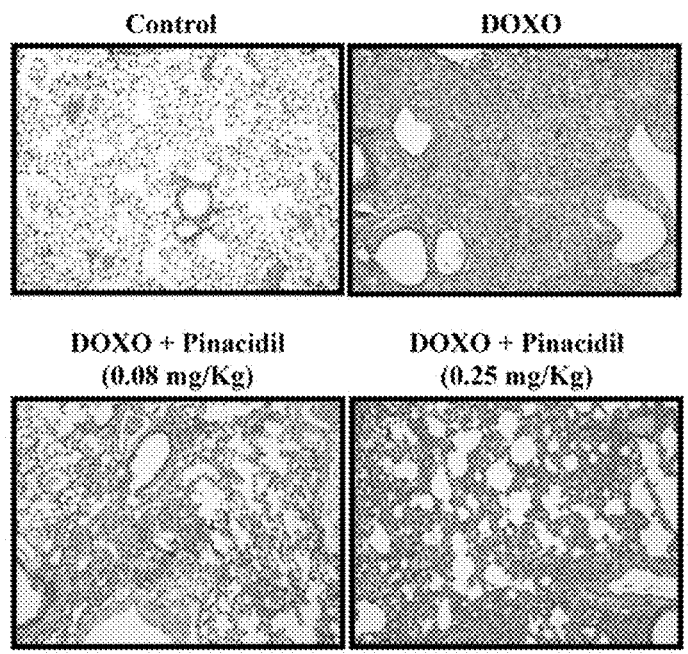
Figure 10:
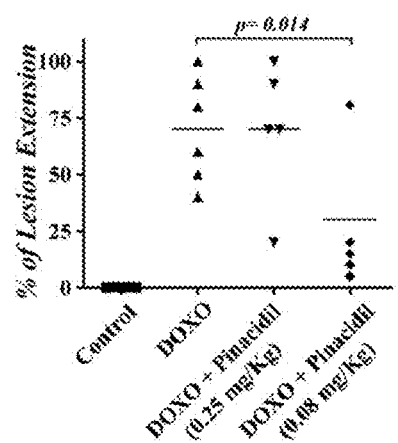

FIG. 10. Effect of pinacidil treatment in the development of doxorubicin-induced PF. Lungs from untreated mice or animals treated with different doses of pinacidil were examined 12 days after doxorubicin instillation. Lungs sections stained with heamatoxylin/eosin (×10) are shown (left panels). In addition, the extension of histological lesions is expressed in individual mice of each experimental group as the percentage of affected parenchyma (right panel).

Figure 11:
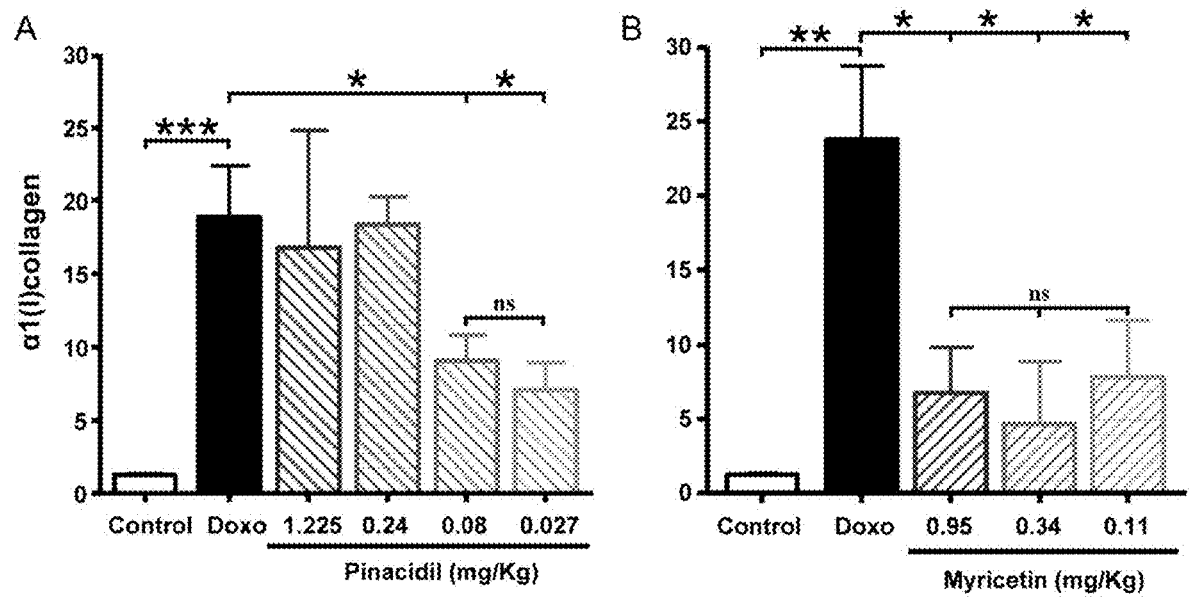

FIG. 11. Effects of pinacidil or myricetin treatment in the induction of collagen I expression during the development of doxorubicin induced PF. The expression of α1(I) collagen mRNA was determined in untreated or pinacidil or myricetin treated mice 12 days after doxorubicin instillation using RT-qPCR. Results are expressed as mean±SD fold change of α1(I) collagen expression relative to the ribosomal 18S subunit expression measured in parallel in each sample. Statistic differences are indicated as follow: ns: non-significant, *$p<0.05$, $p<0.01$, * $p<0.005$.

Figure 12:
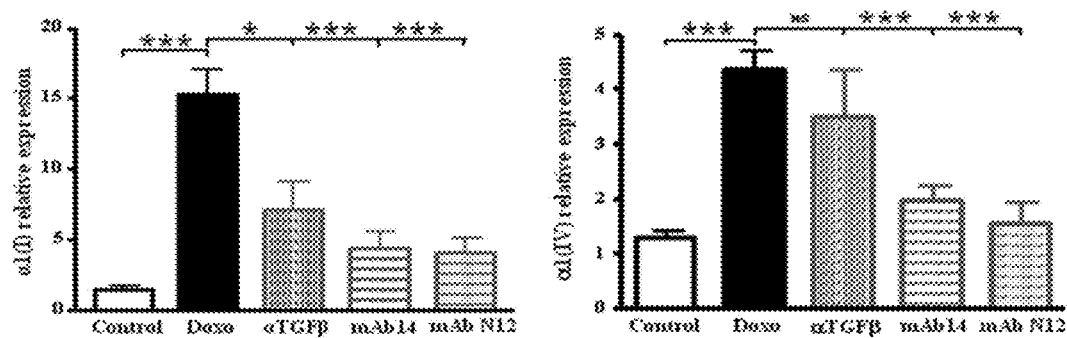

FIG. 12. Effect of GPBP mAbs on doxorubicin-induced PF. The expression of α1(I) and α1(IV) collagens mRNAs was determined in untreated, anti-TGFβ, mAb 14 or mAb N12 treated mice 12 days after doxorubicin instillation using RT-qPCR. Results are expressed as mean±SD fold change of α1(I) collagen expression relative to the ribosomal 18S subunit expression measured in parallel in each sample. Statistic differences are indicated as follow: ns: non-significant, *$p<0.05$, *** $p<0.005$.

DETAILED DESCRIPTION OF THE INVENTION

All references cited are herein incorporated by reference in their entirety. Within this application, unless otherwise stated, the techniques utilized may be found in any of several well-known references such as: *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.).

As used herein, the singular forms "a", "an" and "the" include plural referents unless the context clearly dictates otherwise. "And" as used herein is interchangeably used with "or" unless expressly stated otherwise.

All common terms between different aspects and embodiments of the invention have the same meaning unless the context clearly dictates otherwise.

As used in this application, the term "native protein" means the protein naturally produced by the cell, including any post-translational modifications (PTMs), and includes non-denatured protein, or denatured protein (as, for example, naturally produced protein substantially purified and subjected to one or more denaturing agents to, for example, run on a SDS-PAGE gel).

As used in this application, "substantially purified polypeptide" means that the polypeptide has been separated from its in vivo cellular environments. It is further preferred that the isolated polypeptides are also substantially free of gel agents, such as polyacrylamide, agarose, and chromatography reagents.

Unless clearly indicated otherwise by the context, embodiments disclosed for one aspect of the invention can be used in other aspects of the invention as well, and in combination with embodiments disclosed in other aspects of the invention.

In a first aspect, the present invention provides methods for treating chronic kidney disease (CKD), comprising administering to a subject in need thereof an amount effective of an inhibitor of 77 kD GPBP to treat the CKD.

As shown in the examples that follow, inhibitors of 77 kD GPBP reduce inflammatory infiltrates in kidneys, and thus can be used for treating CKD. The last stage of any inflammation is fibrosis, and renal tubulo-interstitial fibrosis represents the final common pathway for all kidney diseases, leading to gradual expansion of the fibrotic mass which destroys the normal structure of the tissue and results in CKD.

The subject can be any subject that might benefit from treatment, such as a mammal. In a preferred embodiment, the subject is a human subject. The amino acid sequence of 77 kD GPBP, now also called GPBP or GPBP-1 (SEQ ID NO: 1) was disclosed in U.S. Pat. No. 6,579,969 Issued Jun. 17, 2003 and corresponding PCT publication WO 00/50607, published Aug. 31, 2000. As disclosed therein, and in WO2010/009856 and U.S. Pat. No. 7,935,492, the human GPBP mRNA undergoes alternative splicing to produce GPBPΔ26, now also called CERT and GPBP-2, and non-canonical translation initiation to produce 91-kDa GPBP, now also called GPBP-3). The different isoforms have been demonstrated to have different functions, with the 77 kD GPBP reaching the extracellular compartment and existing in a soluble immunoprecipitable form and can be isolated from blood.

As used herein, "chronic kidney disease" is a progressive loss in renal function over a period of months or years, regardless of underlying pathology. In one embodiment, individuals with a glomerular filtration rate (GFR)<60 mL/min/1.73 m$^2$ for 3 months are classified as having CKD, irrespective of the presence or absence of kidney damage. In another embodiment, individuals with kidney damage are classified as having CKD, irrespective of the level of GFR. Kidney damage is defined as pathological abnormalities or markers of damage, including abnormalities in blood or urine test or imaging studies In various embodiments, the methods can be used to treat non-dialysis dependent CKD, such as:

Stage 1: Slightly diminished function; kidney damage with normal or relatively high GFR (≥90 mL/min/1.73 m$^2$);

Stage 2: Mild reduction in GFR (60-89 mL/min/1.73 m$^2$) with kidney damage;

Stage 3: Moderate reduction in GFR (30-59 mL/min/1.73 m$^2$); and

Stage 4: Severe reduction in GFR (15-29 mL/min/1.73 m$^2$).

As used herein, "treating" CKD means (a) slowing progression of the subject to end stage renal disease (ESRD); (b) slowing the reduction in GFR in the subject; (c) limiting the progression of renal disease in the subject; and/or (d) reducing the severity of CKD symptoms.

As used herein, "limiting the progression of CKD" means to reduce or prevent decreases in renal function in those patients receiving treatment relative to patients not receiving the treatment. Such treatment thus reduces the need for kidney dialysis or transplantation in patients.

The progression of renal disease can be measured in various ways, including the following:

(a) Proteinuria (ie: increased loss of protein into the urine; often assessed by measurement of albumin levels (ie: "albuminuria"));

(b) Impaired glomerular clearance (ie: kidney function to clear substances from blood; can be measured, for example, by creatinine (ie: "impaired creatinine clearance"), inulin, or urea clearance);

(c) Increased levels of serum creatinine; and/or (d) Increased levels of urinary transforming growth factor beta (TGF-β).

Thus, the methods of the invention can be used, for example, to limit the increase in one or more of proteinuria, albuminuria, serum creatinine levels, and urinary TGF-β levels, and/or to limit the impairment of glomerular clearance and/or creatinine clearance in subject being treated by the methods of the invention.

In a second aspect, the present invention provides methods for treating immune complex-mediated GN, comprising administering to a subject in need thereof an amount effective of an inhibitor of 77 kD GPBP to treat the immune complex-mediated GN. The subject can be any subject that might benefit from treatment, such as a mammal. In a preferred embodiment, the subject is a human subject.

As used herein, "GN" is a renal disease characterized by glomerular damage, while "immune complex-mediated GN" means that the GN is characterized by glomerular depositions of immune complexes.

In one embodiment, the immune complex-mediated GN is associated with an autoimmune disorder selected from the group consisting of IgA nephropathy, systemic lupus erythematosus (SLE) and Goodpasture disease. As used herein, "treating" immune complex-mediated GN means (a) slowing progression of the glomerular damage; (b) slowing progression of glomerular immune complex deposits; (c) reducing glomerular inflammation; (d) reducing glomerular immune complex deposits; and/or (d) slowing progression to ESRD.

As shown in the examples that follow, inhibitors of 77 kD GPBP repair glomerular basement membrane collagen-based alterations, reduce the glomerular deposits of immune complexes and attenuate inflammation associated with immune complex-mediated GN.

In a preferred embodiment of the methods of the first and second aspect of the invention, the 77 kD GPBP inhibitors may be co-administered with one or more other therapeutics, such as standard of care therapeutics for the disease being treated. In one preferred embodiment, such one or more compounds are selected from the group consisting of angiotensin converting enzyme inhibitors and angiotensin receptor blockers, or pharmaceutically acceptable salts thereof in a pharmaceutically acceptable carrier. Non-limiting examples of angiotensin converting enzyme inhibitors for use in the present invention include benazepril, benazeprilat, captopril, delapril, fentiapril, fosinopril, libenzapril, moexipril, pentopril, perindopril, pivopril, quinapril, quinaprilat, ramipril, spirapril, spiraprilat, zofenopril, ceronapril, enalapril, indolapril, lisinopril, alacepril, and cilazapril, or pharmaceutically acceptable salts thereof. Non-limiting examples of angiotensin receptor blockers for use in the present invention include losartan, candesartan, irbesartan, olmesartan, valsartan, telmisartan, eprosartan, and tasosartan.

In another embodiment, the inhibitor can be administered in combination with belimumab.

In a third aspect, the present invention provides methods for treating pulmonary fibrosis (PF), comprising administering to a subject in need thereof an amount effective of an inhibitor of 77 kD GPBP to treat the PF The subject can be any subject that might benefit from treatment, such as a mammal. In a preferred embodiment, the subject is a human subject.

PF is the formation or development of excess connective tissue (fibrosis) in the lungs. Symptoms of pulmonary fibrosis include, but are not limited to shortness of breath, chronic dry, hacking coughing, fatigue and weakness, chest discomfort, and/or loss of appetite and rapid weight loss. Pulmonary fibrosis is suggested by a history of progressive shortness of breath (dyspnea) with exertion. Sometimes, fine inspiratory crackles can be heard at the lung bases on auscultation. A high resolution CAT scan will generally demonstrate abnormalities.

As shown in the examples that follow, inhibitors of GPBP were effective in treating doxorubicin-induced PF, an animal model for human PF.

The PF to be treated by the methods of the invention may be a secondary effect of other diseases (i.e.: "interstitial lung disease", including but not limited to autoimmune disorders (ex: rheumatoid arthritis-RA-, SLE, scleroderma, etc.), viral infections or other microscopic injuries to the lung (such as exposure to asbestos, silicon, cigarette smoke, etc.), or may be idiopathic (i.e. "idiopathic pulmonary fibrosis.")

As used herein, "treating" PF means (a) slowing progression of the lung fibrosis; and/or (b) reducing PF symptoms.

In a preferred embodiment of the methods of the third aspect of the invention, the 77 kD GPBP inhibitors may be co-administered with one or more other therapeutics, such as standard of care therapeutics for the disease being treated. In one preferred embodiment, such one or more compounds are selected from the group consisting of corticosteroids, immunosupressants (including but not limited to cyclophosphamide, azathioprine, and methotrexate), anti-inflammatory agents, IFN-γ, mycophenolate mofetil, and pirfenidone.

In each of these aspects, the methods may be carried out on any suitable subject, such as those that have been identified as over-expressing 77 kD GPBP. For example, a normal value of 77 kD GPBP as a reference for a standard curve is less than 10 ng/ml in plasma. In various preferred embodiments, a normal 77 kD GPBP range is between ~1 ng/ml-10 ng/ml in plasma. Thus, in one embodiment, subjects identified as having more than 10 mg/ml of 77 kD GPBP in their plasma are treated according to the methods of the invention. Methods for determining the amount of circulating 77 kD GPBP are known in the art (see WO 2010/009856 and U.S. Pat. No. 7,935,492), and examples are described below.

In each of these aspects of the invention reciting therapeutic treatment methods, any suitable inhibitor of 77 kD GPBP can be used. In one embodiment, the inhibitor is selected from the group consisting of 77 kD GPBP antisense RNA, 77 kD GPBP siRNA, and 77 kD GPBP antibodies. In a preferred embodiment, the inhibitor of 77 kD GPBP is a 77 kD GPBP antibody, or pharmaceutically acceptable salts thereof. Exemplary antibodies are disclosed, for example, in WO 2010/009856 and U.S. Pat. No. 7,935,492. In a preferred embodiment, the antibodies recognize native 77 kD GPBP, including but not limited to those antibodies disclosed in WO 2010/009856 and U.S. Pat. No. 7,935,492, which provides teachings for those of skill in the art to generate antibodies to native 77 kD GPBP. As used herein, "antibodies to native 77 kD GPBP" means that the antibodies bind to native 77 kD GPBP, and does not require that they not bind to other GPBP species. In one embodiment, the antibodies are specific for 77 kD GPBP. In a further preferred embodiment that can be combined with any other embodiment, the antibody is a monoclonal antibody, such as a humanized monoclonal antibody.

The term antibody as used herein is intended to include antibody fragments thereof which are selectively reactive with the polypeptides of the invention, or fragments thereof. Antibodies can be fragmented using conventional techniques, and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

Examples of monoclonal antibody fragments include (i) a Fab fragment, a monovalent fragment consisting essentially of the VL, VH, CL and CH I domains; (ii) F(ab)2 and F(ab')2 fragments, bivalent fragments comprising two Fab fragments linked by a disulfide bridge at the hinge region; (iii) a Fd fragment consisting essentially of the VH and CH1 domains; (iv) a Fv fragment consisting essentially of the VL and VH domains of a single arm of an antibody, (v) a dAb fragment (Ward et al., (1989) Nature 341:544-546), which consists essentially of a VH domain; and (vi) one or more isolated CDRs or a functional paratope.

Monoclonal antibodies can be produced by obtaining spleen cells from the animal. (See Kohler and Milstein, Nature 256, 495-497 (1975)). In one example, monoclonal antibodies (mAb) of interest are prepared by immunizing inbred mice with the 77 kD GPBP, or an antigenic fragment thereof. The mice are immunized by the IP or SC route in an amount and at intervals sufficient to elicit an immune response. The mice receive an initial immunization on day 0 and are rested for about 3 to about 30 weeks. Immunized mice are given one or more booster immunizations of by the intravenous (IV) route. Lymphocytes, from antibody positive mice are obtained by removing spleens from immunized mice by standard procedures known in the art. Hybridoma cells are produced by mixing the splenic lymphocytes with an appropriate fusion partner under conditions which will allow the formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and are screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

"Humanized antibody" refers to antibodies derived from a non-human antibody, such as a mouse monoclonal antibody. Alternatively, humanized antibodies can be derived from chimeric antibodies that retain or substantially retains the antigen-binding properties of the parental, non-human, antibody but which exhibits diminished immunogenicity as compared to the parental antibody when administered to humans. For example, chimeric antibodies can comprise human and murine antibody fragments, generally human constant and mouse variable regions. Since humanized antibodies are far less immunogenic in humans than the non-human monoclonal antibodies, they are preferred for therapeutic antibody use.

Humanized antibodies can be prepared using a variety of methods known in the art, including but not limited to (1) grafting complementarity determining regions from a non-human monoclonal antibody onto a human framework and constant region ("humanizing"), and (2) transplanting the non-human monoclonal antibody variable domains, but "cloaking" them with a human-like surface by replacement of surface residues ("veneering"). These methods are disclosed, for example, in, e.g., Jones et al., Nature 321:522-525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239:1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991).

To generate an antibody response, the polypeptides of the present invention are typically formulated with a pharmaceutically acceptable carrier for parenteral administration. Such acceptable adjuvants include, but are not limited to, Freund's complete, Freund's incomplete, alum-precipitate, water in oil emulsion containing *Corynebacterium parvum* and tRNA. The formulation of such compositions, including the concentration of the polypeptide and the selection of the vehicle and other components, is within the skill of the art.

In another embodiment, the 77 kD GPBP inhibitor is a peptide inhibitor disclosed in WO 2004/070025 and U.S. Pat. No. 7,326,768, or pharmaceutically acceptable salts thereof. In one embodiment, the peptide inhibitor is a polypeptide comprising or consisting of an amino acid sequence according to the general formula X1-SHCIX2-X3 (SEQ ID NO: 2) wherein:

X1 is 0-10 amino acids of the sequence ATTAGILATL (SEQ ID NO:3);

X2 is E or Q; and

X3 is 0-10 amino acids of the sequence LMVKREDSWQ (SEQ ID NO:4).

In a preferred embodiment, the peptide inhibitor comprises or consists of a sequence selected from the group consisting of SHCIE (SEQ ID NO:5), SHCIQ (SEQ ID NO:6), ILATLSHCIELMVKR (SEQ ID NO: 7), and ILATLSHCIQLMVKR (SEQ ID NO: 8).

In another embodiment, the peptide inhibitor comprises or consists of at least six (6, 7, 8, 9, or all) contiguous amino acids EKTAGKPILF (SEQ ID NO: 9). In a preferred embodiment, the isolated polypeptide comprises or consists of the sequence EKTAGKPILF (SEQ ID NO: 10).

The polypeptides can further be derivatized to provide enhanced half-life, such as by the addition of polyethylene glycol (PEG) or as otherwise known in the art. The polypeptides of the invention may comprise L-amino acids, D-amino acids (which are resistant to L-amino acid-specific proteases in vivo), a combination of D- and L-amino acids, and various "designer" amino acids (e.g., β-methyl amino acids, Cα-methyl amino acids, and Nα-methyl amino acids, etc.) to convey special properties. Synthetic amino acids include ornithine for lysine, and norleucine for leucine or isoleucine.

In addition, the polypeptides can have peptidomimetic bonds, such as ester bonds, to prepare polypeptides with novel properties. For example, a polypeptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a polypeptide would be resistant to protease activity, and would possess an extended half-live in vivo.

The term "polypeptide" is used in its broadest sense to refer to a sequence of subunit amino acids, amino acid analogs, or peptidomimetics. The subunits are linked by peptide bonds, although the polypeptide can comprise further moieties that are not necessarily linked to the polypeptide by a peptide bond. For example, as discussed above, the polypeptide can further comprise a non-amino acid molecule that contains an aromatic ring.

The polypeptides described herein may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic.

Preferably, the polypeptides for use in the methods of the present invention are chemically synthesized. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art.

Solid phase peptide synthesis may be accomplished by techniques familiar to those in the art and provided, such as by using automated synthesizers.

The peptide/antibody inhibitors may be administered together in a pharmaceutical composition with a pharmaceutically acceptable carrier. The pharmaceutical composition may comprise in addition to the peptide inhibitor (a) a lyoprotectant; (b) a surfactant; (c) a bulking agent; (d) a tonicity adjusting agent; (e) a stabilizer; (f) a preservative and/or (g) a buffer. In some embodiments, the buffer in the pharmaceutical composition is a Tris buffer, a histidine buffer, a phosphate buffer, a citrate buffer or an acetate buffer. The pharmaceutical composition may also include a lyoprotectant, e.g. sucrose, sorbitol or trehalose. In certain embodiments, the pharmaceutical composition includes a preservative e.g. benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, and various mixtures thereof. In other embodiments, the pharmaceutical composition includes a bulking agent, like glycine. In yet other embodiments, the pharmaceutical composition includes a surfactant e.g., polysorbate-20, polysorbate-40, polysorbate-60, polysorbate-65, polysorbate-80 polysorbate-85, poloxamer-188, sorbitan monolaurate, sorbitan monopalmitate, sorbitan monostearate, sorbitan monooleate, sorbitan trilaurate, sorbitan tristearate, sorbitan trioleate, or a combination thereof. The pharmaceutical composition may also include a tonicity adjusting agent, e.g., a compound that renders the formulation substantially isotonic or isoosmotic with human blood. Exemplary tonicity adjusting agents include sucrose, sorbitol, glycine, methionine, mannitol, dextrose, inositol, sodium chloride, arginine and arginine hydrochloride. In other embodiments, the pharmaceutical composition additionally includes a stabilizer, e.g., a molecule which, when combined with a protein of interest substantially prevents or reduces chemical and/or physical instability of the protein of interest in lyophilized or liquid form. Exemplary stabilizers include sucrose, sorbitol, glycine, inositol, sodium chloride, methionine, arginine, and arginine hydrochloride.

The peptide inhibitor/antibody may be the sole active agent in the pharmaceutical composition, or the composition may further comprise one or more other active agents suitable for an intended use.

In another embodiment, the 77 kD GPBP inhibitor is selected from the group consisting of DAB-Am32, pinacidil, and mirycetin, and pharmaceutically acceptable salts thereof, each of which is demonstrated in the examples that follow to be effective in the methods of the present invention.

In a further embodiment, the 77 kD GPBP inhibitor is one disclosed in WO 2011/054530 and US 20110105545. Thus, the compounds may be compounds of formula (I), or pharmaceutically acceptable salts thereof:

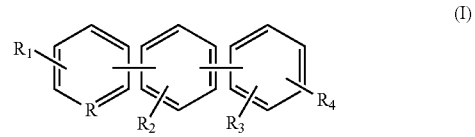

(I)

or a pharmaceutically acceptable salt thereof, wherein:

R is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino ($C_1$-$C_6$ alkyl), sulfanyl($C_1$-$C_6$ alkyl), ($C_1$-$C_6$ alkyl)sulfanyl ($C_1$-$C_6$ alkyl), —($CH_2$)$_{1-5}$—C(O)($C_1$-$C_6$ alkoxy), —($CH_2$)$_{1-5}$—C(O)$NH_2$, (aryl)$C_2$-$C_6$ alkyl, and (heteroaryl)$C_1$-$C_6$ alkyl;

$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);

$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —($CH_2$)$_{1-5}$—C(O)OH, —($CH_2$)$_{1-5}$—C(O)($C_1$-$C_6$ alkoxy), —($CH_2$)$_{1-5}$—C(O)$NH_2$, (aryl)$C_1$-$C_6$ alkyl, or (heteroaryl)$C_1$-$C_6$ alkyl;

$R_3$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_1$-$C_6$ alkyl), amino($C_1$-$C_6$ alkyl), sulfanyl($C_1$-$C_6$ alkyl), ($C_1$-$C_6$ alkyl)sulfanyl($C_1$-$C_6$ alkyl), —($CH_2$)$_{1-5}$—C(O)OH, —($CH_2$)$_{1-5}$—C(O)($C_1$-$C_6$ alkoxy), —($CH_2$)$_{1-5}$—C(O)$NH_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, —CH=CH—C(O)($C_1$-$C_6$ alkoxy), (aryl)$C_1$-$C_6$ alkyl, or (heteroaryl)$C_1$-$C_6$ alkyl; and $R_4$ is hydroxy, halogen, $C_1$-$C_6$ alkyl, $C_1$-$C_6$ alkoxy, halo($C_1$-$C_6$ alkoxy), benzyloxy, —($CH_2$)$_{1-5}$—C(O)OH, —($CH_2$)$_{1-5}$—C(O)($C_1$-$C_6$ alkoxy), —($CH_2$)$_{1-5}$—C(O)$NH_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, —CH=CH—C(O)($C_1$-$C_6$ alkoxy), —O($CH_2$)$_{1-5}$—C(O)OH, —O($CH_2$)$_{1-5}$—C(O)($C_1$-$C_6$ alkoxy), (aryl)$C_1$-$C_6$ alkyl, or (heteroaryl)$C_1$-$C_6$ alkyl.

In another embodiment, inhibitor compounds of formula (I) may be those of formula (II):

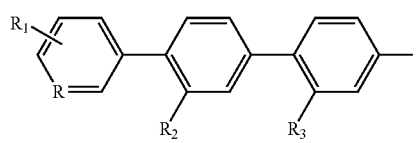

(II)

In another preferred embodiment, the inhibitors are compounds of formulae (I) or (II) wherein:

R is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), ($C_1$-$C_6$ alkyl)sulfanyl($C_1$-$C_6$ alkyl), —($CH_2$)$_{1-5}$—C(O)($C_1$-$C_6$ alkoxy), and —($CH_2$)$_{1-5}$—C(O)$NH_2$;

$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);

$R_2$ is $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), or ($C_1$-$C_6$ alkyl)sulfanyl($C_1$-$C_6$ alkyl);

$R_3$ is $C_1$-$C_6$ alkyl, halo($C_1$-$C_6$ alkyl), $C_1$-$C_6$ alkoxy, halo($C_1$-$C_6$ alkoxy), —($CH_2$)$_{1-5}$—C(O)OH, —($CH_2$)$_{1-5}$—C(O)($C_1$-$C_6$ alkoxy), —($CH_2$)$_{1-5}$—C(O)$NH_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, or —CH=CH—C(O)($C_1$-$C_6$ alkoxy); and $R_4$ is hydroxy, halogen, $C_1$-$C_6$ alkyl, $C_1$-$C_6$ alkoxy, halo($C_1$-$C_6$ alkoxy), benzyloxy, —($CH_2$)$_{1-5}$—C(O)OH, —($CH_2$)$_{1-5}$—C(O)($C_1$-$C_6$ alkoxy), —($CH_2$)$_{1-5}$—C(O)$NH_2$, —($CH_2$)$_{1-5}$—C(O)NH($C_1$-$C_6$ alkyl), —($CH_2$)$_{1-5}$—C(O)N($C_1$-$C_6$ alkyl)$_2$, —CH=CH—C(O)OH, —CH=CH—C(O)($C_1$-$C_6$ alkoxy), —O($CH_2$)$_{1-5}$—C(O)OH, or —O($CH_2$)$_{1-5}$—C(O)($C_1$-$C_6$ alkoxy).

In another preferred embodiment, the inhibitors are compounds of formula (II), wherein R is N. These compounds can be represented by formula (III):

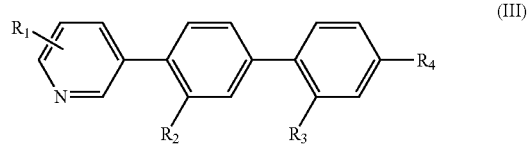

(III)

In yet another preferred embodiment, the inhibitors are compounds of formula (II), wherein R is $CR_5$. These compounds can be represented by formula (IV):

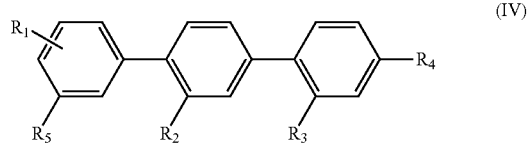

(IV)

In one preferred embodiment, the inhibitors are compounds as described above with reference to any of formulae (I)-(IV), wherein $R_1$ is hydrogen, hydroxy, or $C_1$-$C_6$ alkoxy. In one preferred embodiment, the inhibitors are compounds as described above with reference to any of formulae (I)-(IV), wherein $R_1$ is hydrogen.

In another preferred embodiment, the inhibitors are compounds as described above with reference to any of formulae (I)-(IV), wherein $R_2$ is $C_1$-$C_6$ alkyl, halo($C_1$-$C_6$ alkyl), hydroxy($C_1$-$C_6$ alkyl), formyl($C_0$-$C_6$ alkyl), amino($C_1$-$C_6$ alkyl), or sulfanyl($C_1$-$C_6$ alkyl).

In yet another preferred embodiment, the inhibitors are compounds as described above with reference to any of formulae (I)-(IV), wherein $R_2$ is $C_1$-$C_6$ alkyl, halo($C_1$-$C_6$ alkyl), hydroxy($C_1$-$C_6$ alkyl), or formyl($C_0$-$C_6$ alkyl).

In yet another preferred embodiment, the inhibitors are compounds as described above with reference to any of formulae (I)-(IV), wherein $R_2$ can be $C_1$-$C_6$ alkyl, halo($C_1$-$C_6$ alkyl), or hydroxy($C_1$-$C_6$ alkyl). For example, in certain embodiments $R_2$ can be $C_1$-$C_6$ alkyl such as methyl, ethyl, or isopropyl. In other embodiments, $R_2$ can be halo($C_1$-$C_6$ alkyl) such as fluoromethyl, difluoromethyl, or trifluoromethyl. $R_2$ can, in certain embodiments, be hydroxy($C_1$-$C_6$ alkyl). For example, the hydroxy($C_1$-$C_6$ alkyl) can be hydroxymethyl, 1-hydroxyethyl, or 2-hydroxyethyl.

In another preferred embodiment, the inhibitors are compounds as described above with reference to any of formulae (I)-(IV), wherein $R_2$ is $C_1$-$C_6$ alkyl. In certain preferred embodiments $R_2$ is methyl.

In another preferred embodiment, the inhibitors are compounds as described above with reference to any of formulae (I)-(IV), wherein $R_3$ is $C_1$-$C_6$ alkyl, —$(CH_2)_{1-5}$—C(O)OH, —$(CH_2)_{1-5}$—C(O)($C_1$-$C_6$ alkoxy), —CH=CH—C(O)OH, or —CH=CH—C(O)($C_1$-$C_6$ alkoxy).

In another preferred embodiment, the inhibitors are compounds as described above with reference to any of formulae (I)-(IV), wherein $R_3$ is —$(CH_2)_{1-5}$—C(O)OH, —$(CH_2)_{1-5}$—C(O)($C_1$-$C_6$ alkoxy), or —$(CH_2)_{1-5}$—C(O)$NH_2$.

In yet another preferred embodiment, the inhibitors are compounds as described above with reference to any of formulae (I)-(IV), wherein $R_3$ is —$(CH_2)_{1-2}$—C(O)OH, or —$(CH_2)_{1-2}$—C(O)($C_1$-$C_6$ alkoxy). For example, in certain embodiments $R_3$ can be —$(CH_2)_2$—C(O)OH, —$(CH_2)_2$—C(O)(OCH$_3$), —$(CH_2)_2$—C(O)(OCH$_2$CH$_3$), or —$(CH_2)_2$—C(O)(OC(CH$_3$)$_3$). In other embodiments, $R_3$ can be —$(CH_2)_2$—C(O)OH, or —$(CH_2)_2$—C(O)(OCH$_2$CH$_3$).

In another preferred embodiment, the inhibitors are compounds as described above with reference to any of formulae (I)-(IV), wherein $R_3$ is —$(CH_2)_{1-2}$—C(O)OH. Preferably $R_3$ is —$(CH_2)_2$—C(O)OH.

In one preferred embodiment, the inhibitors are compounds as described above with reference to any of formulae (I)-(IV), wherein $R_4$ is hydroxy, halogen, $C_1$-$C_6$ alkyl, $C_1$-$C_6$ alkoxy, halo($C_1$-$C_6$ alkoxy), or benzyloxy.

In another preferred embodiment, the inhibitors are compounds as described above with reference to any of formulae (I)-(IV), wherein $R_4$ is hydroxy or $C_1$-$C_6$ alkoxy (e.g., methoxy). Preferably $R_4$ is $C_1$-$C_6$ alkoxy. In more preferred embodiment, $R_4$ is methoxy.

In one preferred embodiment, the inhibitors are compounds as described above with reference to formulae (I), (II), or (IV), wherein $R_5$ is $C_1$-$C_6$ alkyl, halo($C_1$-$C_6$ alkyl), $C_1$-$C_6$ alkoxy, or halo($C_1$-$C_6$ alkoxy).

In another preferred embodiment, the inhibitors are compounds as described above with reference to formulae (I), (II), or (IV), wherein $R_5$ is $C_1$-$C_6$ alkyl, such as methyl.

In yet another preferred embodiment, the inhibitors are compounds as described above with reference to formulae (I), (II), or (IV), wherein $R_5$ is halo($C_1$-$C_6$ alkyl), such as trifluoromethyl.

In certain preferred embodiments, the inhibitors are compounds of any of formulae (I), (II), or (IV), wherein:

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), or ($C_1$-$C_6$ alkyl)thio($C_1$-$C_6$ alkyl);

$R_3$ is —$(CH_2)_{1-2}$—C(O)OH, —$(CH_2)_{1-2}$—C(O)($C_1$-$C_6$ alkoxy), —$(CH_2)_{1-2}$—C(O)$NH_2$, —$(CH_2)_{1-2}$—C(O)NH($C_1$-$C_6$ alkyl), —$(CH_2)_{1-2}$—C(O)N($C_1$-$C_6$ alkyl)$_2$, —CH=CH—C(O)OH, —CH=CH—C(O)($C_1$-$C_6$ alkoxy); and $R_4$ is hydroxy, $C_1$-$C_6$ alkoxy, halo($C_1$-$C_6$ alkoxy), or benzyloxy.

In certain preferred embodiments, the inhibitors are compounds of any of formula (III), wherein:

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), or ($C_1$-$C_6$ alkyl)thio($C_1$-$C_6$ alkyl);

$R_3$ is —$(CH_2)_{1-2}$—C(O)OH, —$(CH_2)_{1-2}$—C(O)($C_1$-$C_6$ alkoxy), —$(CH_2)_{1-2}$—C(O)$NH_2$, —$(CH_2)_{1-2}$—C(O)NH($C_1$-$C_6$ alkyl), —$(CH_2)_{1-2}$—C(O)N($C_1$-$C_6$ alkyl)$_2$, —CH=CH—C(O)OH, —CH=CH—C(O)($C_1$-$C_6$ alkoxy); and $R_4$ is hydroxy, $C_1$-$C_6$ alkoxy, halo($C_1$-$C_6$ alkoxy), or benzyloxy.

In certain preferred embodiments, the inhibitors are compounds of any of formulae (I), (II), or (IV), wherein $R_1$ is hydrogen; $R_2$ is $C_1$-$C_6$ alkyl, halo($C_1$-$C_6$ alkyl), hydroxy($C_1$-$C_6$ alkyl), or formyl($C_1$-$C_6$ alkyl); $R_3$ is —$(CH_2)_{1-2}$—C(O)OH, —$(CH_2)_{1-2}$—C(O)($C_1$-$C_6$ alkoxy), or —$(CH_2)_{1-2}$—C(O)$NH_2$; $R_4$ is hydroxy or $C_1$-$C_6$ alkoxy; and $R_5$ is $C_1$-$C_6$ alkyl, halo($C_1$-$C_6$ alkyl), $C_1$-$C_6$ alkoxy, or halo($C_1$-$C_6$ alkoxy).

In certain preferred embodiments, the inhibitors are compounds of any of formula (III), wherein $R_1$ is hydrogen; $R_2$ is $C_1$-$C_6$ alkyl, halo($C_1$-$C_6$ alkyl), hydroxy($C_1$-$C_6$ alkyl), or formyl($C_1$-$C_6$ alkyl); $R_3$ is —$(CH_2)_{1-2}$—C(O)OH, —$(CH_2)_{1-2}$—C(O)($C_1$-$C_6$ alkoxy), or —$(CH_2)_{1-2}$—C(O)$NH_2$; $R_4$ is hydroxy or $C_1$-$C_6$ alkoxy; and $R_5$ is $C_1$-$C_6$ alkyl, halo($C_1$-$C_6$ alkyl), $C_1$-$C_6$ alkoxy, or halo($C_1$-$C_6$ alkoxy).

In certain preferred embodiments, the inhibitors are compounds of any of formulae (I)-(IV), wherein:

R, if present, is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen;

$R_2$ is $C_1$-$C_6$ alkyl;

$R_3$ is —$(CH_2)_{1-2}$—C(O)OH; and $R_4$ is $C_1$-$C_6$ alkoxy.

In certain preferred embodiments, the inhibitors are compounds of any of formulae (I)-(IV), wherein:

R, if present, is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen;

$R_2$ is methyl;

$R_3$ is —$(CH_2)_2$—C(O)OH; and $R_4$ is methoxy.

In one preferred embodiment, the inhibitors are compounds of formula (V) are of formula (VI):

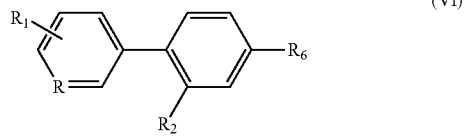

In another preferred embodiment, the inhibitors are compounds of formulae (V) or (VI) wherein:

R is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino ($C_1$-$C_6$ alkyl), sulfanyl($C_1$-$C_6$ alkyl), ($C_1$-$C_6$ alkyl)sulfanyl ($C_1$-$C_6$ alkyl), —$(CH_2)_{1-5}$—C(O)OH, —$(CH_2)_{1-5}$—C(O) ($C_1$-$C_6$ alkoxy), and —$(CH_2)_{1-5}$—C(O)$NH_2$;

$R_1$ is hydrogen, halogen, hydroxy, $C_1$-$C_6$ alkyl, halo($C_1$-$C_6$ alkyl), $C_1$-$C_6$ alkoxy, halo($C_1$-$C_6$ alkoxy), hydroxy($C_1$-$C_6$ alkyl), ($C_1$-$C_6$ alkoxy)$C_1$-$C_6$ alkyl, amino($C_1$-$C_6$ alkyl), sulfanyl($C_1$-$C_6$ alkyl), or ($C_1$-$C_6$ alkyl)sulfanyl($C_1$-$C_6$ alkyl);

$R_2$ is $C_1$-$C_6$ alkyl, halo($C_1$-$C_6$ alkyl), $C_1$-$C_6$ alkoxy, halo ($C_1$-$C_6$ alkoxy), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl ($C_1$-$C_6$ alkyl), ($C_1$-$C_6$ alkyl)sulfanyl($C_1$-$C_6$ alkyl), —$(CH_2)_{1-5}$—C(O)OH, —$(CH_2)_{1-5}$—C(O)($C_1$-$C_6$ alkoxy), —$(CH_2)_{1-5}$—C(O)$NH_2$, —CH=CH—C(O)OH, or —CH=CH—C(O)($C_1$-$C_6$ alkoxy); and $R_6$ is hydroxy, halogen, $C_1$-$C_6$ alkyl, $C_1$-$C_6$ alkoxy, halo ($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N ($C_1$-$C_6$ alkyl)$_2$, —CH=CH—C(O)OH, —CH=CH—C(O) ($C_1$-$C_6$ alkoxy), or —OS(O)$_2CF_3$.

In another preferred embodiment, the disclosure provides compounds of formulae (V) or (VI) wherein:

R is selected from N and $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl) sulfanyl($C_1$-$C_6$ alkyl), —CH=CH—C(O)OH, or —CH=CH—C(O)($C_1$-$C_6$ alkoxy); and $R_6$ is hydroxy, halogen, $C_1$-$C_6$ alkyl, $C_1$-$C_6$ alkoxy, halo ($C_1$-$C_6$ alkoxy), benzyloxy, —$(CH_2)_{1-5}$—C(O)OH, —$(CH_2)_{1-5}$—C(O)($C_1$-$C_6$ alkoxy), —$(CH_2)_{1-5}$—C(O)$NH_2$, —$(CH_2)_{1-5}$—C(O)NH($C_1$-$C_6$ alkyl), —$(CH_2)_{1-5}$—C(O)N ($C_1$-$C_6$ alkyl)$_2$, —CH=CH—C(O)OH, —CH=CH—C(O) ($C_1$-$C_6$ alkoxy), or —OS(O)$_2CF_3$.

In one preferred embodiment, the inhibitors are compounds as described above with reference to any of formulae (V)-(VI), wherein $R_1$ is hydrogen.

In another preferred embodiment, the inhibitors are compounds as described above with reference to any of formulae (V)-(VI), wherein $R_2$ is $C_1$-$C_6$ alkyl, halo($C_1$-$C_6$ alkyl), hydroxy($C_1$-$C_6$ alkyl), formyl($C_0$-$C_6$ alkyl), amino($C_1$-$C_6$ alkyl), sulfanyl($C_1$-$C_6$ alkyl), —CH=CH—C(O)OH, or —CH=CH—C(O)($C_1$-$C_6$ alkoxy).

In yet another preferred embodiment, the inhibitors are compounds as described above with reference to any of formulae (V)-(VI), wherein $R_2$ is $C_1$-$C_6$ alkyl, halo($C_1$-$C_6$ alkyl), hydroxy($C_1$-$C_6$ alkyl), formyl($C_0$-$C_6$ alkyl), —CH=CH—C(O)OH, or —CH=CH—C(O)($C_1$-$C_6$ alkoxy). In yet another preferred embodiment, the disclosure provides compounds as described above with reference to any of formulae (V)-(VI), wherein $R_2$ can be $C_1$-$C_6$ alkyl, halo($C_1$-$C_6$ alkyl), hydroxy($C_1$-$C_6$ alkyl), or —CH=CH—C(O)($C_1$-$C_6$ alkoxy). For example, in certain embodiments $R_2$ can be $C_1$-$C_6$ alkyl such as methyl, ethyl, or isopropyl. In other embodiments, $R_2$ can be halo($C_1$-$C_6$ alkyl) such as fluoromethyl, difluoromethyl, or trifluoromethyl. $R_2$ can, in certain embodiments, be hydroxy($C_1$-$C_6$ alkyl). For example, the hydroxy($C_1$-$C_6$ alkyl) can be hydroxymethyl, 1-hydroxyethyl, or 2-hydroxyethyl.

In another preferred embodiment, the inhibitors are compounds as described above with reference to any of formulae (V)-(VI), wherein $R_2$ is $C_1$-$C_6$ alkyl. In certain preferred embodiments $R_2$ is methyl.

In one preferred embodiment, the inhibitors are compounds as described above with reference to any of formulae (V)-(VI), wherein $R_6$ is hydroxy, halogen, $C_1$-$C_6$ alkyl, $C_1$-$C_6$ alkoxy, halo($C_1$-$C_6$ alkoxy), benzyloxy, or —OS(O)$_2$$CF_3$.

In another preferred embodiment, the inhibitors are compounds as described above with reference to any of formulae (V)-(VI), wherein $R_6$ is hydroxy or $C_1$-$C_6$ alkoxy (e.g., methoxy). In one preferred embodiment, the disclosure provides compounds as described above with reference to formulae (V)-(VI), wherein $R_5$ is $C_1$-$C_6$ alkyl, halo($C_1$-$C_6$ alkyl), $C_1$-$C_6$ alkoxy, or halo($C_1$-$C_6$ alkoxy).

In another preferred embodiment, the inhibitors are compounds as described above with reference to formulae (V)-(VI), wherein $R_5$ is $C_1$-$C_6$ alkyl, such as methyl.

In yet another preferred embodiment, the inhibitors are compounds as described above with reference to formulae (V)-(VI), wherein $R_5$ is halo($C_1$-$C_6$ alkyl), such as trifluoromethyl. In certain preferred embodiments, the disclosure provides compounds of any of formulae (V)-(VI), wherein:

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen, halogen, hydroxy, $C_1$-$C_6$ alkyl, halo($C_1$-$C_6$ alkyl), $C_1$-$C_6$ alkoxy, or halo($C_1$-$C_6$ alkoxy);

$R_2$ is $C_1$-$C_6$ alkyl, halo($C_1$-$C_6$ alkyl), hydroxy($C_1$-$C_6$ alkyl), ($C_1$-$C_6$ alkoxy)$C_1$-$C_6$ alkyl, formyl($C_0$-$C_6$ alkyl), amino($C_1$-$C_6$ alkyl), sulfanyl($C_1$-$C_6$ alkyl), ($C_1$-$C_6$ alkyl)thio ($C_1$-$C_6$ alkyl), or —CH═CH—C(O)($C_1$-$C_6$ alkoxy); and $R_6$ is hydroxy, $C_1$-$C_6$ alkoxy, halo($C_1$-$C_6$ alkoxy), or —OS(O)$_2$CF$_3$.

In certain preferred embodiments, the inhibitors are compounds of any of formulae (V)-(VI), wherein $R_1$ is hydrogen; $R_2$ is $C_1$-$C_6$ alkyl, halo($C_1$-$C_6$ alkyl), hydroxy($C_1$-$C_6$ alkyl), formyl($C_0$-$C_6$ alkyl), or —CH═CH—C(O)($C_1$-$C_6$ alkoxy); $R_6$ is hydroxy, $C_1$-$C_6$ alkoxy, or —OS(O)$_2$CF$_3$; and $R_5$ is $C_1$-$C_6$ alkyl, halo($C_1$-$C_6$ alkyl), $C_1$-$C_6$ alkoxy, or halo ($C_1$-$C_6$ alkoxy). The GBPB inhibitor compounds include pharmaceutically acceptable salts, esters, amides, and prodrugs thereof, including but not limited to carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," J. Pharm. Sci., 1977; 66:1-19 which is incorporated herein by reference.)

Examples of pharmaceutically acceptable, non-toxic esters of the inhibitors include $C_1$-$C_6$ alkyl esters, wherein the alkyl group is straight or branched, substituted or unsubstituted, $C_5$-$C_7$ cycloalkyl esters, as well as arylalkyl esters such as benzyl and triphenylmethyl. $C_1$-$C_4$ alkyl esters are preferred, such as methyl, ethyl, 2,2,2-trichloroethyl, and tert-butyl. Esters of the compounds of the present invention may be prepared according to conventional methods.

Examples of pharmaceutically acceptable, non-toxic amides of the inhibitors include amides derived from ammonia, primary $C_1$-$C_6$ alkyl amines and secondary $C_1$-$C_6$ dialkyl amines, wherein the alkyl groups are straight or branched. In the case of secondary amines, the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion of prodrugs is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC(CH$_3$)—, —CH$_2$CH(CH$_2$CH$_3$)CH$_2$—.

The term "alkylene" refers to a bivalent alkyl group. An "alkylene chain" is a polymethylene group, i.e., —(CH$_2$)$_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also may be substituted at one or more positions with an aliphatic group or a substituted aliphatic group.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "halo" or "halogen" as used herein, means —Cl, —Br, —I or —F.

The terms "haloalkyl", "haloalkenyl" and "haloalkoxy" refer to an alkyl, alkenyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia.

When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a benzo ring, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The GPBP inhibitors are ordinarily combined with one or more adjuvants appropriate for the indicated route of administration. The inhibitors may be mixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, the inhibitors may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The inhibitors can be administered as the sole active pharmaceutical agent, or they can be used in combination with one or more other compounds useful for carrying out the methods of the invention. When administered as a combination, the therapeutic agents can be formulated as separate compositions that are given at the same time or different times, or the therapeutic agents can be given as a single composition.

The inhibitors may be made up in a solid form (including granules, powders or suppositories) or in a liquid form (e.g., solutions, suspensions, or emulsions). The inhibitors may be applied in a variety of solutions and may be subjected to conventional pharmaceutical operations such as sterilization and/or may contain conventional adjuvants, such as preservatives, stabilizers, wetting agents, emulsifiers, buffers etc.

The inhibitors may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. The pharmaceutical compositions containing inhibitors may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preservative agents in order to provide palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the inhibitors in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the inhibitors in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Inhibitors may also be administered in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative, and flavoring and coloring agents. The inhibitor compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The inhibitor-containing compositions may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

The inhibitor-containing compositions of the present invention may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of inhibitors on the order of from about 0.01 mg to about 50 mg per kilogram of body weight per day, and more preferably between 0.1 mg to about 50 mg per kilogram of body weight per day, are useful in the treatment of the above-indicated conditions. The amount of inhibitor that may be combined with the carrier materials to produce a single dosage form will vary depending upon the host treated and the particular mode of administration. Dosage unit forms will generally contain between from about 1 mg to about 500 mg of inhibitor.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

In a fourth aspect, the present invention provides methods for diagnosing rheumatoid arthritis (RA) or pulmonary fibrosis (PF) comprising (a) contacting a plasma sample from a subject at risk of RA or PF with a GPBP-binding molecule that binds to 77 kD GPBP under conditions to promote selective binding of the GPBP-binding molecule to the GPBP;

(b) detecting complex formation between the GPBP-binding molecule and the 77 kD GPBP in the plasma sample;

(c) comparing an amount of complex formed between the GPBP-binding molecule and the 77 kD GPBP in the plasma sample to control; and (d) diagnosing the subject as having RA or PF based on the comparison, or providing the comparison to an entity for diagnosis of RA or PF.

Subjects at risk of RA are those subjects with any symptoms or risk factors for RA. Symptoms include, but are not limited to inflammation of the joints with the affected joints being swollen, warm, painful and/or stiff, particularly early in the morning on waking or following prolonged inactivity; increased joint stiffness early in the morning that typically lasts for more than an hour; tendon tethering; tendon erosion; joint surface destruction; impaired range of joint movement; deformity involving joint (including hands/fingers, feet/toes, cervical spine, knee, and shoulder); and loss of joint function.

PF is the formation or development of excess connective tissue (fibrosis) in the lungs. Symptoms of pulmonary fibrosis include, but are not limited to shortness of breath such as progressive shortness of breath (dyspnea with exertion), chronic dry, hacking coughing, fatigue and weakness, chest discomfort, and/or loss of appetite and rapid weight loss. Sometimes, fine inspiratory crackles can be heard at the lung bases on auscultation. A high resolution CAT scan will generally demonstrate abnormalities.

As shown in the examples that follow, 77 kD GPBP is a pre-inflammatory marker for RA and PF, as the amount of circulating 77 kD increases in the pre-inflammatory stage of RA and PF, and then subsides with the development of pain in a swollen joint(s) characteristic of inflammatory RA, and with the development of dyspnea with exertion characteristic of inflammatory PF. Thus, the methods can be used to identify subjects having RA or PF at the pre-inflammatory stage, permitting earlier treatment for subjects suffering from RA or PF.

Thus, in a preferred embodiment, the method can be used to diagnose RA in a subject with symptoms of pre-inflammatory RA, such as one or more swollen joints, one or more stiff joints, one or more warm joints, increased joint stiffness early in the morning that typically lasts for more than an hour, excess synovial fluid, the development of fibrous tissue in the synovium, and/or impaired range of joint movement. In a further embodiment, the subject is not experiencing pain in all of the one or more swollen joints. In further embodiments, the subject does not suffer from destruction of articular cartilage or ankylosis of one or more joints.

In another preferred embodiment, the method can be used to diagnose PF in a subject with symptoms of pre-inflammatory PF, such as chronic dry, hacking coughing; fatigue and weakness; chest discomfort; loss of appetite and/or rapid weight loss; and/or dyspnea with exertion. In a further embodiment, the subject is not suffering from dyspnea at rest.

While a particular diagnostic method may not provide a definitive diagnosis of a condition, it suffices if the method provides a positive indication that aids in diagnosis.

As used in this aspect, the amount of 77 kD GPBP may solely constitute intact 77 kD GPBP, or may comprise an amount of 77 kD GPBP and 77 kD GPBP fragments in the plasma sample.

The subject can be any subject that might benefit from diagnosis, such as a mammal. In a preferred embodiment, the subject is a human subject.

Rheumatoid arthritis (RA) is a chronic, systemic inflammatory disorder that may affect many tissues and organs, but principally attacks (synovial) joints. The process produces an inflammatory response of the capsule around the joints secondary to swelling of synovial cells, excess synovial fluid, and the development of fibrous tissue in the synovium. The pathology of the disease process often leads to the destruction of articular cartilage and ankylosis of the joints. RA can also produce diffuse inflammation in the lungs, pericardium, pleura, sclera, and also nodular lesions, most common in subcutaneous tissue.

About 1% of the world's population is afflicted by RA, women three times more often than men. Onset is most frequent between the ages of 40 and 50, but people of any age can be affected. It can be a disabling and painful condition, which can lead to substantial loss of functioning and mobility if not adequately treated. It is a clinical diagnosis made on the basis of symptoms, physical exam, X-rays, and labs tests, although the American College of Rheumatology (ACR) and the European League Against Rheumatism (EULAR) publish diagnostic guidelines.

A "GPBP-binding molecule" is a peptide or nucleic acid molecule that binds selectively to 77 kD GPBP, as opposed to one or more other biological molecules, structures, cells, tissues, etc. Exemplary embodiments of such GPBP-binding molecules include but are not limited to antibodies, aptamers or substrates. As used herein, a "GPBP substrate" is a target of GPBP biological activity that binds to 77 kD GPBP, or a fragment thereof that retains GPBP-binding activity. Such GPBP substrates include, but are not limited to, 1-20 (SEQ ID NO:18), GPBP-interacting proteins (GIPs) (SEQ ID NOS:19-23), myelin basic protein (MBP) and derivatives thereof (SEQ ID NOS:24-27), prion protein (PrP) (SEQ ID NO:28), type IV collagen α3 chain NC1 domain (α3(IV) NC1) (SEQ ID NO:29), and Alzheimer's disease beta peptide (A$\beta_{1\text{-}42}$) (SEQ ID NO:30). Exemplary references demonstrating GPBP binding of these substrates can be found in U.S. Pat. Nos. 6,579,969; 7,147,855; and 7,326,768, incorporated by reference herein in their entirety.

A "plasma sample" means blood plasma, the liquid component of blood, and is prepared, for example, by centrifugation of whole blood to remove blood cells. As used herein, a plasma sample also includes a blood serum sample, in which blood clotting factors have been removed.

The plasma sample may be obtained from any suitable subject, preferably from a mammal that is at risk of suffering from RA or PF, including but not limited to a human, dog, cat, horse, or livestock (cow, sheep, etc.). In a most preferred embodiment, the plasma sample is obtained from a human subject. As disclosed herein, the inventors have observed increased circulating 77 kD GPBP levels in animal models of RA and PF.

The antibody can be any selective GPBP antibody, whether polyclonal, monoclonal, or humanized monoclonal as described above, although monoclonal antibodies are preferred.

Conditions suitable to promote binding of GPBP-binding molecules, such as antibodies, aptamers or substrates, to 77 kD GPBP in the plasma samples can be determined by those of skill in the art based on the teachings herein and the examples provided below. For example, antibody-antigen binding often depends on hydrophobic interactions (the so called hydrophobic bonds); thus, high salt concentrations, such as in the molar range can be used to reduce nonspecific binding and increase specific antigen-antibody binding. Optionally, further steps may be included to promote selectivity and specificity, including but not limited to one or more wash steps to remove unbound 77 kD GPBP and/or GPBP-binding molecule, or unbound or weakly bound serum proteins; inhibitors of non-specific binding to reduce binding of high concentration serum proteins, control samples known to contain 77 kD GPBP and/or negative controls known not to bind to 77 kD GPBP, and/or inclusion of plasma samples known to not possess 77 kD GPBP (ex: deleted for GPBP).

The methods can test for the presence of 77 kD GPBP in the plasma sample by standard techniques including, but not limited to ELISA, immunofluorescence, and chromatography (for example, lateral flow assays where the antibody is immobilized on a surface and plasma proteins are labeled and allowed to flow over the surface under conditions suitable to permit binding of the antibody to GPBP in the plasma). In one embodiment, functional beads (Becton Dickinson technology) coupled to flow cytometry are used; this technique is an emerging method to measure the levels of proteins in biological fluid or cell/tissue extracts. Specifically, beads made of a fluorescence matrix are coated with one or more 77 kD GPBP antibodies, mixed with the plasma sample and further incubated with a detecting antibody labeled with a phycoerythrins. Finally, beads are analyzed by a flow cytometry program which selects the beads according matrix fluorescence emission and measurement of the level of the analyte through phycoerythrin emission. There are up to thirty different types of beads that can be simultaneously detected and discriminated by the cytometer. This method couples high sensitivity and performance with versatility since a specific bead type coated with GPBP antibody can be mixed with a distinct bead type coated with binding peptides for other analyte (i.e. autoantibodies) and simultaneously measured. The measurement of various analytes could enhance the potential of GPBP determination. In one embodiment, the techniques may determine only the presence or absence of the 77 kD GPBP isoform. Alternatively, the techniques may be quantitative, and provide information about the relative amount of the 77 kD GPBP in the sample. For quantitative purposes, ELISAs are preferred.

Detection of immunocomplex formation can be accomplished by standard detection techniques. For example, detection of immunocomplexes can be accomplished by using labeled antibodies or secondary antibodies. Such methods, including the choice of label are known to those ordinarily skilled in the art. Alternatively, the antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase. Examples of suitable prosthetic-group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of suitable radioactive material include $^{125}$I, $^{131}$I, $^{35}$S or $^{3}$H.

The methods comprise comparison of 77 kD GPBP levels detected in a test plasma sample with a control, such as a control from a plasma sample known to have "normal" levels of 77 kD GPBP or previously determined normal values for 77 kD GPBP in plasma from the subject from whom the plasma is obtained. In various embodiments, the control provides a standard curve using recombinant 77 kD GPBP or a reference value. In comparing the amount of 77 kD GPBP in the plasma sample to a control, an increase in 77 kD GPBP in the plasma sample relative to the control indicates the presence of RA or PF.

In another embodiment, a normal value of 77 kD GPBP as a reference for an standard curve is between ~1 ng/ml-10 ng/ml in plasma, while pre-inflammatory RA subjects exceed the normal at least 10-fold, 20-fold, 30-fold, 40-fold, 50-fold, 60-fold, 70-fold, 80-fold and even higher (i.e. 300-fold) normal values. Thus in various embodiments, a subject at risk of RA is diagnosed as having RA if the subject's 77 kD GPBP plasma levels are 100 ng/ml or higher; 200 ng/ml or higher; 300 ng/ml or higher; 400 ng/ml or higher; 500 ng/ml or higher; 600 ng/ml or higher; 700 ng/ml or higher; 800 ng/ml or higher; 900 ng/ml or higher; 1000 ng/ml or higher; 2000 ng/ml or higher; or 3000 ng/ml or higher.

Pre-inflammatory PF models exceed normal 77 kD GPBP values by at least 2-fold, 3-fold, 4-fold, 5-fold, 6-fold, 7-fold, 8-fold, or more the normal values. Thus in various embodiments, a subject at risk of PF is diagnosed as having PF if the subject's 77 kD GPBP plasma levels are 20 ng/ml or higher; 30 ng/ml or higher; 40 ng/ml or higher; 50 ng/ml or higher; 60 ng/ml or higher; 70 ng/ml or higher; or 80 ng/ml or higher.

In a further embodiment, combining 77 kD GPBP determination with analysis of other analytes the methods permit one to perform differential diagnosis or prognosis of RA or PF. In non-limiting embodiments, other analytes that could be assayed in subjects at risk of RA include rheumatoid factor (RF), anti-CCP, anti-mutated citrullinated vimentin (anti-MCV). Other analytes that could be assayed in subjects at risk of PF include transforming growth factor beta (TGF-β).

In a preferred embodiment of all embodiments and combination of embodiments of this fourth aspect, the method further comprises determining a level of C reactive protein (CRP) in the subject's plasma. CRP is a marker of inflammation. As disclosed in the examples that follow, the levels of 77 kD GPBP and CRP in the serum are inversely related in CKD and RA: 77 kD GPBP plasma levels are increased at the pre-inflammatory stage of CKD and RA and then decrease during the inflammatory period. In contrast, CRP plasma levels increase during the inflammatory phase of RA and CKD while staying at baseline levels during the pre-inflammatory phase of RA and CKD. Thus, in one embodiment, the methods further comprise measuring the levels of plasma CRP, comparing an amount of plasma CRP to control; and using the CRP comparison to aid in diagnosing the subject as having RA or PF.

In another embodiment, the invention provides methods for diagnosing CKD or immune complex-mediated GN, comprising (a) contacting a plasma sample from a subject at risk of CKD or immune complex-mediated GN with a GPBP-binding molecule that binds to 77 kD GPBP under conditions to promote selective binding of the GPBP-binding molecule to the GPBP;

(b) detecting
  (i) complex formation between the GPBP-binding molecule and the 77 kD GPBP in the plasma sample; and
  (ii) determining the subject's plasma level of C reactive protein (CRP)

(c) comparing
  (i) an amount of complex formed between the GPBP-binding molecule and the GPBP in the plasma sample to control; and
  (ii) an amount of CRP in the subject's plasma to control; and (d) diagnosing the subject as having CKD or immune complex-mediated GN based on the comparisons, or providing the comparisons to an entity for diagnosis of CKD or immune complex-mediated GN.

The methods of any of these embodiments, or combinations thereof, may further comprising measuring 77 kD GPBP and CRP levels in plasma from the subject at two or more time points (i.e.: 2, 3, 4, 5, or more time points), comparing each to control, and diagnosing the subject as having RA, PF, CKD, or immune complex-mediated GN based on the comparison over two or more measurements. In all embodiments, the CRP levels may be measured from the same plasma sample as the 77 kD GPBP levels, or from a different sample. Normal concentrations of CRP in healthy human plasma is usually lower than 3 µg/mL. As a result of inflammation CRP levels are at least 4 µg/ml, such as 10 µg/ml for mild inflammation and 40 µg-200 µg/ml (or greater) in active inflammation.

In a fifth aspect, the present invention provides methods for identifying compounds to treat CKD, immune complex-mediated GN, and/or PF, comprising contacting a 77 kD GPBP-77 kD GPBP substrate binding complex with one or more test compounds under binding conditions, wherein those test compounds that displace 77 kD GPBP from the binding complex are candidate compounds for treating CKD, immune complex-mediated GN, and/or PF.

In a sixth aspect, the present invention provides methods for identifying compounds to treat CKD, immune complex-mediated GN, and/or PF, comprising contacting a 77 kD GPBP substrate under binding conditions with
(a) one or more test compounds; and
(b) 77 kD GPBP;
wherein those test compounds that outcompete 77 kD GPBP for binding to the 77 kD GPBP substrate are candidate compounds for treating CKD, immune complex-mediated GN, and/or PF.

Suitable 77 kD GPBP substrates in these fifth and sixth embodiments are as disclosed above, including, but are not limited to, 1-20 (SEQ ID NO:18), GPBP-interacting proteins (GIPs) (SEQ ID NOS:19-23), myelin basic protein (MBP) and derivatives thereof (SEQ ID NOS:24-27), prion protein (PrP) (SEQ ID NO:28), type IV collagen α3 chain NC1 domain (α3(IV)NC1) (SEQ ID NO:29), and Alzheimer's disease beta peptide (Aβ$_{1-42}$) (SEQ ID NO:30). In one preferred embodiment, the 77 kD GPBP substrate comprises α3(IV)NC1. Exemplary references demonstrating GPBP binding of these substrates can be found in U.S. Pat. Nos. 6,579,969; 7,147,855; and 7,326,768, incorporated by reference herein in their entirety.

As shown in the examples that follow, compounds (such as antibodies) that displace 77 kD GPBP from binding complexes with 77 kD GPBP substrates, or that compete with 77 kD GPBP for binding to 77 kD GPBP substrates are candidate compounds for treating CKD, immune complex-mediated GN, and/or PF. Suitable conditions to assess binding of the test compounds to α3(IV)NC1 or other 77 kD GPBP substrates can be determined by those of skill in the art based on the teachings herein. In one embodiment, conditions such as those used in the examples that follow can be used. In one non-limiting embodiment, microwell plates may be coated with a suitable amount of α3(IV)NC1 in a suitable buffer to assess binding interactions. The plates may then be blocked to minimize non-specific binding. In one embodiment, the plates are then incubated with an amount of 77 kD GPBP (such as native 77 kD GPBP) and under suitable conditions to promote binding to the α3(IV)NC1 (to form a binding complex), followed by any appropriate wash steps (to remove unbound 77 kd GPBP) and then binding with the one or more test compounds to assess whether any of the test compounds can displace the 77 kD GPBP from the 77 kD GPBP-α3(IV)NC1 binding complex in the microwell. In an alternative embodiment, the 77 kD GPBP and the one or more test compounds are contacted under binding conditions at the same time, to identify test compounds that can outcompete 77 kD GPBP for binding to the α3(IV)NC1. In these embodiments, the 77 kD GPBP may be detectably labelled, and/or the one of more test compounds may be detectably labelled to facilitate identification and analysis of binding events. In a non-limiting, exemplary embodiment, plates are coated with 1 µg/mL poly-His-α3(IV)NC1 in PBS. Plates are coated for 16 h at 4° C. and blocked with 3% BSA in PBS for 1 h at room temperature. After blocking, plates are incubated with 1 µg/mL FLAG-77 kD GPBP, in the absence or presence of 1 µg/mL of test compounds for 1-2 hours at room temperature with mild shaking. Bound FLAG-77 kD GPBP is detected with 1 µg/mL ANTI-FLAG M2-Peroxidase.

Other exemplary suitable conditions are as disclosed above. For example, when the test compounds are antibodies, antibody-antigen binding often depends on hydrophobic interactions (the so called hydrophobic bonds); thus, high salt concentrations, such as in the molar range can be used to reduce nonspecific binding and increase specific antigen-antibody binding. Optionally, further steps may be included to promote selectivity and specificity, including but not limited to one or more wash steps to remove unbound 77 kD GPBP and/or test compounds; control samples known to contain competitors for GPBP binding to 77 kD GPBP substrates such as α3(IV)NC1 and/or negative controls known not to compete for 77 kD GPBP binding to 77 kD GPBP substrates such as α3(IV)NC1.

The methods can utilize standard techniques including, but not limited to ELISA, immunofluorescence, and chromatography. For quantitative purposes, ELISAs are preferred. Detection of binding events can be accomplished by standard detection techniques. For example, detection of binding complexes can be accomplished by using labeled antibodies or secondary antibodies. Such methods, including the choice of label are known to those ordinarily skilled in the art. Alternatively, the antibodies can be coupled to a detectable substance. The term "coupled" is used to mean that the detectable substance is physically linked to the antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase. Examples of suitable prosthetic-group complexes include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. An example of a luminescent material includes luminol. Examples of suitable radioactive material include $^{125}$I, $^{131}$I, $^{35}$S or $^{3}$H.

When the test compounds comprise polypeptide sequences, such polypeptides may be chemically synthesized or recombinantly expressed. Recombinant expression can be accomplished using standard methods in the art, as disclosed above. Such expression vectors can comprise bacterial or viral expression vectors, and such host cells can be prokaryotic or eukaryotic. Synthetic polypeptides, prepared using the well-known techniques of solid phase, liquid phase, or peptide condensation techniques, or any combination thereof, can include natural and unnatural amino acids. Amino acids used for peptide synthesis may be standard Boc (Nα-amino protected Nα-t-butyloxycarbonyl) amino acid resin with standard deprotecting, neutralization, coupling and wash protocols, or standard base-labile Nα-amino protected 9-fluorenylmethoxycarbonyl (Fmoc) amino acids. Both Fmoc and Boc Nα-amino protected amino acids can be obtained from Sigma, Cambridge Research Biochemical, or other chemical companies familiar to those skilled in the art. In addition, the polypeptides can be synthesized with other Nα-protecting groups that are familiar to those skilled in this art. Solid phase peptide synthesis may be accomplished by techniques familiar to those in the art and provided, such as by using automated synthesizers.

When the test compounds comprise antibodies, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor, N.Y., (1988).

When the test compounds comprise nucleic acid sequences, such nucleic acids may be chemically synthesized or recombinantly expressed as well. Recombinant expression techniques are well known to those in the art (See, for example, Sambrook, et al., 1989, supra). The nucleic acids may be DNA or RNA, and may be single stranded or double. Similarly, such nucleic acids can be chemically or enzymatically synthesized by manual or automated reactions, using standard techniques in the art. If synthesized chemically or by in vitro enzymatic synthesis, the nucleic acid may be purified prior to introduction into the cell. For example, the nucleic acids can be purified from a mixture by extraction with a solvent or resin, precipitation, electrophoresis, chromatography, or a combination thereof. Alternatively, the nucleic acids may be used with no or a minimum of purification to avoid losses due to sample processing.

When the test compounds comprise compounds other than polypeptides, antibodies, or nucleic acids, such compounds can be made by any of the variety of methods in the art for conducting organic chemical synthesis.

EXAMPLES

Example 1. Goodpasture Antigen-Binding Protein-1 is a Therapeutic Target for Immune Complex-Mediated GN COL4A3BP (GPBP gene) expresses at least three polypeptides including canonical GPBP-1, also called 77-kD GPBP or GPBP (1); GPBP-2, an alternative mRNA exon splicing isoform also called CERT or GPBPΔ26 (2); and GPBP-3, a variant which results from alternative mRNA translation initiation and also called 91-kD GPBP (3). GPBP-1 is mainly secreted and interacts with type IV collagen (3); GPBP-2 localizes mainly in the cytosol (3), transports ceramide between endoplasmic reticulum and Golgi apparatus (4) and induces protein secretion (5); and GPBP-3 is associated with cellular membranes and promotes GPBP-1 exportation (3).

Type IV collagen is composed of six distinct α chains (α1-α6) that form three types of triple-helical molecules [α1.α1.α2(IV), α3.α4.α5(IV) and α5.α5.α6(IV)] (6). Major structural support for the renal glomerulus includes peripheral wrapping membrane-organized α3.α4.α5(IV) network (GBM) and central mesh-organized α1.α1.α2(IV) network (mesangial matrix). At the capillary wall, the α3.α4.α5(IV) network (epithelial) fuses with a membrane-organized α1.α1.α2(IV) network (endothelial) to yield the backbone of the capillary GBM, a principal component of the glomerular filtration barrier.

GPBP-1 is a non-conventional Ser/Thr kinase which targets type IV collagen (1) and regulates its glomerular organization (7). Thus, increased expression of GPBP-1 causes dissociation of the α3.α4.α5(IV) and α1.α1.α2(IV) network at the glomerular filtration barrier and induces expansion of the α1.α1.α2(IV) network, thereby mediating capillary collapse (glomerulosclerosis). In lupus-prone NZW mice, autoantibody production correlates with glomerular overexpression of GPBP-1 and results in immune complex deposit formation on the disrupted capillary GBM (7).

GPBP-1 is secreted to the extracellular compartment (3) and we have demonstrated that GPBP-1 is a constituent of human plasma (cGPBP-1) and that increased levels of cGPBP-1 are associated with immune complex-mediated GN (WO 2010/009856 and U.S. Pat. No. 7,935,492). Here, we show that cGPBP-1 is a therapeutic target for immune complex-mediated GN.

Results

Identification of cGPBP-1 and Assessment of its Clinical Relevance

To isolate cGPBP-1, human plasma was adsorbed onto an affinity column containing immobilized mAb N26, a GPBP-specific monoclonal antibody (mAb), as described in WO 2010/009856 and U.S. Pat. No. 7,935,492. Bound material was eluted and shown to contain a major polypeptide of ca. 77 kDa and minor polypeptides of lower $M_r$ reactive with GPBP-specific antibodies confirming that GPBP-1 and derived products are normal constituents of the human plasma. The $M_r$ of cGPBP-1 varied between 74- and 80-kDa depending on molecular mass standards used (not shown).

To measure cGPBP-1, we developed a direct sandwich ELISA using mAb N26 as the capture antibody and mAb N27-HRP as the detecting antibody, both of which bound to different non-overlapping epitopes, as described in WO 2010/009856 and U.S. Pat. No. 7,935,492. Standard curves performed with recombinant GPBP-1 displayed a linear relationship between 0.4 and 400 ng/mL Using this prototype, we have estimated the normal levels of human cGPBP-1 to be under 10 ng/mL, no detecting significant variations with age and sex.

To explore the clinical relevance of cGPBP-1 detection, we measured its levels in patients with proteinuria (>0.5 g/day) and found that these patients displayed higher cGPBP-1 levels. However, the differences in cGPBP-1 levels were more meaningful when comparing specific clinical entities and controls, since only patients undergoing IgA nephropathy or lupus nephritis displayed elevated cGPBP-1 levels whereas other with common renal diseases (polycystic kidney disease, PKD) or GN not mediated by deposit of immune complexes on glomerular collagen, had not statistically significant increase of cGPBP-1 levels, as described in WO 2010/009856 and U.S. Pat. No. 7,935,492. Similar conclusions were obtained when the detection antibody was mAb e11-2, a mAb recognizing GPBP-1 but not GPBP-2.

To assess whether elevated cGPBP-1 levels have detrimental biological effects, A549 human cells were cultured with elevated levels of recombinant cGPBP-1 (200 ng/mL) and the mRNA expression profile analyzed. No statistically significant changes in the expression of individual genes were observed; however, functional analysis of KEGG pathways revealed that elevated recombinant cGPBP-1 activated map05322 pathway (web site: genome.jp/dbget-bin/www_bget?pathway:map05322), which has been associated with the onset of SLE (Table 1).

TABLE 1

KEGG PATHWAYS: A549 + rcGPBP-1 vs A549

| ID | Size | Log Odds Ratio | P. adjusted | Name |
|---|---|---|---|---|
| hsa05322 | 149 | 0.1444 | 0.0003 | SLE |
| hsa05222 | 115 | −0.1253 | 0.1576 | Small cell lung cancer |
| hsa05211 | 96 | −0.1355 | 0.1576 | Renal cell carcinoma |
| hsa05200 | 366 | −0.0843 | 0.1576 | Pathways in cancer |
| hsa04210 | 116 | −0.1307 | 0.1576 | Apoptosis |
| hsa04120 | 159 | −0.1130 | 0.1576 | Ubiquitin mediated proteolysis |
| hsa00380 | 58 | −0.1522 | 0.1576 | Tryptophan metabolism |
| hsa04510 | 235 | −0.0969 | 0.1579 | Focal adhesion |
| hsa04914 | 113 | −0.1223 | 0.1771 | Progesterone-mediated oocyte maturation |
| hsa05218 | 97 | −0.1196 | 0.3348 | Melanoma |

Coordinated Increase of Autoantibodies and cGPBP-1 in Aged NZW Mice

We have previously reported that aged NZW mice developed an autoimmune response (SLE) associated with increased glomerular expression of GPBP-1 (7). Although the latter was attributable to increased local mRNA expression, glomerular accumulation of GPBP-1 could also be due, at least in part, to entrapment of cGPBP-1 in glomerular structures. Consequently, we explored whether the levels of cGPBP-1 reflected the natural progression of SLE in NZW mice Interestingly, cGPBP-1 plasma levels increased in aged NZW mice and were directly correlated with plasma levels of autoantibodies uncovering a relationship between elevated cGPBP-1 levels and pathological markers, but also suggesting that normalization or inhibition of cGPBP-1 levels serves as a therapeutic strategy to arrest GN progression.

Predominant Deposit of IgG Immune Complexes in NZW Mice

We have reported that NZW mice developed a lupus-prone autoimmune response consisting of IgG and IgA autoantibodies with predominant deposits of IgA immune complexes in the glomerulus (7). In the present study, however, NZW mice developed an IgG-based lupus-prone autoimmune response and no circulating IgA autoantibodies were detected (data not shown). To further investigate the relationship between autoimmune response and GN in NZW mice, kidneys of aged mice (≥8 month) were analyzed by histochemical and immunohistochemical techniques. As previously described (7), we found disrupted GBM collagen networks and abundant GPBP-1 accumulated between the epithelial component of the GBM and an enlarged mesangium or endothelial GBM component (FIG. 3A). Histological analysis also revealed the presence of multiple pathological findings (FIG. 3B): mesangial proliferation (a), hyaline thrombi (b), subendothelial deposits (c), matrix expansion (d), wire-loop deposits (e), glomerular lobularity endocapillary proliferation (g), glomerular inflammatory infiltrates (h), necrosis, karyorrhexis and pyknosis (i), occasional crescents (j), tubule-interstitial inflammatory infiltrates (k) and tubular atrophy (l). We also noted the presence of abundant granular deposits of IgG and C3c, distributed mainly at the periphery of the glomerulus and deposits of IgM, preferentially occupying the mesangium The localization of IgG and C3c deposits along the epithelial component of the GBM was further confirmed by confocal microscopy analysis and electron microscopy (see below). Finally and as previously reported (7) no clinical manifestations of GN were detectable in these mice Characterization of GPBP-1 Blocking Antibodies The ability of biotinylated mAb N12 or N26 to inhibit GPBP-1 binding to type IV collagen [α3(IV)NC1] was assessed and found that these mAbs can potentially block cGPBP-1 in vivo (FIG. 1A).

Figure 1:
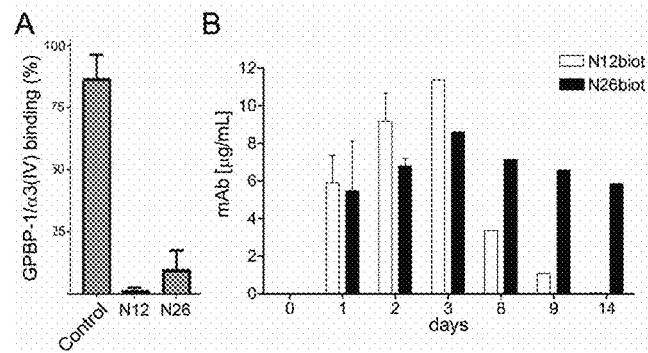
FIG. 1 Characterization of GPBP-1 blocking mAbs. A: The binding between recombinant GPBP-1 and α3(IV)NC1 was measured by ELISA in the absence (Control) or presence of the indicated mAbs. The values are expressed as binding percentage of the control which was set at 100%. Other mAbs to GPBP did not block significantly GPBP-1 binding to α3(IV)NC1 (not shown). B: NZW mice received a single intraperitoneal boost of 10 μg/g of body weight of biotinylated mAb N12 or mAb N26. Blood samples were collected at the indicated times after injection and the serum titers of the indicated mAbs measured by ELISA. Bars represent mean±S.D. (n=3).

To investigate mAb kinetics in plasma, NZW mice were injected with a single intraperitoneal boost (250 μs) and their circulating levels monitored (FIG. 1B). Both mAbs reached a peak three days after injection (10 μg/mL). The levels of mAb N12-biotin dropped by half on day 8 and were almost undetectable by day 14, whereas the levels of mAb N26-biotin on day 14 remained elevated (6 μg/mL), revealing that serum clearance of mAb N26-biotin was lower than mAb N12-biotin.

Interestingly, we observed that antibody administration increased the levels of cGPBP-1 in mice over time (not shown), suggesting that antibodies targeted cGPBP-1 and triggered a rebound effect. It has been described rebound effects on plasma levels associated with other biological treatments (8).

Treatment of NZW Mice GN with Anti-GPBP mAbs

Figure 2:
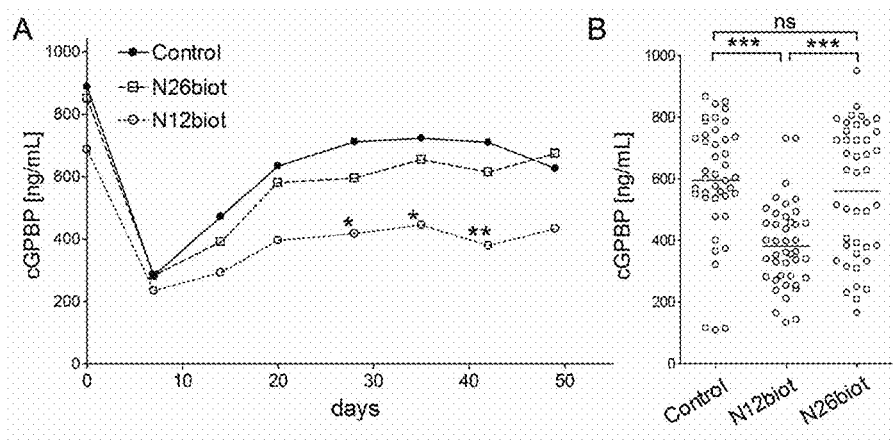
FIG. 2. Reduction of circulating GPBP-1 (cGPBP-1) levels in NZW mice treated with GPBP-specific antibodies. A: shown are the mean values (dot, square or circle) of cGPBP-1 levels in a representative therapeutic assay with the indicated antibodies. Statistically significant differences between Control and mAb N12-biotin groups were reached at the $4^{th}$, $5^{th}$ and $6^{th}$ week, using two-way ANOVA test (* $P<0.05$ and  $P<0.01$). B: Represented are the serum levels of cGPBP-1 in each individual sample collected in A (circles) and the mean value of each series (line). Statistically significant differences were found between the group treated with mAb N12-biotin and any of the other two groups, according to Kruskal Wallis/Dunn test (* $P<0.001$).

To assess the efficacy of mAbs to treat GN, aged NZW mice (8-10 months of age) were injected with PBS (carrier) or with ~1 μg/g body weight of murine IgG (Control), mAb N12-biotin or mAb N26-biotin, a dose found not to trigger a rebound effect (FIG. 2). After the first injection, cGPBP-1 levels dropped irrespective of the treatment, suggesting that a certain stress provoked by the manipulation of the mice influenced cGPBP-1 levels at the onset of the study. However, following the first week, cGPBP-1 levels increased and returned almost to the original levels over the third week, except for mice treated with mAb N12-biotin which remained reduced along the treatment, achieving statistical significance between the fourth and sixth week (FIG. 2A). Moreover, throughout the time-course of the study, the lowering of cGPBP-1 levels in mice treated with mAb N12-biotin was more effective than mice treated with mAb N26-biotin (FIG. 2B).

Figure 3:
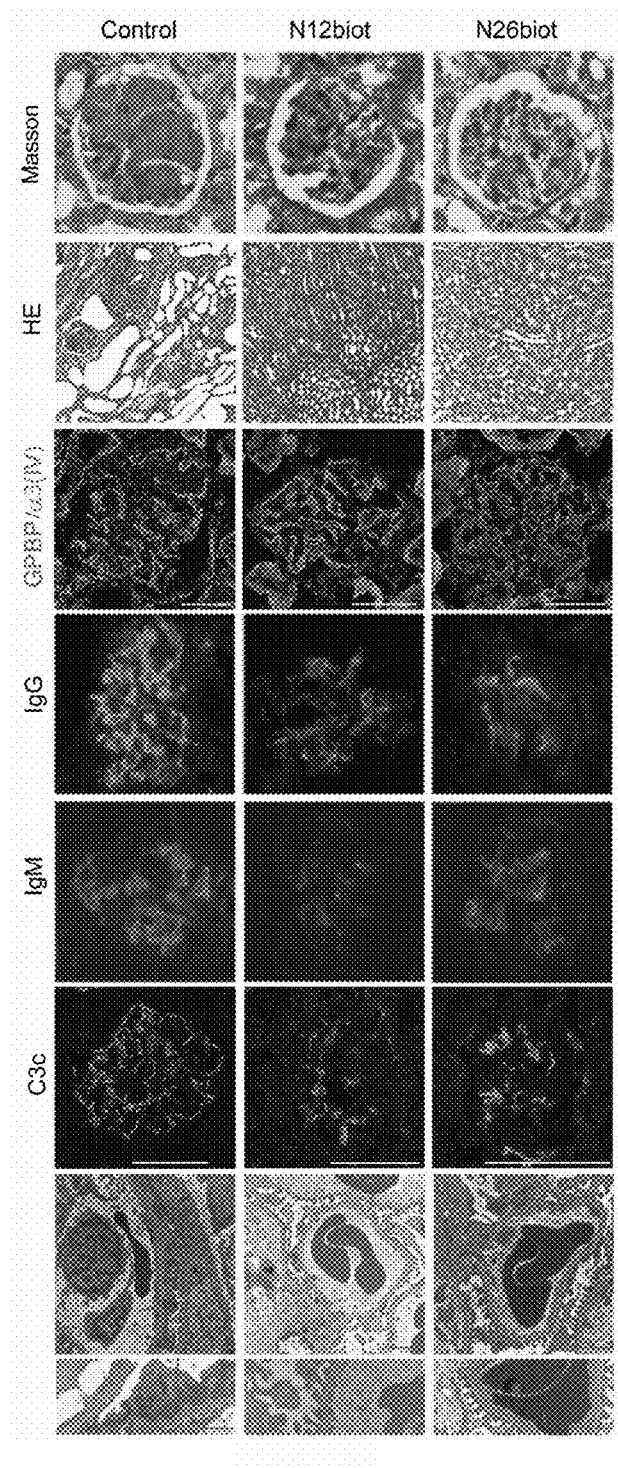
FIG. 3. Administration of GPBP-1 blocking mAbs attenuates GN progression in NZW mice. Shown are representative glomerular sections of the indicated groups of mice [Control (n=6), mAb N12 (n=5), mAb N26 (n=5)] which were analyzed by histochemical, immunofluorescence and EM procedures. Heamatoxylin/Eosin (HE) and Masson's trichrome (Masson) stainings were used to identify glomerular architecture, tubular atrophy and inflammatory infiltrates. Standard indirect immunofluorescence was used to visualize IgG and IgM deposits using conventional microscopy and the distribution of C3c, GPBP-1 and α3(IV) using confocal microscopy. Micrographies show electron-dense material in the epithelial side of an enlarged capillary GBM in control mice (red arrows), abnormalities not found in mice treated with GPBP blocking mAbs. Original magnifications ×400. Confocal scale bars=35 and 54 μm (top and bottom). Electron microscopy scale bars=2 μm (top) and 1 μm (bottom).

At the end of the treatment all mice were sacrificed and renal pathology assessed (FIG. 3). Kidneys from control mice displayed abnormalities characteristic of NZW immune complex-mediated GN; however, mice treated with GPBP-specific antibodies did not present relevant glomerular or tubular lesions (HE and Mason). Accordingly, biological treatments reduced glomerular deposits of GPBP-1, did not affect tubular intracellular expression of GPBP, and reduced deposits of immune complexes (IgG, IgM and C3c). The latter was further supported by virtual absence of electron-dense deposits commonly found in the epithelial side of the capillary GBM in control mice. Consistent with all these observations, tubule-interstitial inflammatory infiltrates were sharply reduced in mice treated with GPBP-specific antibodies (HE).

Discussion

Immune complex-mediated GN including IgA nephropathy and lupus nephritis, the most serious manifestation of SLE, are poorly understood. The current therapeutic options to treat these disorders are limited and not fully effective. Belimumab, a mAb against B-lymphocyte stimulator (BLYS), represents the first drug that has been approved by the Food and Drug Administration for treating SLE in the last 50 years (9). Regardless of etiology, CKD is characterized by an inexorable progression towards ESRD which is manifested by massive tubule-interstitial fibrosis, the final common pathological stage of all type of kidney diseases. Thus, there is a need of new biomarkers and therapeutic targets for early detection and attenuation of CKD progression.

We have previously reported that aged NZW mice develop IgA and IgG lupus-prone autoantibody response with predominant deposits of IgA in the glomerulus (7). Here we show that NZW mice develop a lupus-prone IgG autoimmune response with predominant glomerular deposit of IgG. These findings suggest that the genetic background of NZW mice predispose to SLE and immune complex-mediated GN, but the composition of the immune complexes deposited depends, by and large, on the nature of autoimmune response. Since NZW mice are genetically homogenous, the differences in the autoimmune response and therefore, in the composition of immune complexes being deposited, are expected to depend on environmental factors. Consistent with this, our previous studies were performed with NZW mice hosted in standard animal facilities whereas for the present study NZW mice were maintained in a pathogen-free environment. To investigate this possibility, young NZW mice obtained from a commercial supplier were maintained in pathogen- or non pathogen-free conditions and further confirmed that NZW mice predominantly deposited IgG in pathogen-free and IgA in non pathogen-free environment (unpublished observations). However in both of our studies, GPBP-1-dependent GBM collagen alterations were similar with the exception of the inflammatory manifestations which can be attributed to the more pro-inflammatory condition of the IgG immune complex deposits. Collectively, the evidence indicates that the genetic background in NZW mice predispose for both lupus-prone autoantibody production and increased GPBP-1 glomerular expression; however, environmental factors would ultimately condition pathological severity in determining the type of autoantibodies being produced and deposited on disrupted GBM. Accordingly, NZW mice developed an "inflammatory" lupus nephritis-like (present example) or a "non inflammatory" IgA nephropathy-like (7) depending on whether they were maintained in a pathogen-free or in a less restrictive environment, respectively.

When administered, blocking antibodies are expected to specifically inhibit the activity of extracellular GPBP-1 which comprises both tissue-bound GPBP-1 and cGPBP-1. Thus, therapeutic assays herein represent a unique test to determine the pathogenic role of extracellular GPBP-1 in clinically silent lupus nephritis-like developed by NZW mice. Our results suggest that antibody treatment virtually repairs GBM collagen-based alterations, reduces the glomerular deposits of immune complexes and consequently, attenuates inflammation. Two independent mAbs which display different ability to lower cGPBP-1 levels, but similar activity blocking of GPBP-1 binding to GBM collagen, attenuate GN progression in a similar fashion. The latter indicates that therapeutic effects depend more on blocking than on clearance of cGPBP-1 levels. Moreover, anti-GPBP therapy apparently reduces glomerular GPBP-1 deposits more efficiently (FIG. 3) than it lowers cGPBP-1 levels (FIG. 2), suggesting that glomerular GPBP-1 is responsible for GBM collagen disorganization.

Blocking antibodies are expected to lower glomerular GPBP-1 by reducing the capacity of cGPBP-1 to bind GBM collagen and by enhancing the release of tissue-bound GPBP-1. Although it remains to be determined how cGPBP-1 levels influences tissue-bound GPBP-1 levels, both GPBP-1 sources are likely operative and, in a more general context, account for primary (predominant local production) or secondary (predominant distant production) immune complex-mediated GN.

In contrast to the beneficial effects on GN progression, treatment with mAbs was not effective in reducing or attenuating the autoimmune response. (unpublished observations) Although elevation of circulating GPBP-1 and autoantibodies could be associated but unrelated pathogenic events, their positive correlation in individual mice (unpublished observations) rather suggests that the induction of cGPBP-1 levels occurs downstream of autoantibody production in a common unique pathogenic cascade. Consistently, increased GPBP-1 expression induced immune complex GN in the absence of autoantibody production (7).

Collectively, the data suggest that tissue-bound autoantibodies induce GPBP-1 expression and secretion. GPBP-1 either remains bound to tissue in the surrounding extracellular compartment or enters the plasma. In the glomerulus, tissue-bound GPBP-1 results from local production and entrapment of cGPBP-1. No matter, accumulation of tissue-bound GPBP-1 results from increased local production (primary GN) or from increased distal production and subsequent entrapping (secondary GN), GBM collagen undergoes disorganization and promotes additional immune complex deposit formation. Immune complex deposits and lupus-prone cellular stimuli, mediated by elevated cGPBP-1, positively regulate the pathogenesis which perpetuates SLE and GN progression. Anti-GPBP blocking antibodies attenuate GBM collagen disorganization and immune complex deposit formation, and disrupt the pathogenic feedback. Our data identify cGPBP-1, pathogenic factor and therapeutic target in immune complex-mediated GN.

REFERENCES FOR EXAMPLE 1

1. Raya A, Revert F, Navarro S and Saus J. Characterization of a novel type of serine/threonine kinase that specifically phosphorylates the human Goodpasture antigen. *J Biol Chem* 1999; 274: 12642-12649.
2. Raya A, Revert-Ros F, Martinez-Martinez P, Navarro S, Rosello E, Vieites B, Granero F, Forteza J and Saus J. Goodpasture antigen-binding protein, the kinase that phosphorylates the Goodpasture antigen, is an alternatively spliced variant implicated in autoimmune pathogenesis. *J Biol Chem* 2000; 275: 40392-40399.
3. Revert F, Ventura I, Martinez-Martinez P, Granero-Moltó F, Revert-Ros F, Macias J and Saus J. Goodpasture antigen-binding protein is a soluble exportable protein that interacts with type IV collagen. Identification of novel membrane-bound isoforms. *J Biol Chem* 2008; 283: 30246-30255.
4. Hanada K, Kumagai K, Yasuda S, Miura Y, Kawano M, Fukasawa M and Nishijima M. Molecular machinery for non-vesicular trafficking of ceramide. *Nature* 2003; 426: 803-809.
5. Fugmann T, Hausser A, Schöffler P, Schmid S, Pfizenmaier K and Olayioye M A. Regulation of secretory transport by protein kinase D-mediated phosphorylation of the ceramide transfer protein. *J Cell Biol* 2007; 178: 15-22.
6. Hudson B G, Tryggvason K, Sundaramoorthy M and Neilson E G. Alport's syndrome, Goodpasture's syndrome, and type IV collagen. *N Engl J Med* 2003; 348: 2543-2556.
7. Revert F, Merino R, Monteagudo C, Macias J, Peydró A, Alcácer J, Muniesa P, Marquina R, Blanco M, Iglesias M, Revert-Ros F, Merino J and Saus J. Increased Goodpasture antigen-binding protein expression induces type IV collagen disorganization and deposit of immunoglobulin A in glomerular basement membrane. *Am J Pathol* 2007; 171: 1419-1430.

8. Chung E S, Packer M, Lo K H, Fasanmade A A, Willerson J T; Anti-TNF Therapy Against Congestive Heart Failure Investigators. Anti-TNF Therapy Against Congestive Heart Failure Investigators: Randomized, double-blind, placebo-controlled, pilot trial of infliximab, a chimeric monoclonal antibody to tumor necrosis factor-alpha, in patients with moderate-to-severe heart failure: results of the anti-TNF Therapy Against Congestive Heart Failure (ATTACH) trial. *Circulation* 2003; 107: 3133-3140.

9. Sanz I, Yasothan U and Kirkpatrick P. Belimumab. *Nat Rev Drug Discov* 2011; 10: 335-336.

Example 2. cGPBP-1 is a Pre- and Pro-Inflammatory Biomarker

GPBP-1 is a Pro-Inflammatory Factor.

The finding that anti-GPBP-1 antibody treatment results in a reduction of the inflammatory infiltrates (FIG. 3), have prompted us to investigate whether GPBP-1 acts as a pro-inflammatory factor.

Comparative analysis of transcriptomes of A549 cells expressing or not expressing human recombinant GPBP-1 revealed that the expression of NLRP3 was specifically increased in response to human recombinant GPBP-1 expression whereas the expression of other related NLRP family members remained unchanged (Table 2).

TABLE 2

| GEN | statistic | Fold | p, adjusted |
|---|---|---|---|
| NLRP2 | −0.518610385 | −0.069824178 | 0.783545114 |
| NLRP3 | 8.547879904 | 1.771963852 | 0.003351881 |
| NLRP4 | 1.574117626 | 0.388428279 | 0.322787609 |
| NLRP5 | 1.216975198 | 0.691560834 | 0.445902128 |
| NLRP6 | −1.526104933 | −0.819338257 | 0.336900082 |
| NLRP7 | −0.207647712 | −0.016592656 | 0.932245268 |
| NLRP8 | −0.244957718 | −0.187884448 | 0.915529983 |
| NLRP9 | 0.473037136 | 0.039491996 | 0.805796945 |

Similarly, the over-expression of GPBP-1 in Neuro 2a cells induced elevated mRNA expression of IL-1β and NLRP5 a component of the inflammasome. All of which suggests that GPBP-1 induces pro-IL-1β expression and inflammasome activation.

In order to study this relationship, we used macrophages RAW264.7 and LPS and doxorubicin (1) to assess pro-IL-1β expression and IL-1β release. Many different agents such as asbestos, silicates, uric acid crystals or doxorubicin are inflammasome activators (2), but they are unable to induce expression of pro-IL-1β (37 KDa) in macrophages which depends on agonists of the Toll-like receptors (TLR) (i.e. LPS). Upon priming macrophages with LPS pro-IL-1β accumulates in the cytosol, and inflammasome activators lead to pro-IL-1β cleavage and to release of mature IL-1β (17 KDa) to the extracellular medium (3).

Figure 4:
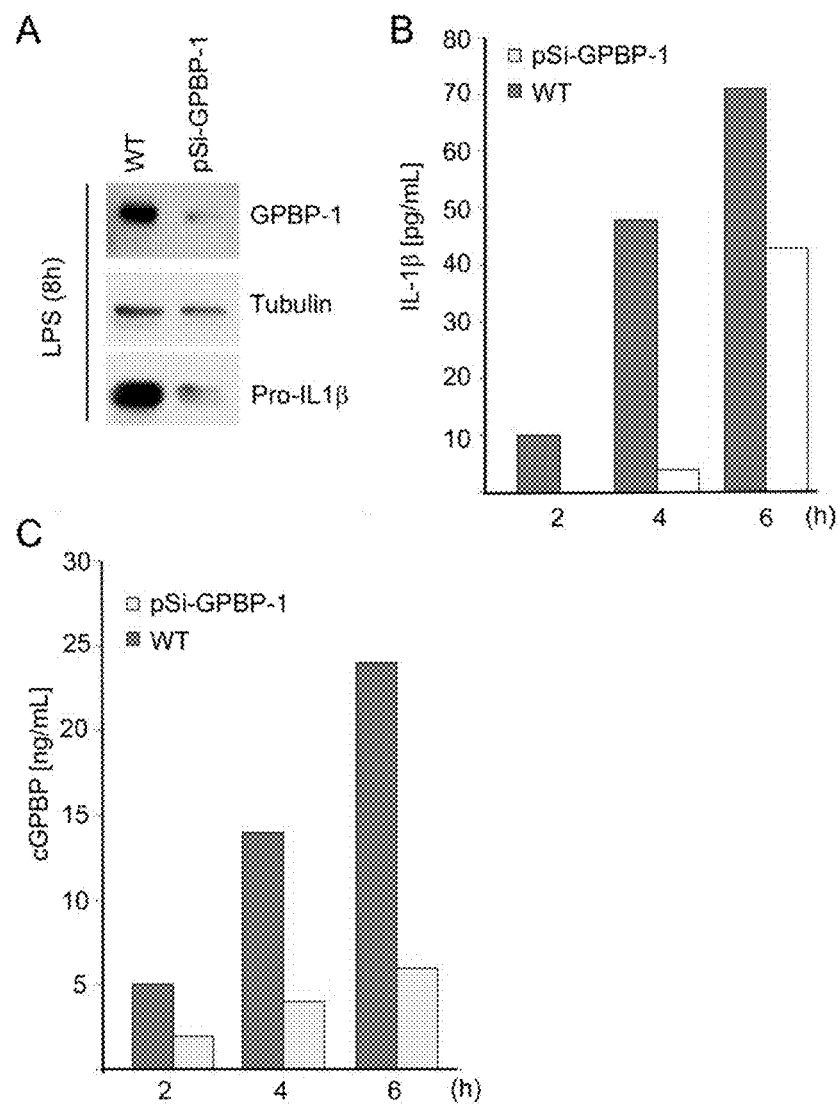
FIG. 4. Downregulation of GPBP-1 reduces pro-IL-1β levels and delays IL-1β secretion. A: Wild type and GPBP-1-silenced (pSi-GPBP-1) RAW 264.7 cells were primed for 8 hours with LPS and pro-IL-1β and GPBP-1 were detected in cell lysates by Western blot with specific antibodies. B and C: Wild type and GPBP-1-silenced (pSi-GPBP-1) RAW 264.7 cells were primed overnight with 1 μg/ml of LPS and NLRP3 was activated with 10 μM doxorubicin for the indicated times. IL-1β (B) and cGPBP-1 (C) were detected in media supernatants by ELISA.

In our assays, RAW264.7 macrophages were primed overnight with 1 μg/ml of LPS and NLRP3 inflammasome was activated with 10 μM of doxorubicin. Secreted IL-1β and cGPBP-1 in culture media were measured by ELISA at the indicated times, and cytosolic expression of pro-IL-1β and GPBP-1 analysed in cell lysates by Western blot (FIG. 4). Silencing of GPBP-1 in RAW264.7 cells caused a reduction in pro-IL-1β synthesis and IL-1β release (FIGS. 4A and 4B). The time pattern of cGPBP-1 release in these cells was similar to that of IL-1β (FIGS. 4B and 4C) and thus GPBP-1-silenced RAW264.7 cells showed a marked decrease in cGPBP-1 release, indicating that GPBP-1 is the main GPBP isoform being secreted by the cell.

Our data also indicates that GPBP-1 induces pro-IL-1β expression and inflammasome activation which results in coordinated secretion to the extracellular compartment of both cGPBP-1 and IL-1β.

cGPBP-1 is a Pre-Inflammatory Biomarker in Patients with Proteinuria.

Figure 5:
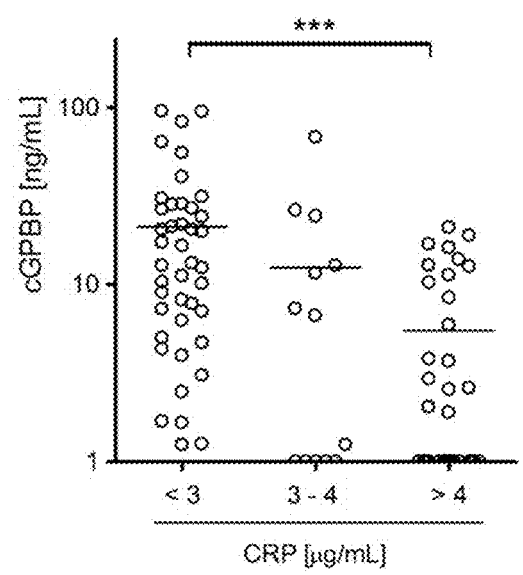
FIG. 5. cGPBP-1 and C reactive protein (CRP) levels are inversely related. cGPBP-1 and CRP were measured in sera of patients with proteinuria. The plot represents the mean (bar) and the individual (circles) cGPBP-1 levels of three groups of patients with the indicated CRP levels. Statistically significant differences were found between the group of patients with CRP<3 μg/mL and CRP>4 μg/mL, according to Kruskal Wallis/Dunn test (*** $P<0.001$).

To further determine the role of cGPBP-1 in early pre-inflammatory steps we measured the levels of a biomarker for systemic inflammation C Reactive Protein (CRP) in sera of the patients with proteinuria. We found that there exists an inverse relationship between CRP and cGPBP-1 serum levels (FIG. 5), indicating that cGPBP-1 levels increase earlier than CRP levels in these patients and thus cGPBP-1 should be envisioned as a pre-inflammatory biomarker in patients with proteinuria.

cGPBP-1 is a Pre-Inflammatory Biomarker for RA

Figure 6:
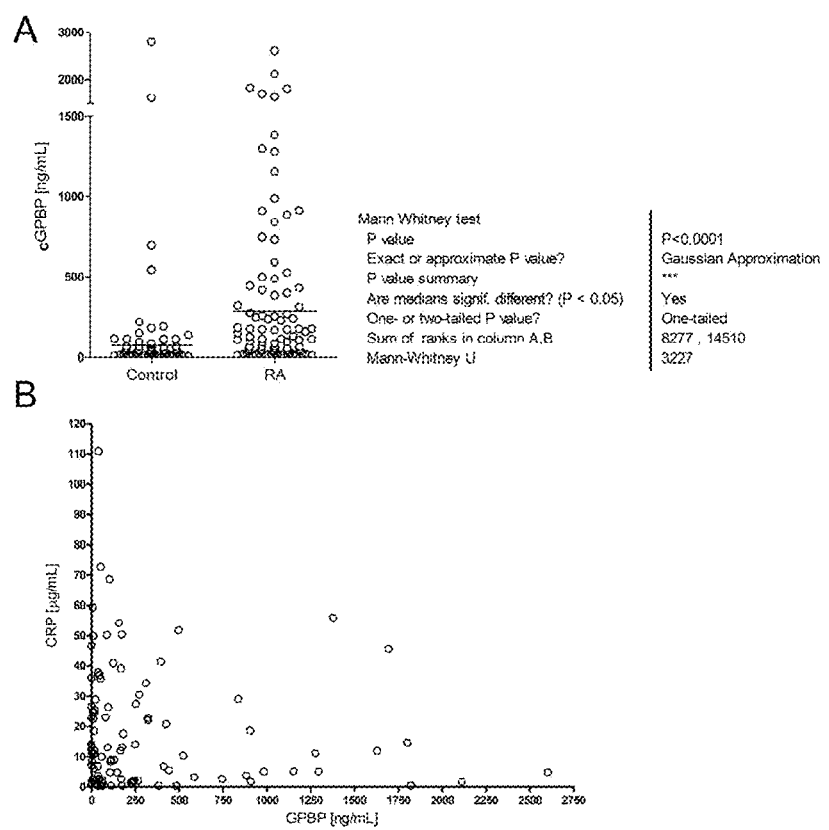
FIG. 6. Patients with RA show augmented circulating GPBP-1 levels which are inversely regulated with circulating CRP levels. In A circles represent circulating GPBP-1

In order to determine the scope of the above findings, we measured cGPBP-1 levels in patients undergoing autoimmune response mediating RA and found that these patients show increased cGPBP-1 levels with respect to control individuals (FIG. 6A). Interestingly, when we measured both cGPBP-1 and CRP levels in these patients we arrived to a similar conclusions then when analyzing patients undergoing proteinuria, and thus cGPBP-1 and CRP levels were shown to be counter-regulated (FIG. 6B).

The enormous progress made in recent decades in our understanding of the immunological mechanisms involved in the pathogenesis of RA has been largely brought by the development of experimental animal models. Among these, the most studied and frequently used is the autoimmune arthritis model after immunization with bovine type II collagen (CIA). CIA development is controlled by the MEW (4) and its clinical evolution is governed by sex hormones, and it is more severe in males or females masculinized with testosterone (5). Recent findings support that an expression of recombinant human Bcl-2 in T cells inhibits the development of CIA. This is likely because the anti-apoptotic molecule allows the population of regulatory T cells suppressing autoimmune response to expand (6). We used this experimental model to study the regulation of the cGPBP-1 levels in CIA development. In both collagen type II-immunized non-Transgenic (tg) female mice, developing a mild CIA, and Bcl-2-Tg female mice that fail to develop CIA, the levels of cGPBP-1 remain unchanged during the whole autoimmune process (p>0.05). In contrast, mice developing a severe CIA [collagen type II-immunized male mice or non-Tg female and Bcl-2-Tg females that are depleted in regulatory T cells after treatment with an anti-CD25 monoclonal antibody (5,6) exhibit very high levels of cGPBP-1 preceding the onset of a clinical CIA (4 weeks after CIA induction; p<0.02 in all cases), but these levels are significantly reduced, even below the levels observed in healthy non-immunized controls, once CIA is clinically manifested with high severity (8 weeks after CIA induction; p<0.05 in all cases; FIG. 7). Collectively, our data indicates that circulating GPBP-1 is a biomarker for early stage in RA pathogenesis.

Discussion

IL-1β is a prototypic multi-functional cytokine, mainly produced by blood monocytes, but also by macrophages, dendritic cells and by a variety of cells of nearly all types (7).

IL-1β is involved in the pathogenesis of several inflammatory disorders and in human and animal models of GN (7, 8, 9, 10).

IL-1β and cGPBP-1 release are coordinated upon the same pro-inflammatory stimulus that activate inflammasome. Under pro-inflammatory conditions such as LPS stimulation, pro-IL-1β and GPBP-1 are accumulated inside the cell. Then, after doxorubicin-mediated inflammasome activation, both IL-1β and cGPBP-1 are secreted to extracellular media.

Downregulation of GPBP-1 decreases the production of pro-IL-1β and delays the release of IL-1β in the cultured macrophage-like murine cell line RAW 264.7 revealing that GPBP-1 expression and activation is an earlier step than pro-IL 1β expression and activation in the pro-inflammatory cascade We found the cGPBP-1 concentration is under 10 ng/ml in the sera of healthy controls, and is significantly increased in the sera of IgA nephropathy and lupus nephritis patients (see above). This is consistent with our previous findings that GPBP-1 accumulates in the glomerulus of aged NZW kidneys undergoing subclinical immune complex-mediated GN (11). Macrophages RAW264.7 secrete large amounts of cGPBP-1 (>20 ng/ml) along with IL-1β after pro-inflammatory stimulus, raising the possibility that cGPBP-1 may function as an autocrine, paracrine (cGPBP-1 in glomerulus) or even endocrine pro-inflammatory factor (cGPBP-1 in serum). Moreover, GPBP-2 has been previously proposed as a target for treating-inflammation (12), since its inhibition is expected to limit the availability of ceramides for PGE2 synthesis in response to IL-1β, suggesting that both GPBP-1 and GPBP-2 are part of a pro-inflammatory cascade. Additionally, we have compared the levels of cGPBP-1 with those of CRP, a marker of systemic inflammation. The serum levels of these proteins show an inverse relationship in the sera of patients with proteinuria or RA, which suggest a dual role for cGPBP-1 as a pre- and pro-inflammatory factor.

REFERENCES

1. Sauter K A, Wood L J, Wong J, Iordanov M and Magun B E. Doxorubicin and daunorubicin induce processing and release of interleukin-1β through activation of the NLRP3 inflammasome. *Cancer Biol Ther* 2011; 11: 1008-1016.
2. Schroder K, Zhou R and Tschopp J. The NLRP3 Inflammasome: A Sensor for Metabolic Danger? *Science* 2010; 327: 296-300.
3. Perregaux D and Gabel C A. Interleukin-1β Maturation and Release in Response to ATP and Nigericin. *J Biol Chem* 1994; 269: 15195-15203.
4. Holmdahl R, Bockermann R, Bäcklund J and Yamada H. The molecular pathogenesis of collagen-induced arthritis in mice—a model for rheumatoid arthritis. *Ageing Res Rev* 2002; 1, 135-147.
5. Jansson L and Holmdahl R. Oestrogen-induced suppression of collagen arthritis; 17 beta-oestradiol is therapeutically active in normal and castrated F1 hybrid mice of both sexes. *Clin Exp Immunol* 1992; 89: 446-451.
6. González J, Tamayo E, Santiuste I, Marquina R, Buelta L, González-Gay M A, Izui S, López-Hoyos M, Merino J and Merino R. CD4+CD25+ T cell-dependent inhibition of autoimmunity in transgenic mice overexpressing human Bcl-2 in T lymphocytes. *J Immunol* 2007; 178: 2778-2786.
7. Church L D, Cook G P and McDermott M F. Primer: inflammasomes and interleukin 1beta in inflammatory disorders. *Nat Clin Pract Rheumatol* 2008; 4: 34-42.
8. Timoshanko J R, Kitching A R, Iwakura Y, Holdsworth S R and Tipping P G. Contributions of IL-1beta and IL-1alpha to crescentic GN in mice. *J Am Soc Nephrol* 2004; 15: 910-918.
9. Goldbach-Mansky R and Kastner D L. Autoinflammation: the prominent role of IL-1 in monogenic autoinflammatory diseases and implications for common illnesses. *J Allergy Clin Immunol* 2009; 124: 1141-9; quiz 1150-1.
10. Aringer M and Smolen J S. Cytokine expression in lupus kidneys. *Lupus* 2005; 14: 13-18.
11. Revert F, Merino R, Monteagudo C, Macias J, Peydró A, Alcácer J, Muniesa P, Marquina R, Blanco M, Iglesias M, Revert-Ros F, Merino J and Saus J. Increased Goodpasture antigen-binding protein expression induces type IV collagen disorganization and deposit of immunoglobulin A in glomerular basement membrane. *Am J Pathol* 2007; 171: 1419-1430.
12. Lamour N F, Stahelin R V, Wijesinghe D S, Maceyka M, Wang E, Allegood J C, Merrill A H Jr, Cho W, Chalfant C E. Ceramide kinase uses ceramide provided by ceramide transport protein: localization to organelles of eicosanoid synthesis. *J Lipid Res.* 2007; 48:1293-304.

Example 3. Goodpasture Antigen-Binding Protein-1 (GPBP-1) Inhibitors as Drugs for the Treatment of Pulmonary Fibrosis Pulmonary fibrosis (PF) occurs when the lung tissue becomes damaged and scarred. PF can be developed by unknown causes (idiopathic PF) or be associated or induced by many conditions including chronic inflammatory processes, infections, environmental agents, exposure to ionizing radiation and certain medications (1). In this regard, it has been estimated that about 5-10% of patient under chemotherapy by cancer may develop some degree of PF. Thus, bleomycin and doxorubicin have been shown to induce PF in different animal species including humans (2-5). The prognosis of patients with PF is bad and the majority of patients with this disease are dead within 5 years. Unfortunately, no medication has been shown to improve the outcome of patients with PF (1) and lung transplantation is the only therapeutic option available at present.

GPBP-1 regulates the supramolecular organization of structural proteins both inside and outside of the cell (6, 7). Since the expression of GPBP-1 is regulated by inflammatory stimuli such as TNFα (8, 9), and inflammation plays a major role in the initiation and or progression of the fibrotic process, we hypothesize here that GPBP-1 may be a key molecule involved in the pathogenesis of diseases characterized by the aberrant accumulation of different types of collagens (ie: collagen type I) such as PF. In our present study, we have characterized two compounds from the Pretswick Chemical Library that have the ability to modulate GPBP-1 activity in vitro. The therapeutic capacity of these compounds, pinacidil and mirycetin, has been evaluated in vivo using the experimental model of doxorubicin-induced PF in mice. Finally, to confirm that GPBP-1 is a target in doxorubicin induced-PF we used two different monoclonal antibodies to GPBP-1, mAb 14 and mAb N12, to treat doxorubicin induced-PF in mice.

Results

Intratracheal Instillation of Doxorubicin Promotes PF.

The intratracheal (i.t.) instillation of 75 µg of doxorubicin into C57BL/6 male mice causes a generalized alteration in the lung architecture 12 days after drug administration that macroscopically is characterized by the intense inflammation of the lungs that appear hemorrhagic (FIG. 8). The histological analysis shows an intense inflammatory cell infiltration that includes the presence of perivascular granulomas and interstitial matrix deposition resulting in the obliteration of alveoli (FIG. 8, HE). The collagenous nature of the interstitial matrix deposits is evidenced after Masson's trichrome staining of the lungs (FIG. 8). In parallel with the development of histological lesions, an increase in the expression of α1-collagen I gene is observed in the lungs of doxorubicin-treated mice by RT-qPCR analysis (FIG. 9).

Enhanced Expression of GPBP-1 During the Induction of Doxorubicin-Induced PF.

To explore the potential involvement of GPBP-1 in the pathogenesis of doxorubicin-induced PF, we have measured first the levels of circulating GPBP-1 at different time points after doxorubicin instillation by ELISA: serum levels of GPBP-1 sharply increase early after doxorubicin instillation (day 5) and subsequently drop reaching the lowest values at day 12 when inflammation and fibrosis are clinically evident (FIG. 9A, $p<0.05$ in all cases), in which case the levels of expression are similar to control (FIG. 9B). Finally, immunohistochemistry studies using a specific anti-GPBP-1 polyclonal antibody (6) shows that GPBP-1 is expressed at very low levels in the lung of untreated mice and its expression is confined to the bronchial epithelia (FIG. 9C). In contrast, an augmented expression of GPBP-1 is observed in the lung of doxorubicin-treated mice that is located in both the bronchial epithelia and parenchyma. In this last location, GPBP-1 expression adopts a patched pattern in association with the extracellular matrix deposits (FIG. 9C).

Pinacidil and Myricetin, Two In Vitro Inhibitors of GPBP-1, Ameliorate Doxorubicin-Induced PF In Vivo.

Two chemical compounds from the Pretwick Chemical Library, pinacidil and myricetin, were selected for their ability to interfere in vitro with GPBP-1 activity (not shown).

We have explored here the potential use of pinacidil or myricetin to treat doxorubicin-induced PF. First, mice were instilled i.t. with doxorubicin and treated from the beginning up to the end of the experiment (days 0-12) with different doses of pinacidil. A daily dose of 0.08 mg/kg of pinacidil sharply reduced the severity of doxorubicin-induced pulmonary fibrosis (FIG. 10), and consistently a significant reduced expression of pulmonary α1 (I)collagen mRNA was observed in pinacidil-treated mice (FIG. 11A). Lower doses of pinacidil resulted in a similar reduction of expression of α1 (I)collagen mRNA (FIG. 11A). Strikingly, the therapeutic effect of pinacidil was lost when administered higher doses of the drug (0.25 or 1.225 mg/kg/day) (FIG. 11 A). In contrast when mice were treated with myricetin, efficient reduction in the doxorubicin-induced fibrosis was obtained at all doses tested (FIG. 11B).

mAb 14 and mAb N26, Two Monoclonal Antibodies to GPBP-1, Ameliorate Doxorubicin-Induced PF In Vivo.

We have explored the potential use of mAb 14 and mAb N12 to treat doxorubicin-induced PF. Four groups of mice were i.t. injected with doxorubicin and were treated from the first day after i.t. instillation with a monoclonal antibody against Transforming Growth Factor (αTGFβ; 1 mg/week divided in 3 doses), a known anti-fibrotic therapy (10) or with mAb-14 (1 mg/week divided in 3 doses), or with mAb N12 (25 µg/week in a single injection), or were left untreated (Doxo). To assess the effect of treatments on pulmonary fibrosis, the mRNA expression in lungs of the α1 chain of collagen I (2) and collagen IV were determined by RT-qPCR. Doxorubicin increases both α1(I) and α1(IV) expressions (fibrosis). The mAbs against GPBP-1 reduced the expression of both α1(I) and α1(IV) better than αTGF, that did not reduce significantly the expression of α1(IV) and had a more limited effect on α1(I) expression (* $P<0.05$, *** $P<0.001$). (FIG. 12)

Conclusions

The intra-tracheal instillation of doxorubicin induced PF.
1) An increase in the levels of cGPBP-1 in sera and GPBP-1 in the lungs was observed during the development of doxorubicin-induced PF.
2) Four distinct GPBP-1 inhibitors including two mAbs against GPBP-1 ameliorated doxorubicin-induced PF.

REFERENCES

1. Noth I and Martinez F J. Recent advances in idiopathic pulmonary fibrosis. *Chest* 2007; 132: 637-650.
2. Sleijfer S. Bleomycin-induced pneumonitis. *Chest* 2001; 120: 617-624.
3. Injac R and Strukelj B. Recent advances in protection against doxorubicin-induced toxicity. *Technol Cancer Res Treat* 2008; 7: 497-516.
4. Meadors M, Floyd J and Perry M C. Pulmonary toxicity of chemotherapy *Semin Oncol* 2006; 33: 98-105.
5. Öz E and Ýlhan M N. Effects of melatonin in reducing the toxic effects of doxorubicin. *Mol Cell Biochem* 2006; 286: 11-15.
6. Revert F, Merino R, Monteagudo C, Macias J, Peydró A, Alcácer J, Muniesa P, Marquina R, Blanco M, Iglesias M, Revert-Ros F, Merino J and Saus J. Increased Goodpasture antigen-binding protein expression induces type IV collagen disorganization and deposit of immunoglobulin A in glomerular basement membrane. *Am J Pathol* 2007; 171: 1419-1430.
7. Revert-Ros F, López-Pascual E, Granero-Moltó F, Macias J, Breyer R, Zent R, Hudson B G, Saadeddin A, Revert F, Blasco R, Navarro C, Burks D, Saus J. Goodpasture antigen-binding protein (GPBP) directs myofibril formation: identification of intracellular downstream effector 130-kDa GPBP-interacting protein (GIP130). *J Biol Chem*. 2011; 286: 35030-35043.
8. Granero F, Revert F, Revert-Ros F, Lainez S, Martinez-Martinez P and Saus J. A human-specific TNF-responsive promoter for Goodpasture antigen-binding protein. *FEBS J* 2005; 272: 5291-5305.
9. Miralem T, Gibbs P E, Revert F, Saus J and Maines M D. Human biliverdin reductase suppresses Goodpasture antigen-binding protein (GPBP) kinase activity: the reductase regulates tumor necrosis factor-α-NF-κB-dependent GPBP expression. *J Biol Chem* 2010; 285:12551-12558.
10. McCormick L L, Zhang Y, Tootell E, Gilliam A C. Anti-TGF-beta treatment prevents skin and lung fibrosis in murine sclerodermatous graft-versus-host disease: a model for human scleroderma. *J Immunol.* 1999; 163: 5693-5699.

Methods

Animal Experimentation

All procedures were performed according to institutional guidelines for the use of animals in experimentation.

For in vivo studies with antibodies to treat immune complex mediated-glomerulonephritis (Example 1), NZW and C57BL/6 mice were generated and maintained in a pathogen-free environment. To monitor mAbs in vivo 8-10 month-old NZW mice received a single boost of 10 µg/g body weight of biotin-labeled mAb N12 (n=3) or N26 (n=3) and serum samples were collected at specific time points. For therapeutic assays, 8-10 month-old NZW mice received a weekly injection of 1 µg/g body weight of either mAb N12-biotin (n=5), mAb N26-biotin (n=5), IgG from mouse serum (n=3), or PBS (n=3). Treatments lasted 8 weeks and serum samples were collected immediately before injections. Antibodies or PBS were administered intraperitoneally and serum samples were obtained from mouse tail and used for analytical determinations. We did not find differences between IgG- and PBS-treated mice and both groups were collectively used as controls for statistical analysis. At the end of the treatment, all mice were sacrificed and kidneys were analyzed by standard histological techniques. Sera from 3-month old NZW mice and 8-10 months old C57BL/6 mice were used as controls in analytical studies.

For induction of PF with doxorubicin (Example 3), eight to ten weeks-old C57BL/6 male mice were purchased from Harlan Ibérica (Barcelona, Spain). For intratracheal (i.t.) instillation of doxorubicin (Sigma), mice were anesthetized by intraperitoneal (i.p.) injection of ketamine (50 µg/g of body weight), atropine sulphate (0.2 µg/g) and diazepam (4 µg/g). The trachea was localized by cutaneous incision in the anterior face of the neck and immobilized with forceps. Then 75 µl of doxorubicin chlorhydrate (1 mg/ml) were injected i.t. with a 30 G needle. Skin was then sutured with 3/0 silk. Mice were fed ad libitum with a normal chow diet and bled from the retro-orbital plexus at different time points after doxorubicin i.t. instillation. Pinacidil and Myricetin, were selected from the Pretswick Chemical Library on the basis of their capacity to inhibit the autophosphorylating activity of GPBP in vitro. Mice instilled i.t. with doxorubicin were daily injected i.p. with either with 0.027, 0.08, 0.25 or 1.225 mg/kg of Pinacidil or with 0.11, 0.34 or 0.95 mg/kg of Myricetin. Mice were sacrificed twelve days after doxorubicin administration for gene expression analysis and anatomopathological studies of the lungs.

Human Serum Samples

Human serum samples were obtained from the Hospital 12 de Octubre (Madrid, Spain) and from the Washington University George M. O'Brien Center for Kidney Disease Research (St Louis, USA) following procedures previously authorized by the corresponding Ethics Committee. Except for PKD, patient diagnosis was supported by histological analysis of the corresponding renal biopsy.

Antibodies and Western Blot

Monoclonal antibodies N12, N26, and N27 were generated against *Pichia pastoris* human recombinant GPBP-1, which production have been previously reported (1, 2). Monoclonal antibody e11-2 was generated against GST-e26, a chimeric protein expressed in *E. coli* containing the protein sequence encoded by exon 11 of GPBP-1, absent in GPBP-2, fused to glutathione S-transferase (GST). When indicated, mAbs N12 and N26 were biotin-labeled with Sulfo-NHS-LC-Biotin (Thermo Fisher Scientific, Rockford, Ill.) and used for in vivo assays. For immunofluorescence studies GPBP-1 was visualized using either mAb N27 labeled with Alexa™ Fluor 546 (Invitrogen, Carlsbad, Calif.), or chicken anti-GPBP-pep1 polyclonal antibodies previously characterized (3). Monoclonal antibody N27 labeled with horseradish peroxidase (HRP; EZ-LINK Plus™ Activated Peroxidase, Thermo Fisher Scientific) was used for detection of recombinant GPBP-1 and cGPBP-1.

SDS-PAGE and Western blotting were performed under reduced conditions following standard procedures.

Commercial Antibodies

Goat anti-type IV collagen polyclonal antibodies (Chemicon, Temecula, Calif.) labeled with Alexa™ Fluor 647 (Invitrogen, Carlsbad, Calif.), and biotin-labeled anti-α3 (IV) mAb3 (Wieslab AB, Lund, Sweden) were used for detection of glomerular α1.α1.α2(IV) and α3.α4.α5(IV) networks, respectively. Both recombinant cGPBP-1 and α3(IV)NC1 domain were detected with ANTI-FLAG M2-Peroxidase (Sigma-Aldrich, St Louis, Mo.). Complement component 3c (C3c), IgA, IgG and IgM deposits were visualized with rabbit polyclonal anti-C3c-FITC (Abcam) and goat anti-mouse IgA-, IgG- or IgM-FITC (Sigma-Aldrich), respectively. Biotinylated antibodies were detected with High Sensitivity NeutrAvidin-HRP (Thermo Fisher Scientific, Rockford, Ill.), Streptavidin-AF488 (Invitrogen) or Extravidin™-TRITC (Sigma-Aldrich). Secondary antibodies used were goat polyclonal antibodies to chicken IgY-FITC (Abcam) and donkey anti-mouse IgG-HRP (Jackson InmunoResearch Europe Ltd, Suffolk, UK).

Cell Culture

A549 cells were grown with Dulbecco's modified Eagle's F-12, while HEK 293 and RAW 264.7 were cultured with Dulbecco's modified Eagle's medium. All medium were supplemented with 10% fetal calf serum and with 1% penicillin/streptomycin.

Plasmid Construction and Cell Transfection pSilencer™ 2.1-U6 hygro vector (Ambion) was employed for stable expression of small interfering mRNAs (siRNAs) specific for silencing GPBP-1. The derived construct was named pSi-GPBP-1 and the cDNA target sequence was GCCCTATAGTCGCTCTTCC (SEQ ID NO: 11), as previously described (4).

For expression and purification of GST-e26, used for obtaining mAb e11-2 antibody, the cDNA of GPBP-1 exon 11 was cloned downstream in-frame with the cDNA of GST in the pGEX-5x-1 vector (GE Healthcare).

Transfections of RAW 264.7 cells were performed by calcium phosphate procedures using the ProFection™ Mammalian Transfection System (Promega) or Lipofectamine 2000 (Invitrogen), following the manufacturers' recommendations. The expression of GPBP-1 in individual clones was determined by Western blot analysis of cell extracts. Clones expressing reduced levels of GPBP-1 were used in functional studies.

Cell Treatment

Wild type RAW 264.7 cells and GPBP-1-silenced RAW 264.7 cells were plated at $2 \times 10^6$ cells/well in 6-well culture plates and stimulated with 1 µg/ml LPS (Sigma-Aldrich, *E. Coli* serotype 026:B6) overnight (16 h). Then, the LPS-primed macrophages were exposed to 10 µM doxorubicin (Sigma-Aldrich) during 2, 4 and 6 h. After incubation with doxorubicin, expression of pro-IL-1β and cytosolic GPBP-1 was analyzed in cell lysates by Western blot, and mature IL-1β and cGPBP-1 in media supernatants were quantified by ELISA.

Cell lysates were obtained by scrapping the cells in lysis buffer (25 mM Tris-HCl, pH 7.5, 150 mM NaCl, 1% Triton X-100, 0.1% SDS, 1 µM leupeptin, 1 mM PMSF) and incubating on ice for 10 min. Lysates were clarified by centrifugation at 15,000×g for 10 min at 4° C. and analyzed by Western blot.

Recombinant Expression and Purification of GPBP-1 and GST-e26

Recombinant poly-His-GPBP-1 used in ELISA was purified from *E. coli* transformed with GPBP-1 cDNA cloned in frame in the multiple cloning site of the expression plasmid pET-15b (Merck KGaA, Darmstadt, Germany), which adds a tag of six histidines to facilitate its purification with nickel-chelated agarose columns (Clontech Laboratories, Mountain View, Calif.) following standard procedures.

Recombinant cGPBP-1 (rcGPBP-1) was purified using ANTI-FLAG M2 Affinity Gel (Sigma-Aldrich, St Louis, Mo.) from cell culture media of a HEK 293 cell clone that constitutively secretes FLAG-GPBP-1.

GST-e26 expression was induced with 1 mM IPTG in *E. coli* DH5α cells harboring pGEX-5x-1-e26 construct, and purification was performed with GSH-agarose affinity resin (Sigma) following manufacturer's recommendations.

The purity of poly-His-GPBP-1, rcGPBP-1 or GST-e26 were assessed by SDS-PAGE and Coomassie blue staining and its integrity by Western blot using mAbs to GPBP-1 including mAb N26, mAb N27 and mAb e11-2.

Pathological Studies

All mice were sacrificed in a $CO_2$ chamber. After in vivo experiments with antibodies (Example 1), kidneys were fixed in 10% formalin and embedded in paraffin. Sections of 2 μm were obtained by an electronic rotary microtome (Microm, Walldorf, Germany) and subjected to conventional Heamatoxylin/Eosin (HE), Masson's staining (Masson).

In PF assays, mouse lungs were intrabronchially perfused with 4% phosphate buffered formalin, then incubated in this fixative during 24 hours and finally embedded in paraffin. Tissue sections of 5 μm were stained with HE or with Masson's trichrome following conventional methods. For immunohistochemistry, paraffin-embedded lungs were stained with anti-GPBP-pep1 antibodies (3), which was detected with anti-chicken-HPR and DAB substrate (Dako Diagnósticos, S.A., Barcelona Spain). Specimens were counterstained with hematoxylin.

Immunofluorescence

Kidneys were embedded in OCT (Sakura, Tokyo, Japan) and frozen. Six-μm sections were obtained with a cryostat (Microm) and stained for conventional and confocal microscopy analysis as previously described (3).

Microarray Analysis

Human A549 cells were cultured with or without 200 ng/mL of rcGPBP-1 for 3 hours. Then cells were lysed and total RNA was extracted with RNeasy™ Protect mini kit (Qiagen, Valencia, Calif.) according to manufacturer's recommendations. RNA was quantified by spectrometry with a NanoDrop™ ND1000 (NanoDrop Technologies, Wilminton, Del.) and quality confirmed by RNA 6000 Nano Bioanalyzer (Agilent Technologies, Palo Alto, Calif.) assay. Briefly, 150 ng of total RNA were used to produce Cyanine 3-CTP-labeled cRNA using the Low Input Quick™ Amp Labelling Kit One-Color (Agilent) according to the manufacturer's instructions. Following 'One-Color Microarray-Based Gene Expression Analysis' protocol Version 6.0 (Agilent), 1600 ng of labelled cRNA were hybridized with the Whole Human Genome Oligo Microarray Kit (Agilent) containing 41000+ unique human genes and transcripts. Arrays were scanned in an Agilent Microarray Scanner according to the manufacturer's instructions and data extracted using Agilent Feature Extraction Software 10.7.1 following the Agilent protocol GE1_107_Sep09, grid template 014850_D_F_20100430 and the QC Metric Set GE1_QCMT_Sep09. Analysis was performed in the Genomics Core Service of the Centro de Investigación Príncipe Felipe (Valencia, Spain) using an Agilent Microarray Scanner (Agilent Technologies, Palo Alto, Calif.).

Raw data files were background corrected using supplier's methodology and intensity signal standardized across arrays via quantile normalization algorithm. Differential gene expression assessment of all comparisons was carried out using limma moderated t-statistics. Conventional adjustment for multiple testing proposed by Benjamini Hochberg (5) was used to derive adjusted P-values. Also, for each of the comparisons performed in the study, gene set analysis was carried out using logistic regression models, and correcting for multiple testing as before (5). All analyses where carried out using Babelomics™ (6) web suite at the Bioinformatics Department of Centro de Investigación Príncipe Felipe. Array data have been deposited in GEO (accession number GSE32181).

Real Time PCR Analysis.

In assays of experimental pulmonary fibrosis, the expression of GPBP and of collagens type I and type IV mRNAs in the lung was analyzed by real-time quantitative PCR (RT-qPCR). One μg of the isolated RNA was used for cDNA synthesis with a RT-PCR kit (Amersham Pharmacia Biotech, Piscataway, N.J.), according to the manufacturer instructions. RT-qPCR was performed on a MX-3000P Stratagene instrument (Agilent Technologies, Inc., Santa Clara, Calif.) using specific primers SYBR Green PCR Master Mix (Applied Biosystems, Life Technologies Corporation). Primers used were: for α1(I) collagen gene, 5' primer 5'-TCCT-GCTGGTGAGAAAGGAT-3' (SEQ ID NO: 12) and 3' primer 5'-CTGGAGTCCCATAACGACCT-3' (SEQ ID NO: 13); for GPBP gene, 5' primer 5'-GCTGTTGAAGCT-GCTCTTGACA-3' (SEQ ID NO: 14) and 3' primer 5'-CCTGGGAGCTGAATCTGTGAA-3'(SEQ ID NO: 15); for 18S gene, 5' primer 5'-GTAACCCGTTGAACCCCATT-3' (SEQ ID NO: 16) and 3' primer 5'-GCGATGATG-GCTAACCTACC-3' (SEQ ID NO: 17). Results (in triplicate) were normalized to the ribosomal 18S subunit expression and measured in parallel in each sample. Data were expressed as mean fold change relative to control samples.

Immunopurification of cGPBP-1 cGPBP-1 was extracted from human plasma by affinity chromatography. Specifically, the plasma (200 mL) was clarified by centrifugation, filtered (0.45 μm), and diluted 1:5 (v/v) with 25 mM Tris pH 7.4, 150 mM NaCl (Tris-buffered saline, TBS) supplemented with 0.05% Tween 20 (TB ST). The supernatant was loaded onto a column containing 1 mg of mAb N26 immobilized in 1 mL of cyanogen bromide-activated-Sepharose 4B (Sigma-Aldrich). The bound material was washed with 10 mL of TBST, eluted with ImmunoPure™ Gentle Ag/Ab Elution Buffer (Thermo Fisher Scientific) and extensively dialyzed against TBS.

ELISA Procedures

To assess the interaction of GPBP-1 with the non-collagenous 1 domain of the α3 chain of type IV collagen [α3(IV)NC1], plates were coated with 1 μg/mL poly-His-GPBP-1 in PBS. After blocking, plates were incubated with 1 μg/mL FLAG-α3(IV)NC1, in absence or presence of 1 μg/mL of mAbs N12 or N26. Bound FLAG-α3(IV)NC1 was detected with 1 μg/mL ANTI-FLAG M2-Peroxidase.

Quantification of cGPBP-1 or of biotinylated mAbs was performed by sandwich ELISA coating plates with mAb N26 or poly-His-GPBP-1 at 2 μg/mL in PBS, respectively. Plates were blocked and incubated with samples (1:10-1:20 dilutions) and detection performed with mAb N27-HRP or High Sensitivity NeutrAvidin™-HRP at 1 μg/mL, respectively.

In all cases, plates were coated for 16 h at 4° C. and blocked with 3% BSA in PBS for 1 h at room temperature. Subsequent incubations were done for 1-2 hours at room temperature with mild shaking. Plates were extensively washed between steps and developed with a fluorescent HRP substrate (Quanta Blue, Thermo Fisher Scientific). Fluorescence intensity was measured with a SpectraMax™ Gemini XPS Fluorescence Microplate Reader (Molecular Devices, Sunnyvale, Calif.) and acquired data analyzed with SoftMax™ Pro Data Acquisition & Analysis software (Molecular Devices). Unless otherwise indicated all dilutions and washes were done with TBST.

Anti-ss-DNA IgG and CRP titers were measured by indirect sandwich ELISA using a commercial kit from Alpha Diagnostic Intl. (San Antonio, Tex.) and Meditec (Kiel, Germany) respectively, following manufacturer's instructions.

To assess mature IL-1β production by stimulated RAW 264.7 cells, cell-culture media were analyzed using the ELISA Ready-Set-Go kit for mouse IL-1β (eBioscience, San Diego, Calif.) following manufacturer's instructions.

Electron Microscopy Studies

Kidneys were excised and fixed by immersion in 2% paraformaldehyde and 2.5% glutaraldehyde in 0.1 M sodium phosphate pH 7.4 (PB) for 24 hours at 4° C. and then washed with PB. Sections of 200 μm were obtained with a vibratome (Leica VT-1000; Leica Microsystems Heidelberg GmbH, Mannheim, Germany), fixed with 2% osmium tetroxide in PB for 1.5 hours, washed with chilled water (3×5 min), dehydrated through sequential washes with increasing concentrations of chilled ethanol solutions (5 min with 30%, 5 min with 50%, and 10 min with 70%), washed with 2% uranile acetate in 70% ethanol for 2.5 hours at 4° C., and further dehydrated with 2×5 min washes in 70% ethanol, 2×5 min and 10 min washes with 96% ethanol, 2×7 min washes in 100% ethanol, and a single 10 min wash in dried 100% ethanol. Finally, sections were washed 2×10 min with propylene oxide and embedded in araldite (Durcupan, Sigma-Aldrich). Semithin sections of 1.5 μm and ultrathin sections of 0.08 μm were cut with a diamond knife and stained with 1% toluidine blue and lead citrate (Reynolds solution) respectively.

Statistical Analysis

Prism 4.0 software (GraphPad™ Software, San Diego, Calif.) was used for all calculations. Data were analyzed with two-way ANOVA or Kruskal-Wallis test to assess significant differences between series, and with Spearman's test to determine the statistical significance of the correlation between cGPBP-1 and anti-ssDNA autoantibodies. A P value <0.05 was considered significant.

REFERENCES

1. Raya A, Revert F, Navarro S and Saus J. Characterization of a novel type of serine/threonine kinase that specifically phosphorylates the human Goodpasture antigen. *J Biol Chem* 1999; 274: 12642-12649.
2. Raya A, Revert-Ros F, Martinez-Martinez P, Navarro S, Rosello E, Vieites B, Granero F, Forteza J and Saus J. Goodpasture antigen-binding protein, the kinase that phosphorylates the Goodpasture antigen, is an alternatively spliced variant implicated in autoimmune pathogenesis. *J Biol Chem* 2000; 275: 40392-40399.
3. Revert F, Merino R, Monteagudo C, Macias J, Peydró A, Alcácer J, Muniesa P, Marquina R, Blanco M, Iglesias M, Revert-Ros F, Merino J and Saus J. Increased Goodpasture antigen-binding protein expression induces type IV collagen disorganization and deposit of immunoglobulin A in glomerular basement membrane. *Am J Pathol* 2007; 171: 1419-1430.
4. Revert F, Ventura I, Martinez-Martinez P, Granero-Moltó F, Revert-Ros F, Macias J and Saus J. Goodpasture antigen-binding protein is a soluble exportable protein that interacts with type IV collagen. Identification of novel membrane-bound isoforms. *J Biol Chem* 2008; 283: 30246-30255.
5. Benjamini Y and Hochberg Y. Controlling the False Discovery Rate: a Practical Powerful Approach to Multiple Testing. *J R Statist Soc B* 1995; 57: 289-300.
6. Medina I, Carbonell J, Pulido L, Madeira S C, Goetz S, Conesa A, Tárraga J, Pascual-Montano A, Nogales-Cadenas R, Santoyo J, Garcia F, Marbá M, Montaner D and Dopazo J. Babelomics: an integrative platform for the analysis of transcriptomics, proteomics and genomic data with advanced functional profiling. *Nucleic Acids Res* 2010; 38 (Web Server issue): W210-W213.

We claim:

1. A method for treating pulmonary fibrosis (PF), comprising administering to a subject in need thereof an effective amount of an inhibitor of 77 kD GPBP to treat the PF, wherein the GPBP inhibitor is a compound of formula (I):

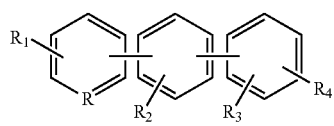

(I)

or a pharmaceutically acceptable salt thereof, wherein:

R is $CR_5$;

$R_5$ is selected from the group consisting of hydrogen, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl) amino, di($C_1$-$C_6$ alkyl)amino, hydroxy($C_1$-$C_6$ alkyl), ($C_1$-$C_6$ alkoxy)$C_1$-$C_6$ alkyl, and amino($C_1$-$C_6$ alkyl);

$R_1$ is hydrogen;

$R_2$ is $C_1$-$C_6$ alkyl or hydroxy($C_1$-$C_6$ alkyl);

$R_3$ is —$(CH_2)_{1-2}$—C(O)OH or —CH=CH—C(O)OH; and $R_4$ is $C_1$-$C_6$ alkoxy.

2. The method of claim 1, wherein the subject is a human.

3. The method of claim 1, wherein the PF is idiopathic PF.

4. The method of claim 3, wherein the subject is a human.

5. The method of claim 1, wherein

R is $CR_5$;

$R_5$ is methyl or trifluoromethyl;

$R_1$ is hydrogen;

$R_2$ is methyl;

$R_3$ is —$(CH_2)_2$—C(O)OH; and
$R_4$ is methoxy.

6. The method of claim 5, wherein the subject is a human.

7. The method of claim 5, wherein the PF is idiopathic PF.

8. The method of claim 7 wherein the subject is a human.

* * * * *